(12) United States Patent
Cocuzza et al.

(10) Patent No.: US 6,489,320 B1
(45) Date of Patent: Dec. 3, 2002

(54) 5, 5-DISUBSTITUTED-1, 5-DIHYDRO-4, 1-BENZOXAZEPIN-2 (3H)-ONES USEFUL AS HIV REVERSE TRANSCRIPTASE INHIBITORS

(75) Inventors: Anthony J. Cocuzza, Wilmington, DE (US); James D. Rodgers, Landenberg, PA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/657,518

(22) Filed: Sep. 7, 2000

Related U.S. Application Data

(62) Division of application No. 09/145,101, filed on Sep. 1, 1998, now Pat. No. 6,140,320.
(60) Provisional application No. 60/057,431, filed on Sep. 2, 1997.

(51) Int. Cl.[7] .......................... A61K 31/55; A61P 31/00; C07D 267/12
(52) U.S. Cl. .................. 514/211.05; 540/488; 540/490
(58) Field of Search ..................... 514/211.05; 540/488, 540/490

(56) References Cited

U.S. PATENT DOCUMENTS

| | | | |
|---|---|---|---|
| 4,476,133 A | 10/1984 | Hirai et al. ................. | 424/269 |
| 5,519,021 A | 5/1996 | Young et al. ............ | 514/230.5 |

FOREIGN PATENT DOCUMENTS

| | | |
|---|---|---|
| EP | 142361 | 5/1985 |
| EP | 567026 | 10/1993 |
| JP | 8259447 | 8/1996 |

*Primary Examiner*—Brenda Coleman
(74) *Attorney, Agent, or Firm*—Mary K. VanAtten

(57) ABSTRACT

The present invention relates to benzoxazepinones of formula I:

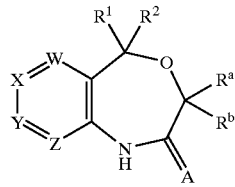

or stereoisomeric forms or mixtures, or pharmaceutically acceptable salt forms thereof, which are useful as inhibitors of HIV reverse transcriptase, and to pharmaceutical compositions and diagnostic kits comprising the same and methods of using the same for treating viral infection or as an assay standard or reagent.

17 Claims, No Drawings

5,5-DISUBSTITUTED-1,5-DIHYDRO-4,1-BENZOXAZEPIN-2 (3H)-ONES USEFUL AS HIV REVERSE TRANSCRIPTASE INHIBITORS

This application is a division of U.S. patent application Ser. No. 09/145,101 filed Sep. 1, 1998, now U.S. Pat. No. 6,140,320 which claims benefit of U.S. Provisional Application No. 60/057,431 filed Sep. 2, 1997.

FIELD OF THE INVENTION

This invention relates generally to 5,5-disubstituted-1,5-dihydro-4,1-benzoxazepin-2(3H)-ones which are useful as inhibitors of HIV reverse transcriptase, pharmaceutical compositions and diagnostic kits comprising the same, and methods of using the same for treating viral infection or as assay standards or reagents.

BACKGROUND OF THE INVENTION

Two distinct retroviruses, human immunodeficiency virus (HIV) type-1 (HIV-1) or type-2 (HIV-2), have been etiologically linked to the immunosuppressive disease, acquired immunodeficiency syndrome (AIDS). HIV seropositive individuals are initially asymptomatic but typically develop AIDS related complex (ARC) followed by AIDS. Affected individuals exhibit severe immunosuppression which predisposes them to debilitating and ultimately fatal opportunistic infections.

The disease AIDS is the end result of an HIV-1 or HIV-2 virus following its own complex life cycle. The virion life cycle begins with the virion attaching itself to the host human T-4 lymphocyte immune cell through the bonding of a glycoprotein on the surface of the virion's protective coat with the CD4 glycoprotein on the lymphocyte cell. Once attached, the virion sheds its glycoprotein coat, penetrates into the membrane of the host cell, and uncoats its RNA. The virion enzyme, reverse transcriptase, directs the process of transcribing the RNA into single-stranded DNA. The viral RNA is degraded and a second DNA strand is created. The now double-stranded DNA is integrated into the human cell's genes and those genes are used for virus reproduction.

At this point, RNA polymerase transcribes the integrated DNA into viral RNA. The viral RNA is translated into the precursor gag-pol fusion polyprotein. The polyprotein is then cleaved by the HIV protease enzyme to yield the mature viral proteins. Thus, HIV protease is responsible for regulating a cascade of cleavage events that lead to the virus particle's maturing into a virus that is capable of full infectivity.

The typical human immune system response, killing the invading virion, is taxed because the virus infects and kills the immune system's T cells. In addition, viral reverse transcriptase, the enzyme used in making a new virion particle, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to reproduce while the immune response system continues to weaken. Eventually, the HIV largely holds free reign over the body's immune system, allowing opportunistic infections to set in and without the administration of antiviral agents, immunomodulators, or both, death may result.

There are at least three critical points in the virus's life cycle which have been identified as possible targets for antiviral drugs: (1) the initial attachment of the virion to the T-4 lymphocyte or macrophage site, (2) the transcription of viral RNA to viral DNA (reverse transcriptase, RT), and (3) the processing of gag-pol protein by HIV protease.

Inhibition of the virus at the second critical point, the viral RNA to viral DNA transcription process, has provided a number of the current therapies used in treading AIDS. This transcription must occur for the virion to reproduce because the virion's genes are encoded in RNA and the host cell reads only DNA. By introducing drugs that block the reverse transcriptase from completing the formation of viral DNA, HIV-1 replication can be stopped.

A number of compounds that interfere with viral replication have been developed to treat AIDS. For example, nucleoside analogs, such as 3'-azido-3'-deoxythymidine (AZT), 2',3'-dideoxycytidine (ddC), 2',3'-dideoxythymidinene (d4T), 2',3'-dideoxyinosine (ddI), and 2',3'-dideoxy-3'-thia-cytidine (3TC) have been shown to be relatively effective in halting HIV replication at the reverse transcriptase (RT) stage.

Non-nucleoside HIV reverse transcriptase inhibitors have also been discovered. As an example, it has been found that certain benzoxazinones are useful in the inhibition of HIV reverse transcriptase, the prevention or treatment of infection by HIV and the treatment of AIDS. U.S. Pat. No. 5,519,021, the contents of which are hereby incorporated herein by reference, describes reverse transcriptase inhibitors which are benzoxazinones of the formula:

wherein X is a halogen, Z may be O. However, benzoxazinones are not part of the present invention.

U.S. Pat. No. 4,476,133 depicts CNS active 4,1-benzoxazepines of the formula:

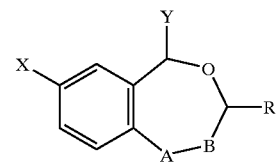

wherein A-B can be NH—C(O), R is H or $C_{1-5}$ alkyl, X is H, halo, or $NO_2$, and Y is phenyl or pyridyl. No mention is made of 5,5-disubstituted-1,5-dihydro-4,1-benzoxazepin-2 (3H)-ones which are the subject of the present invention.

EP 0,142,361 illustrates phospholipase $A_2$ inhibitors of the formula:

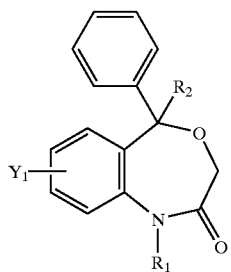

wherein $R_1$ can be a variety of cyclic and acyclic groups, but not hydrogen, $R_2$ is H, alkyl, or phenyl, and $Y_1$ is H, halo, $NO_2$ or $CF_3$. Compounds of the present invention have a hydrogen at the 1-position and do not have a phenyl group directly attached to the 5-position.

EP 0,567,026 and JP 08/259,447, which have similar disclosures, describe 4,1-benzoxazepinone derivatives of the formula:

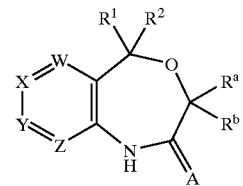

wherein ring A may be optionally substituted phenyl (also optionally substituted heteroaryl in JP '447), $R_1$, $R_2$, and $R_3$ can be a variety of groups including H and optionally substituted hydrocarbon, X is a bond or spacer and Y (B in JP '447) is optionally substituted carboxyl, hydroxyl, amino, phenyl, carbamoyl, or a nitrogen-containing heterocycle. In JP '447, B is only optionally substituted phenyl or nitrogen-containing heterocycle. Compounds of this sort are not within the presently claimed invention.

Even with the current success of reverse transcriptase inhibitors, it has been found that HIV patients can become resistant to a single inhibitor. Thus, it is desirable to develop additional inhibitors to further combat HIV infection.

SUMMARY OF THE INVENTION

Accordingly, one object of the present invention is to provide novel reverse transcriptase inhibitors.

It is another object of the present invention to provide a novel method for treating HIV infection which comprises administering to a host in need of such treatment a therapeutically effective amount of at least one of the compounds of the present invention or a pharmaceutically acceptable salt or prodrug form thereof.

It is another object of the present invention to provide a novel method for treating HIV infection which comprises administering to a host in need thereof a therapeutically effective combination of (a) one of the compounds of the present invention and (b) one or more compounds selected form the group consisting of HIV reverse transcriptase inhibitors and HIV protease inhibitors.

It is another object of the present invention to provide pharmaceutical compositions with reverse transcriptase inhibiting activity comprising a pharmaceutically acceptable carrier and a therapeutically effective amount of at least one of the compounds of the present invention or a pharmaceutically acceptable salt or prodrug form thereof.

It is another object of the present invention to provide a method of inhibiting HIV present in a body fluid sample which comprises treating the body fluid sample with an effective amount of a compound of the present invention.

It is another object of the present invention to provide a kit or container containing at least one of the compounds of the present invention in an amount effective for use as a standard or reagent in a test or assay for determining the ability of a potential pharmaceutical to inhibit HIV reverse transcriptase, HIV growth, or both.

These and other objects, which will become apparent during the following detailed description, have been achieved by the inventors' discovery that compounds of formula (I):

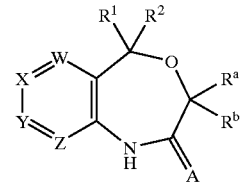

I wherein A, W, X, Y, Z, $R^a$, $R^b$, $R^1$ and $R^2$ are defined below, stereoisomeric forms, mixtures of stereoisomeric forms, or pharmaceutically acceptable salt forms thereof, are effective reverse transcriptase inhibitors.

DETAILED DESCRIPTION OF PREFERRED EMBODIMENTS

[1] Thus, in a first embodiment, the present invention provides a novel compound of formula I:

I or a stereoisomer or pharmaceutically acceptable salt form thereof, wherein:

A is O or S;

W is N or $CR^3$;

X is N or $CR^4$;

Y is N or $CR^5$;

Z is N or $CR^6$;

provided that if two of W, X, Y, and Z are N, then the remaining are other than N;

$R^a$ is selected from H, $CF_3$, $CF_2H$, cycPr, $C_{1-4}$ alkyl, $C_{3-5}$ cycloalkyl, $C_{2-4}$ alkenyl, $C_{2-4}$ alkynyl, and phenyl substituted with 0–2 $R^{10}$;

$R^b$ is selected from H, $CF_3$, $CF_2H$, cycPr, $C_{1-4}$ alkyl, $C_{3-5}$ cycloalkyl, $C_{2-4}$ alkenyl, $C_{2-4}$ alkynyl, and phenyl substituted with 0–2 $R^{10}$;

alternatively, $R^a$ and $R^b$ together form —$(CH_2)_n$—;

$R^1$ is selected from $CF_3$, $CF_2H$, $C_{1-4}$ alkyl, $C_{3-5}$ cycloalkyl, $C_{2-4}$ alkenyl, and $C_{2-4}$ alkynyl;

$R^2$ is selected from —C≡C—$R^8$, —CH=$CR^7R^8$, —$(CH_2)_p$CH$R^7R^8$, —CH$R^7$C≡C—$R^8$, —CH$R^7$CH=CH$R^8$, and CH=CHCH$R^7R^8$;

provided that when either of $R^a$ or $R^b$ is phenyl, then $R^1$ is other than $C_{1-4}$ alkyl and $C_{3-5}$ cycloalkyl and $R^2$ is other than —$(CH_2)_pCHR^7R^8$;

$R^3$ is selected from H, F, Cl, Br, I, $C_{1-3}$ alkoxy, and $C_{1-3}$ alkyl;

$R^4$ is selected from H, F, Cl, Br, I, $C_{1-3}$ alkyl substituted with 0–3 $R^{11}$, $C_{2-3}$ alkenyl, $C_{2-3}$ alkynyl, $C_{1-3}$ alkoxy, $OCF_3$, —CN, $NO_2$, CHO, $C(O)CH_3$, $C(O)CF_3$, $C(O)NH_2$, $C(O)NHCH_3$, $NR^7R^{7a}$, $NR^7C(O)OR^{7b}$, $C(O)OR^7$, $S(O)_pR^7$, $SO_2NHR^7$, $NR^7SO_2R^{7b}$, phenyl substituted with 0–2 $R^{10}$, and 5–6 membered aromatic heterocycle system containing from 1–4 heteroatoms selected from the group consisting of N, O, and S and substituted with 0–2 $R^{10}$;

alternatively, $R^3$ and $R^4$ together form —$OCH_2O$—;

$R^5$ is selected from H, F, Cl, Br, and I;

alternatively, $R^4$ and $R^5$ together form —$OCH_2O$— or a fused benzo ring;

$R^6$ is selected from H, OH, $C_{1-3}$ alkoxy, —CN, F, Cl, Br, I, $NO_2$, $CF_3$, CHO, $C_{1-3}$ alkyl, and C(O)NH2;

$R^7$, at each occurrence, is selected from H and $C_{1-3}$ alkyl;

$R^{7a}$, at each occurrence, is selected from H and $C_{1-3}$ alkyl;

$R^{7b}$, at each occurrence, is $C_{1-3}$ alkyl;

$R^8$, at each occurrence, is selected from H, $C_{1-6}$ alkyl substituted with 0–3 $R^{11}$, CH(—$OCH_2CH_2O$—), $C_{2-6}$ alkenyl, $C_{3-7}$ cycloalkyl substituted with 0–2 $R^9$, phenyl substituted with 0–2 $R^{10}$, and 5–6 membered aromatic heterocycle system containing from 1–4 heteroatoms selected from the group consisting of N, O, and S and substituted with 0–2 $R^{10}$;

$R^9$, at each occurrence, is selected from D, OH, $C_{1-3}$ alkoxy, $C_{1-3}$ alkyl, and F;

$R^{10}$, at each occurrence, is selected from OH, $C_{1-3}$ alkyl, $C_{1-3}$ alkoxy, F, Cl, Br, I, CN, $NR^7R^{7a}$, and $C(O)CH_3$;

$R^{11}$, at each occurrence, is selected from $OR^7$, CN, F, Cl, Br, I, $NO_2$, $NR^7R^{7a}$, CHO, $C(O)CH_3$, $C(O)NH_2$;

n, at each occurrence, is selected from 1, 2, 3, 4, and 5; and, p, at each occurrence, is selected from 0, 1, and 2.

[2] In a preferred embodiment, the present invention provides a novel compound of formula I, wherein:

$R^a$ is H;

$R^b$ is selected from H, $CF_3$, $CF_2H$, cyclopropyl, $CH=CH_2$, and $C_{1-4}$ alkyl;

$R^1$ is selected from $CF_3$, $CF_2H$, $C_{1-3}$ alkyl, and $C_{3-5}$ cycloalkyl; and, $R^8$ is selected from H, $C_{1-6}$ alkyl substituted with 0–3 $R^{11}$, CH(—$OCH_2CH_2O$—), $C_{2-6}$ alkenyl, $C_{3-5}$ cycloalkyl substituted with 0–1 $R^9$, phenyl substituted with 0–1 $R^{10}$, and 5–6 membered aromatic heterocycle system containing from 1–4 heteroatoms selected from the group consisting of N, O, and S substituted with 0–1 $R^{10}$.

[3] In a more preferred embodiment, the present invention provides a novel compound of formula I, wherein:

A is O;

$R^1$ is selected from $CF_3$, $CF_2H$, $C_2H_5$, isopropyl, and cyclopropyl;

$R^3$ is selected from H, F, Cl, Br, I, $OCH_3$, and $CH_3$;

$R^4$ is selected from H, F, Cl, Br, I, $C_{1-3}$ alkyl substituted with 0–3 $R^{11}$, $C_{2-3}$ alkenyl, $C_{2-3}$ alkynyl, $C_{1-3}$ alkoxy, $OCF_3$, —CN, $NO_2$, CHO, $C(O)CH_3$, $C(O)CF_3$, $C(O)NH_2$, $C(O)NHCH_3$, $NR^7R^{7a}$, $NR^7C(O)OR^{7b}$, $C(O)OR^7$, $S(O)_pR^7$, $SO_2NHR^7$, $NR^7SO_2R^{7b}$, phenyl, and 5–6 membered aromatic heterocycle system containing from 1–4 heteroatoms selected from the group consisting of N, O, and S;

alternatively, $R^3$ and $R^4$ together form —$OCH_2O$—;

$R^5$ is selected from H and F;

$R^6$ is selected from H, OH, $OCH_3$, —CN, F, $CF_3$, $CH_3$, and $C(O)NH_2$;

$R^7$ is selected from H and $CH_3$;

$R^{7a}$ is selected from H and $CH_3$;

$R^{7b}$ is $CH_3$;

$R^8$ is selected from H, $C_{1-4}$ alkyl substituted with 0–3 $R^{11}$, CH(—$OCH_2CH_2O$—), $C_{2-4}$ alkenyl, $C_{3-5}$ cycloalkyl substituted with 0–1 $R^9$, phenyl substituted with 0–1 $R^{10}$, and 5–6 membered aromatic heterocycle system containing from 1–4 heteroatoms selected from the group consisting of N, O, and S substituted with 0–1 $R^{10}$;

$R^9$ is selected from D, OH, $OCH_3$, $CH_3$, and F;

$R^{10}$ is selected from OH, $CH_3$, $OCH_3$, F, Cl, Br, I, CN, $NR^7R^{7a}$, and $C(O)CH_3$; and, p is selected from 1 and 2.

[4] In an even more preferred embodiment, the present invention provides a novel compound of formula I, wherein:

$R^b$ is selected from H, $CF_3$, $CF_2H$, cyclopropyl, $CH=CH_2$, $CH_3$, and $CH_2CH_3$;

$R^1$ is selected from $CF_3$, $CF_2H$, and cyclopropyl;

$R^2$ is selected from —C≡C—$R^8$ and trans-CH=$CR^7R^8$;

$R^3$ is selected from H, F, Cl, Br, and I;

$R^4$ is selected from H, F, Cl, Br, I, $C_{1-3}$ alkyl substituted with 0–3 $R^{11}$, $CH=CH_2$, C≡CH, $OCH_3$, $OCF_3$, —CN, $NO_2$, CHO, $C(O)CH_3$, $C(O)CF_3$, $C(O)NH_2$, $C(O)NHCH_3$, $NR^7R^{7a}$, $C(O)OR^7$, $NR^7SO_2R^{7b}$, and 5–6 membered aromatic heterocycle system containing from 1–4 heteroatoms selected from the group consisting of N, O, and S;

alternatively, $R^3$ and $R^4$ together form —$OCH_2O$—; and, $R^{11}$ is selected from OH, $OCH_3$, CN, F, Cl, $NR^7R^{7a}$, $C(O)CH_3$, and $C(O)NH_2$.

[5] In a further preferred embodiment, the compound of the present invention is selected from:

5-(1-Butynyl)-7-chloro-1,5-dihydro-5-(trifluoromethyl)-4,1-benzoxazepin-2(3H)-one;

rel-(3S,5S)-5-(1-Butynyl)-7-chloro-1,5-dihydro-3-phenyl-5-(trifluoromethyl)-4,1-benzoxazepin-2(3H)-one;

7-Chloro-1,5-dihydro-5-(isopropylethynyl)-5-(trifluoromethyl)-4,1-benzoxazepin-2(3H)-one;

(+)-(5S)-7-Chloro-1,5-dihydro-5-(isopropylethynyl)-5-(trifluoromethyl)-4,1-benzoxazepin-2(3H)-one;

trans-7-Chloro-5-(2-cyclopropylethenyl)-1,5-dihydro-5-(trifluoromethyl)-4,1-benzoxazepin-2(3H)-one;

rel-(3S,5S)-trans-7-Chloro-5-(2-cyclopropylethenyl)-1,5-dihydro-3-methyl-5-(trifluoromethyl)-4,1-benzoxazepin-2(3H)-one;

1,5-Dihydro-7-fluoro-5-isopropylethynyl-5-(trifluoromethyl)-4,1-benzoxazepin-2(3H)-one;

1,5-Dihydro-7-fluoro-5-(3-methylbutyl)-5-(trifluoromethyl)-4,1-benzoxazepin-2(3H)-one;

rel-(3S,5S)-trans-7-Chloro-1,5-dihydro-5-(2-furan-2-ylethenyl)-3-methyl-5-(trifluoromethyl)-4,1-benzoxazepin-2(3H)-one;

trans-7-Chloro-1,5-dihydro-5-(2-furan-2-yl)ethenyl-5-(trifluoromethyl)-4,1-benzoxazepin-2(3H)-one;

rel-(3S,5S)-7-Chloro-1,5-dihydro-5-(2-furanyl)ethynyl-3-methyl-5-(trifluoromethyl)-4,1-benzoxazepin-2(3H)-one;
5-Butyl-7-chloro-1,5-dihydro-5-(trifluoromethyl)-4,1-benzoxazepin-2(3H)-one;
4-Isopropylethynyl-4-trifluoromethyl-5,6-difluoro-1,4-dihydro-2H-3,1-benzoxazin-2-one.;
rel-(3S,5S)-7-Chloro-5-cyclopropylethynyl-1,5-dihydro-3-propyl-5-(trifluoromethyl)-4,1-benzoxazepin-2(3H)-one;
rel-(3R,5S)-7-Chloro-5-cyclopropylethynyl-1,5-dihydro-3-propyl-5-(trifluoromethyl)-4,1-benzoxazepin-2(3H)-one;
rel-(3S,5S)-7-Chloro-5-cyclopropylethynyl-1,5-dihydro-3-isopropyl-5-(trifluoromethyl)-4,1-benzoxazepin-2(3H)-one;
7-Chloro-5-phenylethynyl-1,5-dihydro-5-(trifluoromethyl)-4,1-benzoxazepin-2(3H)-one;
rel-(3S,5S)-7-Chloro-5-isopropylethynyl-1,5-dihydro-3-methyl-5-(trifluoromethyl)-4,1-benzoxazepin-2(3H)-one;
7-Chloro-5-cyclopropylethynyl-1,5-dihydro-5-(trifluoromethyl)-4,1-benzoxazepin-2(3H)-one;
7-Chloro-5-isopropylethynyl-1,5-dihydro-5-(trifluoromethyl)-4,1-benzoxazepin-2(3H)-one;
trans-7-Chloro-5-(2-isopropylethenyl)-1,5-dihydro-5-(trifluoromethyl)-4,1-benzoxazepin-2(3H)-one;
7-Methoxy-5-(3-methylbutyl)-1,5-dihydro-S-(trifluoromethyl)-4,1-benzoxazepin-2(3H)-one;
rel-(3S,5S)-7-Chloro-5-cyclopropylethynyl-1,5-dihydro-3-ethyl-5-(trifluoromethyl)-4,1-benzoxazepin-2(3H)-one;
rel-(3R,5S)-7-Chloro-5-cyclopropylethynyl-1,5-dihydro-3-ethyl-5-(trifluoromethyl)-4,1-benzoxazepin-2(3H)-one;
7-Chloro-5-(3-pyridylethynyl)-1,5-dihydro-5-(trifluoromethyl)-4,1-benzoxazepin-2(3H)-one;
trans-7-Chloro-5-(3-pyrid-3-ylethenyl)-1,5-dihydro-5-(trifluoromethyl)-4,1-benzoxazepin-2(3H)-one;
trans-7-Fluoro-5-(2-isopropylethenyl)-1,5-dihydro-5-(trifluoromethyl)-4,1-benzoxazepin-2(3H)-one;
trans-6,7-Difluoro-5-(2-isopropylethenyl)-1,5-dihydro-5-(trifluoromethyl)-4,1-benzoxazepin-2(3H)-one;
rel-(3S,5S)-7-Chloro-5-cyclopropylethynyl-1,5-dihydro-3-methyl-5-(trifluoromethyl)-4,1-benzoxazepin-2(3H)-one;
rel-(3S,5S)-trans-7-Chloro-5-(2-cyclopropylethenyl)-1,5-dihydro-3-methyl-5-(trifluoromethyl)-4,1-benzoxazepin-2(3H)-one;
rel-(3S,5S)-trans-7-Chloro-5-(2-cyclopropylethenyl)-1,5-dihydro-3-propyl-5-(trifluoromethyl)-4,1-benzoxazepin-2(3H)-one;
rel-(3S,5S)-7-Chloro-5-(3-furanylethynyl)-1,5-dihydro-3-methyl-5-(trifluoromethyl)-4,1-benzoxazepin-2(3H)-one;
rel-(3S,5S)-7-Chloro-5-(3-furanylethynyl)-1,5-dihydro-3-ethyl-5-(trifluoromethyl)-4,1-benzoxazepin-2(3H)-one;
rel-(3S,5S)-6,7-Difluoro-5-cyclopropylethynyl-1,5-dihydro-3-methyl-5-(trifluoromethyl)-4,1-benzoxazepin-2(3H)-one;
rel-(3S,5S)-6,7-Difluoro-5-cyclopropylethynyl-1,5-dihydro-3-ethyl-5-(trifluoromethyl)-4,1-benzoxazepin-2(3H)-one;
rel-(3S,5S)-trans-6,7-Difluoro-5-(2-cyclopropylethenyl)-1,5-dihydro-3-methyl-5-(trifluoromethyl)-4,1-benzoxazepin-2(3H)-one;
(+)-(3S,5S)-7-Chloro-5-cyclopropylethynyl-1,5-dihydro-3-methyl-5-(trifluoromethyl)-4,1-benzoxazepin-2(3H)-one;
(3S)-7-Chloro-5-cyclopropylethynyl-1,5-dihydro-5-(trifluoromethyl)-4,1-benzoxazepin-2(3H)-one;
rel-(3S,5S)-trans-7-Chloro-5-(2-cyclopropylethenyl)-1,5-dihydro-3-ethyl-5-(trifluoromethyl)-4,1-benzoxazepin-2(3H)-one;
(+)-(3S,5S)-trans-7-Chloro-5-(2-cyclopropylethenyl)-1,5-dihydro-3-methyl-5-(trifluoromethyl)-4,1-benzoxazepin-2(3H)-one;
(+)-(3S,5S)-trans-7-Chloro-5-(2-cyclopropylethenyl)-1,5-dihydro-3-ethyl-5-(trifluoromethyl)-4,1-benzoxazepin-2(3H)-one;
rel-(3S,5S)-7-Chloro-5-(2-cyclopropylethynyl)-1,5-dihydro-3-ethenyl-5-(trifluoromethyl)-4,1-benzoxazepin-2(3H)-one;
rel-(3S,5S)-trans-7-Chloro-5-(2-cyclopropylethenyl)-1,5-dihydro-3-ethenyl-5-(trifluoromethyl)-4,1-benzoxazepin-2(3H)-one;
rel-(3S,5S)-7-Chloro-5-(2-cyclopropylethynyl)-1,5-dihydro-3-cyclopropyl-5-(trifluoromethyl)-4,1-benzoxazepin-2(3H)-one;
rel-(3S,5S)-trans-7-Chloro-5-(2-cyclopropylethenyl)-1,5-dihydro-3-cyclopropyl-5-(trifluoromethyl)-4,1-benzoxazepin-2(3H)-one;
rel-(3S,5S)-6,7-Difluoro-5-(2-cyclopropylethynyl)-1,5-dihydro-3-ethenyl-5-(trifluoromethyl)-4,1-benzoxazepin-2(3H)-one;
rel-(3S,5S)-6,7-Difluoro-5-(2-cyclopropylethynyl)-1,5-dihydro-3-cyclopropyl-5-(trifluoromethyl)-4,1-benzoxazepin-2(3H)-one;
rel-(3S,5S)-7-Fluoro-5-(2-cyclopropylethynyl)-1,5-dihydro-3-ethenyl-5-(trifluoromethyl)-4,1-benzoxazepin-2(3H)-one;
rel-(3S,5S)-7-Fluoro-5-(2-cyclopropylethynyl)-1,5-dihydro-3-methyl-5-(trifluoromethyl)-4,1-benzoxazepin-2(3H)-one;
rel-(3S,5S)-7-Fluoro-5-(2-cyclopropylethynyl)-1,5-dihydro-3-ethyl-5-(trifluoromethyl)-4,1-benzoxazepin-2(3H)-one;
rel-(3S,5S)-trans-7-Fluoro-5-(2-cyclopropylethenyl)-1,5-dihydro-3-methyl-5-(trifluoromethyl)-4,1-benzoxazepin-2(3H)-one;
rel-(3S,5S)-trans-7-Fluoro-5-(2-cyclopropylethenyl)-1,5-dihydro-3-ethyl-5-(trifluoromethyl)-4,1-benzoxazepin-2(3H)-one;
rel-(3S,5S)-6,7-Methylenedioxy-5-(2-cyclopropylethynyl)-1,5-dihydro-3-methyl-5-(trifluoromethyl)-4,1-benzoxazepin-2(3H)-one;
rel-(3S,5S)-6,7-Methylenedioxy-5-(2-cyclopropylethynyl)-1,5-dihydro-3-ethyl-5-(trifluoromethyl)-4,1-benzoxazepin-2(3H)-one;
rel-(3S,5S)-trans-6,7-Methylenedioxy-5-(2-cyclopropylethenyl)-1,5-dihydro-3-methyl-5-(trifluoromethyl)-4,1-benzoxazepin-2(3H)-one; and,
rel-(3S,5S)-trans-6,7-Methylenedioxy-5-(2-cyclopropylethenyl)-1,5-dihydro-3-ethyl-5-(trifluoromethyl)-4,1-benzoxazepin-2(3H)-one;

or a pharmaceutically acceptable salt form thereof.

[6] In another preferred embodiment, the present invention provides a compound of formula II:

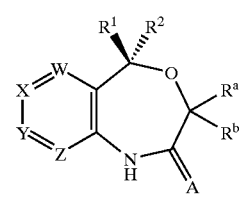

or a stereoisomer or pharmaceutically acceptable salt form thereof.

[7] In another more preferred embodiment, the present invention provides a compound of formula IIa:

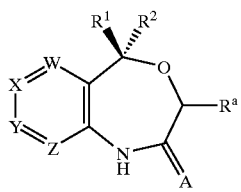

or a stereoisomer or pharmaceutically acceptable salt form thereof, wherein $R^1$ is $CF_3$.

In a second embodiment, the present invention provides a novel pharmaceutical composition comprising a pharmaceutically acceptable carrier and a therapeutically effective amount of a compound of formula I or pharmaceutically acceptable salt form thereof.

In a third embodiment, the present invention provides a novel method for treating HIV infection which comprises administering to a host in need of such treatment a therapeutically effective amount of a compound of formula I or pharmaceutically acceptable salt form thereof.

In a fourth embodiment, the present invention provides a novel method of treating HIV infection which comprises administering, in combination, to a host in need thereof a therapeutically effective amount of:

(a) a compound of formula I; and,
(b) at least one compound selected from the group consisting of HIV reverse transcriptase inhibitors and HIV protease inhibitors.

In another preferred embodiment, the reverse transcriptase inhibitor is a nucleoside reverse transcriptase inhibitor.

In another more preferred embodiment, the nucleoside reverse transcriptase inhibitor is selected from AZT, 3TC, rescriptor, ddI, ddC, efavirenz, and d4T and the protease inhibitor is selected from saquinavir, ritonavir, indinavir, VX-478, nelfinavir, KNI-272, CGP-61755, and U-103017.

In an even more preferred embodiment, the nucleoside reverse transcriptase inhibitor is selected from AZT, efavirenz, rescriptor, and 3TC and the protease inhibitor is selected from saquinavir, ritonavir, indinavir, and nelfinavir.

In a still further preferred embodiment, the nucleoside reverse transcriptase inhibitor is AZT.

In another still further preferred embodiment, the protease inhibitor is indinavir.

In a fifth embodiment, the present invention provides a pharmaceutical kit useful for the treatment of HIV infection, which comprises a therapeutically effective amount of:

(a) a compound of formula I; and,
(b) at least one compound selected from the group consisting of HIV reverse transcriptase inhibitors and HIV protease inhibitors, in one or more sterile containers.

In a sixth embodiment, the present invention provides a novel method of inhibiting HIV present in a body fluid sample which comprises treating the body fluid sample with an effective amount of a compound of formula I.

In a seventh embodiment, the present invention to provides a novel a kit or container comprising a compound of formula (I) in an amount effective for use as a standard or reagent in a test or assay for determining the ability of a potential pharmaceutical to inhibit HIV reverse transcriptase, HIV growth, or both.

Definitions

As used herein, the following terms and expressions have the indicated meanings. It will be appreciated that the compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

The processes of the present invention are contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl"is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. Alkenyl" is intended to include hydrocarbon chains of either a straight or branched configuration and one or more unsaturated carbon-carbon bonds which may occur in any stable point along the chain, such as ethenyl and propenyl. "Alkynyl" is intended to include hydrocarbon chains of either a straight or branched configuration and one or more triple carbon-carbon bonds which may occur in any stable point along the chain, such as ethynyl and propynyl.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "aryl" or "aromatic residue" is intended to mean an aromatic moiety containing the specified number of carbon atoms, such as phenyl or naphthyl. As used herein, "carbocycle" or "carbocyclic residue" is intended to mean any stable 3- to 7-membered monocyclic or bicyclic which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic system" is intended to mean a stable 5- to 6-membered monocyclic heterocyclic ring which is saturated partially unsaturated or unsaturated (aromatic), and which consists of carbon atoms and from 1 to 3 heteroatoms independently selected from the group consisting of N, O and S. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be guaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 6-membered monocyclic heterocyclic aromatic ring which consists of carbon atoms and from 1 to 3 heterotams independently selected from the group consisting of N, O and S. It is preferred that the total number of S and O atoms in the aromatic heterocycle is not more than 1.

Examples of heterocycles include, but are not limited to, 2-pyrrolidonyl, 2H-pyrrolyl, 4-piperidonyl, 6H-1,2,5-thiadiazinyl, 2H,6H-1,5,2-dithiazinyl, furanyl, furazanyl, imidazolidinyl, imidazolinyl, imidazolyl, isoxazolyl, morpholinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, piperazinyl, piperidinyl, pteridinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, tetrahydrofuranyl, 6H-1,2,5-thiadiazinyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, and 1,3,4-triazolyl. Preferred heterocycles include, but are not limited to, pyridinyl, furanyl, thienyl, pyrrolyl, pyrazolyl, imidazolyl, and oxazolidinyl. Also included are fused ring and spiro compounds containing, for example, the above heterocycles.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, and 3TC. Examples of non-nucleoside RT inhibitors include, but are not limited to, efavirenz (DuPont), rescriptor (delavirdine, Pharmacia and Upjohn), viviradine (Pharmacia and Upjohn U90152S), TIBO derivatives, BI-RG-587, nevirapine, L-697, 661, LY 73497, and Ro 18,893 (Roche).

As used herein, "HIV protease inhibitor" is intended to refer to compounds which inhibit HIV protease. Examples include, but are not limited, saquinavir (Roche, Ro31-8959), ritonavir (Abbott, ABT-538), indinavir (Merck, MK-639), VX-478 (Vertex/Glaxo Wellcome), nelfinavir (Agouron, AG-1343), KNI-272 (Japan Energy), CGP-61755 (Ciba-Geigy), DMP450 (DuPont), DMP850 (DuPont), DMP851 (DuPont) and U-103017 (Pharmacia and Upjohn). Additional examples include the cyclic protease inhibitors disclosed in WO93/07128, WO94/19329, WO94/22840, and PCT Application Number US96/03426 and the protease inhibitors disclosed in WO94/04993,WO95/33464, WO96/28,418, and WO96/28,464.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa, 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Prodrugs" are intended to include any covalently bonded carriers which release the active parent drug according to formula (I) or other formulas or compounds of the present invention in vivo when such prodrug is administered to a mammalian subject. Prodrugs of a compound of the present invention, for example formula (I), are prepared by modifying functional groups present in the compound in such a way that the modifications are cleaved, either in routine manipulation or in vivo, to the parent compound. Prodrugs include compounds of the present invention wherein the hydroxy or amino group is bonded to any group that, when the prodrug is administered to a mammalian subject, cleaves to form a free hydroxyl or free amino, respectively. Examples of prodrugs include, but are not limited to, acetate, formate and benzoate derivatives of alcohol and amine functional groups in the compounds of the present invention, and the like.

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

"Therapeutically effective amount" is intended to include an amount of a compound of the present invention or an amount of the combination of compounds claimed effective to inhibit HIV infection or treat the symptoms of HIV infection in a host. The combination of compounds is preferably a synergistic combination. Synergy, as described for example by Chou and Talalay, Adv. Enzyme Regul. 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Each of the references cited below are hereby incorporated herein by reference.

SCHEME 1

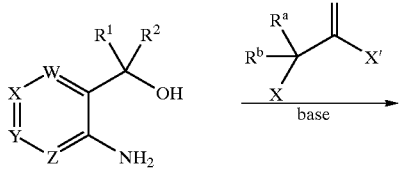

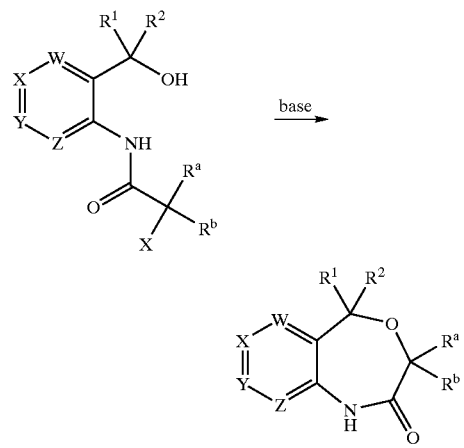

Scheme 1 illustrates a method of making the oxazepinones of the present invention starting from an appropriately substituted aminoalcohol. The amine is acylated by an α-halo acid halide (preferably an α-bromoacyl bromide) in the presence of a weak base such as pyridine. After acylation, cyclization is effected by further treatment with base. A tertiary amine base such as diisopropylethylamine, sodium hydride, potassium hydride, lithium hydride, sodium carbonate, potassium carbonate or cesium carbonate, sodium or potassium alkoxides or similar bases may be used with cesium carbonate and sodium hydride being preferred. Any non-protic organic solvent may be used for the cyclization reaction with DMF being preferred. In cases where $R^1$ and $R^2$ are different and $R^a$ and $R^b$ are also different, two diastereomers are formed which may be separated by selective crystallization or chromatography. In the case where $R^1$ and $R^2$ are different and either $R^a$ or $R^b$ is H, cyclization with cesium carbonate in the presence of lithium bromide or lithium iodide will often afford a diastereomeric mixture in which one diastereomer greatly predominates. Thus, in some cases these cyclization conditions are greatly preferred. In cases where both $R^a$ and $R^b$ are H, either sodium hydride or cesium carbonate are preferred bases. When an appropriately strong base is used, both acylation and cyclization reactions illustrated in Scheme 1 may be effected in a single step.

SCHEME 2

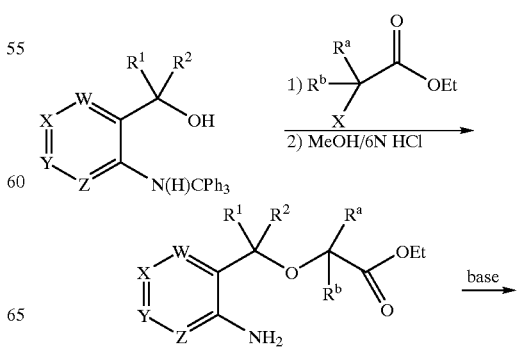

-continued

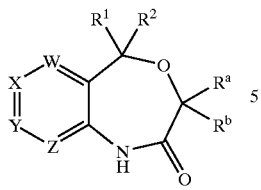

Scheme 2 illustrates a second method of making the oxazepinones of the present invention starting from an appropriately substituted N-tritylaminoalcohol. The hydroxy group is alkylated with an α-haloester in the presence of base, and then after removal of the trityl protecting group, treatment with base and/or heat effects cyclization to the oxazepinone. In some cases it may be preferable to use an unprotected amino group. Also, other protecting groups known to those of skill in the art can be used in place of the shown trityl group.

SCHEME 3

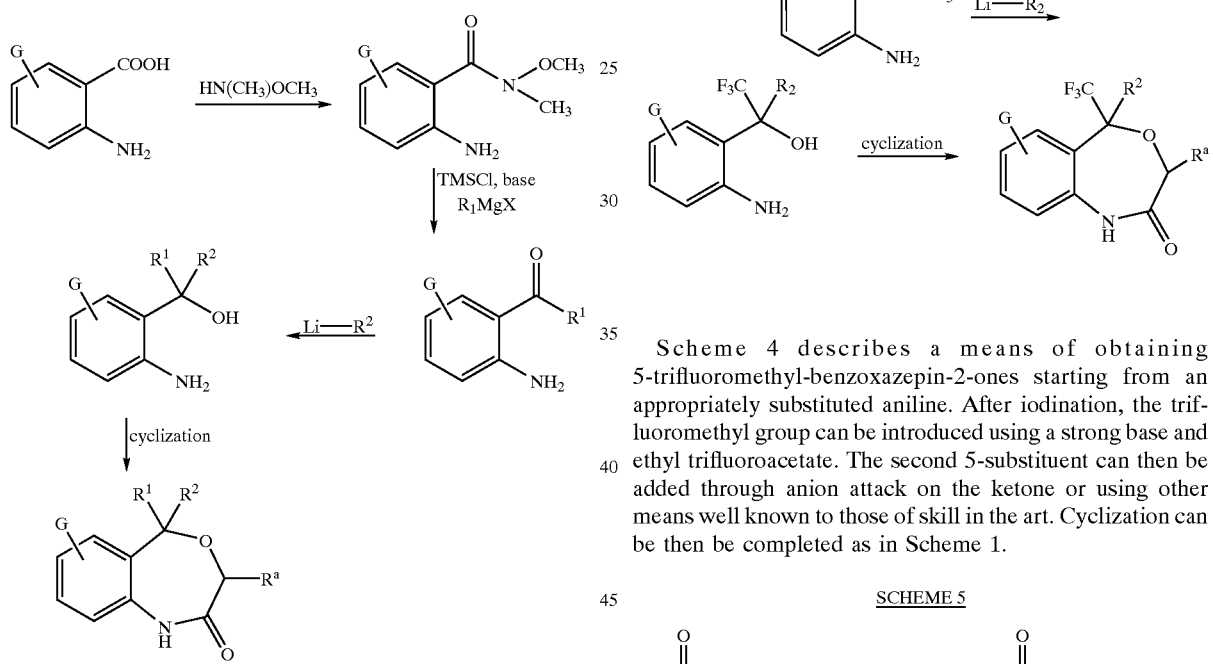

Scheme 3 illustrates a method of making 5,5-disubstituted-benzoxazepin-2-ones starting from an appropriately substituted 2-aminobenzoic acid. In Scheme 3, G can be $R^3$, $R^4$, $R^5$ or $R^6$ or a combination of two or more of these groups. The acid is converted to its N-methoxy-N-methyl amide derivative which can then be displaced to obtain the $R^1$-substituted ketone. Subsequent addition of another metallic species provides the alcohol which is readily cyclized by the 2-step procedure described in Scheme 1.

SCHEME 4

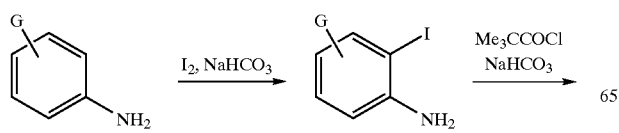

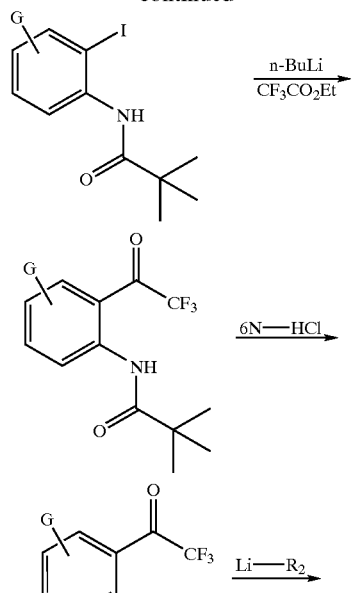

Scheme 4 describes a means of obtaining 5-trifluoromethyl-benzoxazepin-2-ones starting from an appropriately substituted aniline. After iodination, the trifluoromethyl group can be introduced using a strong base and ethyl trifluoroacetate. The second 5-substituent can then be added through anion attack on the ketone or using other means well known to those of skill in the art. Cyclization can be then be completed as in Scheme 1.

SCHEME 5

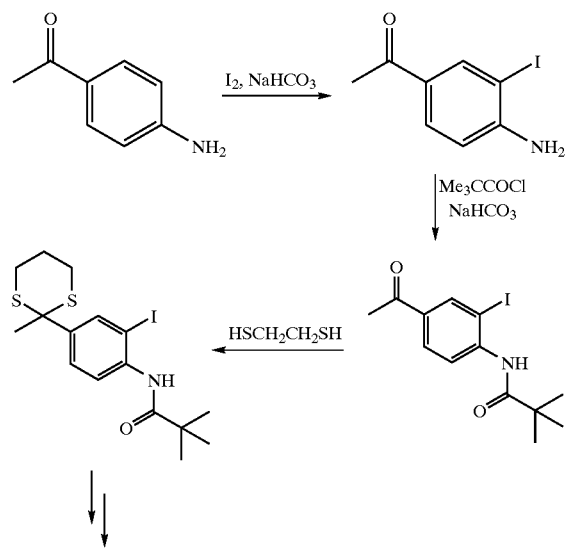

-continued

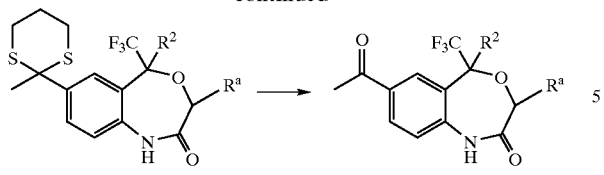

Because certain benzo-substituents are incompatible with the methods of the previous schemes, it may be necessary to protect these groups before forming the benzoxazepinone. In Scheme 5 there is shown a means of obtaining carbonyl-substituted 5,5-disubstituted-benzoxazepin-2-ones. After iodination of an acetyl-aniline, the acetyl group is protected by means well known to those of skill in the art, such as using 1,3-propanedithiol. The same procedures as in Scheme 4 are used to arrive at the cyclized product. Deprotection of the ketone can then be achieved using $HgCl_2$ and HgO or other means well known to those of skill in the art.

agent, such as $LiAlH_4$, deprotection by standard means, and 2-step cyclization.

SCHEME 6A

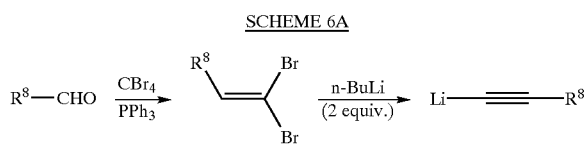

The acetylide which is required for the reactions illustrated in Scheme 6 may be generated directly from a terminal acetylene by treatment with a strong base such as n-butyllithium. An alternate method for generating an acetylide, illustrated in Scheme 6A, is by converting an aldehyde to a 1,1-dibromoolefin which is then reacted with 2 equivalents of n-butyllithium.

SCHEME 6

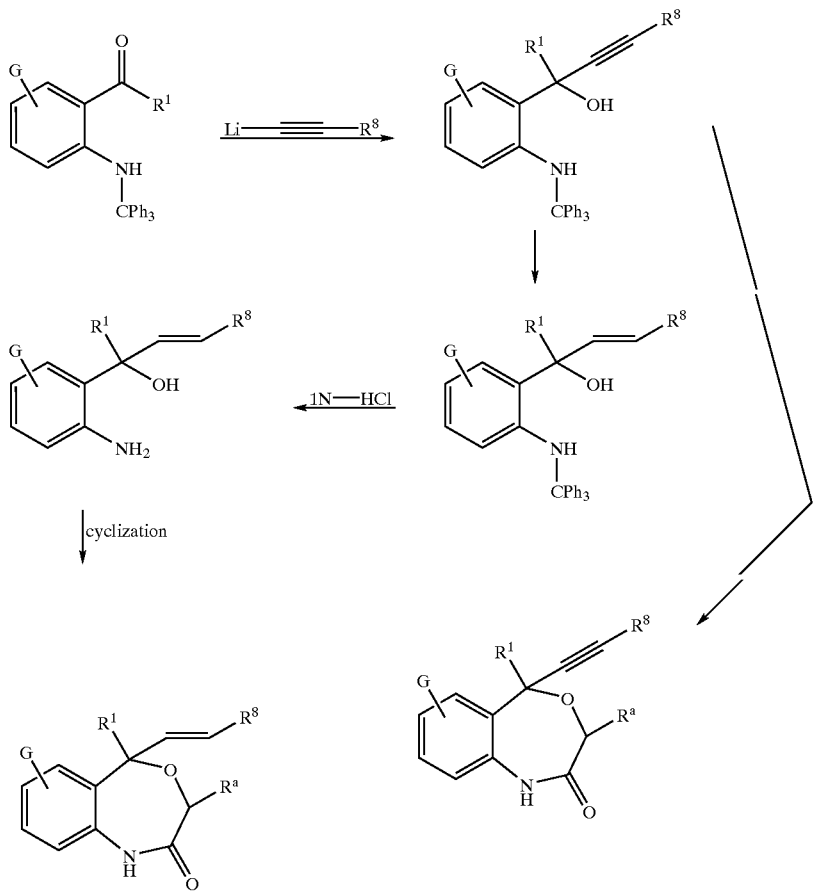

A method for forming 5,5-disubstituted-benzoxazepin-2-ones, wherein $R^2$ is a vinyl or alkynyl group, is described in Scheme 6. Starting from an appropriately substituted ketone which can be obtained using the procedure of Scheme 3 or 4, an acetylide is added. The product can be deprotected and cyclized in two steps (Scheme 1) to obtain the alkynyl-substituted material. Alternatively, the vinyl compounds can be obtained by reduction of the alkyne with a reducing

SCHEME 7

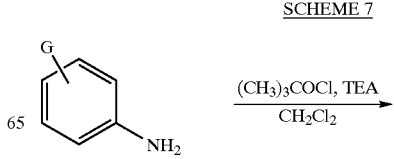

-continued

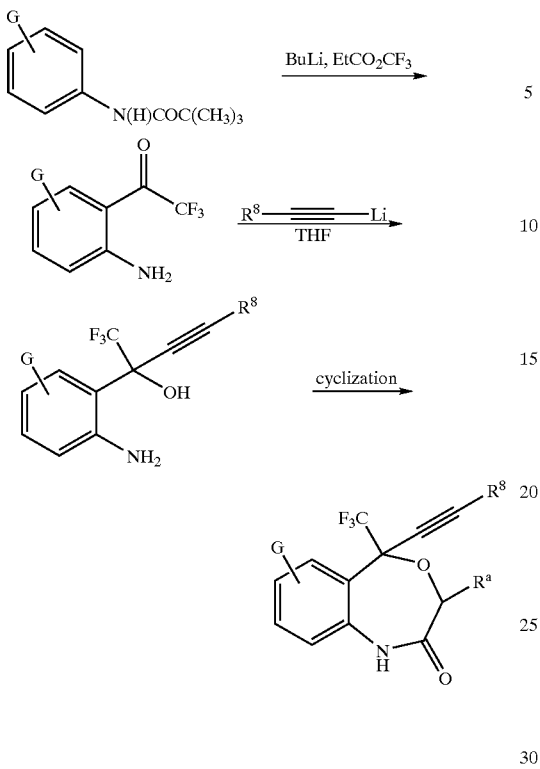

Scheme 7 describes an alternate route to 5,5-disubstituted-benzoxazepin-2-ones from anilines, wherein the aniline is protected, ester addition is accomplished using a strong base and the amine protecting group is removed. The $R^2$ group can then be added, e.g. via an acetylide, followed by cyclization as in Scheme 1.

SCHEME 8

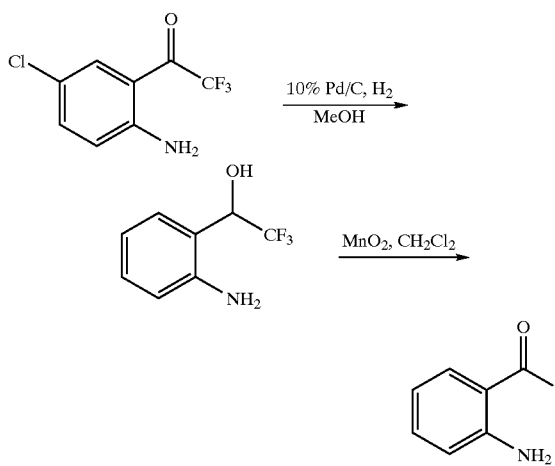

An intermediate useful in the preparation of the presently claimed compounds is 2-trifluoroacetylaniline. The starting 4-chloro-2-trifluoroacetylaniline can be made as shown in Scheme 4. Reduction and reoxidation removes the chloro group leaving the desired intermediate.

SCHEME 9

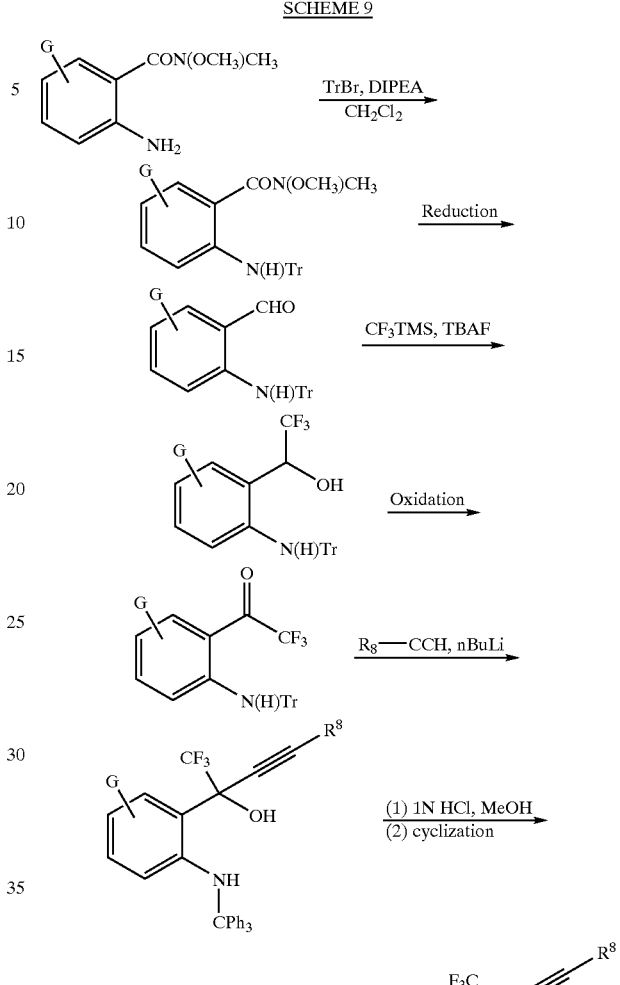

Scheme 9 describes a novel method of making 2-trifluoroacetylanilines as well as how these compounds can be further modified to make the presently claimed compounds. The protected aldehyde can be made from the N-methoxy-N-methyl amide of Scheme 3, by addition of a protecting group, preferably trityl, and reduction of the amide to the aldehyde. Other protecting groups known to those of skill in the art can be used in place of the shown trityl group.

SCHEME 10

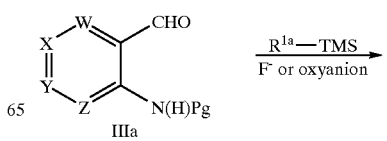

IIIa

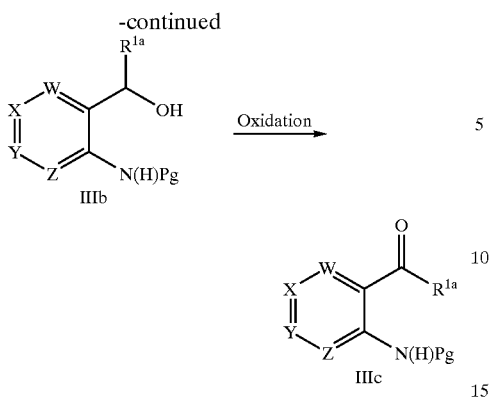

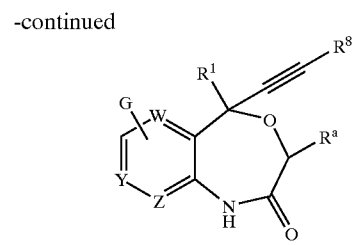

Scheme 10 illustrates specific steps of Scheme 9. Intermediate IIIb ($R^{1a}$ is selected from $CF_3$, $CF_3CF_2$, and $CF_3CF_2CF_2$) is useful for making some of the presently claimed compounds. Pg is an amine protecting group as defined previously, preferably trityl (triphenylmethyl). The protected or unprotected aminobenzaldehyde, preferably protected, is treated with a perfluoralkyl trimethylsilane, preferably trifluoromethyl trimethylsilane, followed by fluoride anion, preferably tetrabutylammonium fluoride. In the same fashion, $CF_3CF_2TMS$, $CF_3CF_2CF_2TMS$ can also be used to prepare the appropriately substituted ketones. Other sources of fluoride anion such as sodium fluoride, potassium fluoride, lithium fluoride, cesium fluoride as well as oxyanionic species such as potassium tert-butoxide, sodium methoxide, sodium ethoxide and sodium trimethylsilanolate can also be used. Aprotic solvents such as DMF and THF can be used, preferably THF. The amount of perfluoralkyl trimethylsilane used can be from about 1 to about 3 equivalents with an equivalent amount of fluoride anion or oxyanionic species. The reaction can be typically carried out at temperatures between about −20° C. to about 50° C., preferably about −10 to about 10° C., more preferably about 0° C.

Conversion of IIIb to IIIc can be achieved by using an oxidizing agent well known to one of skill in the art such as $MnO_2$, PDC, PCC, $K_2Cr_2O_7$, $CrO_3$, $KMnO_4$, $BaMnO_4$, $Pb(OAc)_4$, and $RuO_4$. A preferred oxidant is $MnO_2$. Such conversion can be performed in an aprotic solvent like THF, DMF, dichloromethane, dichloroethane, or tetrachloroethane, preferably dichloromethane.

SCHEME 11

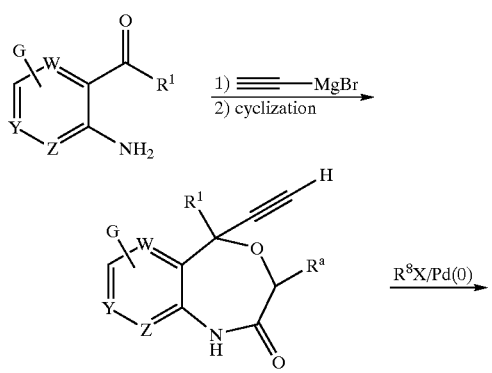

An additional means of making 5-alkynyl-benzoxazepin-2-ones is shown in Scheme 11. The alkyne group is added to the keto-aniline via a Grignard type addition, followed by cyclization. The alkyne group of the product can then be modified to obtain the desired compound.

SCHEME 12

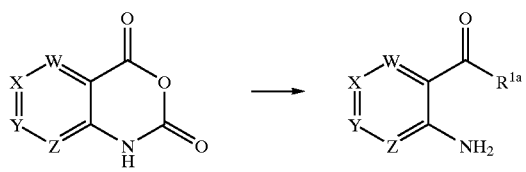

In addition to the methods of obtaining keto-anilines described in Schemes 3 and 4, nucleophilic opening of isatoic anhydrides can also be used as shown in Scheme 12. This reaction is accomplished by using an anionic nucleophile of the group $R^{1a}$. See Mack et al, *J. Heterocyclic Chem.* 1987, 24, 1733–1739; Coppola et al, *J. Org. Chem.* 1976, 41(6), 825–831; Takimoto et al, *Fukuoka Univ. Sci. Reports* 1985, 15(1), 37–38; Kadin et al, *Synthesis* 1977, 500–501; Staiger et al, *J. Org. Chem.* 1959, 24, 1214–1219.

It is preferred that the stoichiometry of the isatoic anhydride reagent to nucleophile is about 1.0 to 2.1 molar equivalents. The use of 1.0 eq. or more (e.g., 1.1, 1.2, 1.3, 1.4, 1.5, 1.6, 1.7, 1.8, 1.9, or 2.0) of anion (or anion precursor) is preferred to force the conversion and improve the isolated yield. Preferably, the temperature used is from −20 to +35° C., with temperatures below 0° C. being more preferred and −20° C. being even more preferred. Reactions are run to about completion with time dependent upon inter alia nucleophile, solvent, and temperature. Preferably this nucleophilic addition is run in THF, but any aprotic solvent would be suitable. Reaction with the active nucleophilic anion is the only criterion for exclusion of a solvent.

SCHEME 13

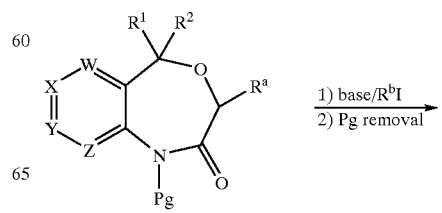

SCHEME 14

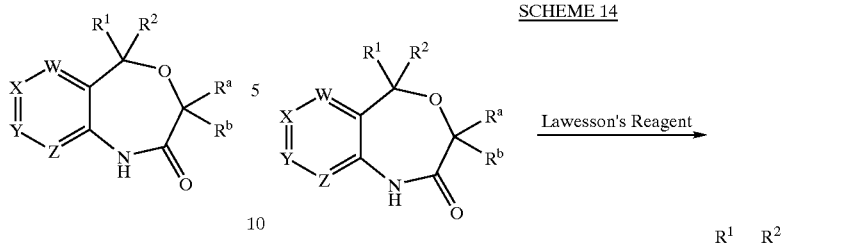

Scheme 13 illustrates the synthesis of a 3,3-disubstituted oxazepinone from a monosubstituted oxazepinone. After first protecting the ring nitrogen with one of several amide protecting groups known to those skilled in the art, treatment with a strong base followed by an alkyl iodide gives after protecting group removal, a 3,3-disubstituted oxazepinone. Using the same sequence of reactions, a 3-monosubstituted oxazepinone ($R^a$ above is H) can also be synthesized from a 3-unsubstituted oxazepinone.

Compounds of the present invention that are thioamides can be prepared as illustrated in Scheme 14 by treating the corresponding amides with either Lawesson's reagent [2,4-bis(4-methoxyphenyl)-1,3-dithia-2,4-diphosphetane-2,4-disulfide] or phosphorous pentasulfide.

SCHEME 15

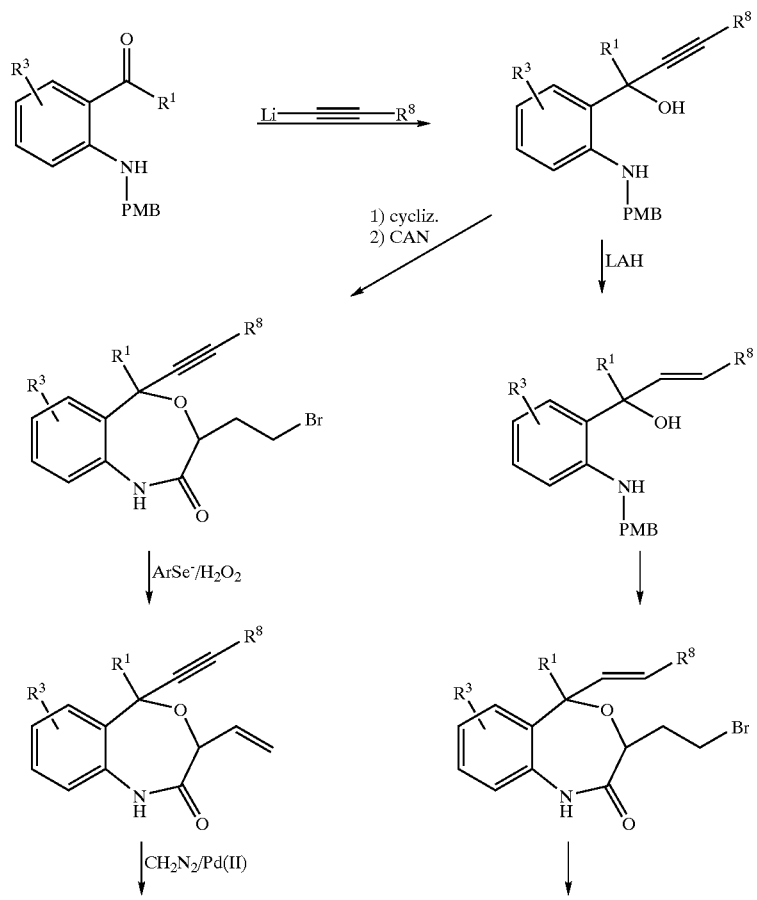

-continued

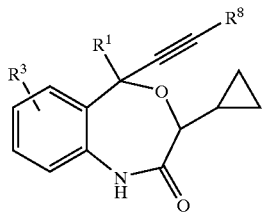 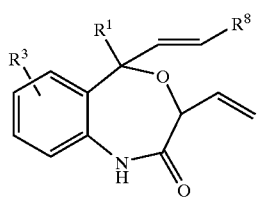

Compounds of the present invention in which $R^a$ or $R^b$ are vinyl or cyclopropyl can be prepared as illustrated in Scheme 15. 2-Aminoarylketones protected, for example, with an N-p-methoxybenzyl (PMB) group can be treated with an acetylide to give the corresponding acetylenic alcohol. Cyclization can be effected by 2,4-dibromobutyryl chloride and the PMB group can then be removed, for example, by treatment with ceric am monium nitrate. Displacement of the bromide with an arylselenide followed by oxidative elimination by treatment with hydrogen peroxide affords the 5-alkynyl-3-vinylbenzoxazepinone. The vinyl group can be converted to a cyclopropane ring by Pd(II) catalyzed reaction with diazomethane. If the acetylenic alcohol is reduced to the olefin with lithium aluminum hydride (LAH), the same reaction sequence can be used to prepare the trans-5-alkenyl-3-vinylbenzoxazepinone and the corresponding trans-5-alkenyl-3-cyclopropylbenzoxazepinone.

One isomer of a compound of Formula I may display superior activity compared with the other. Thus, all four of the following stereochemistries are considered to be a part of the present invention.

Ia
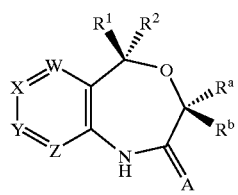

Ib
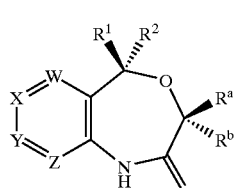

Ic
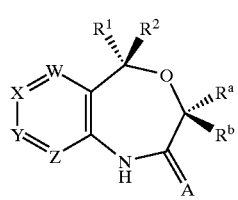

Id
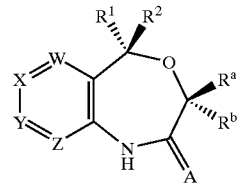

When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602–2605. A chiral compound of Formula I may also be directly synthesized using a chiral catalyst or a chiral ligand, e.g., Andrew S. Thompson, et al, *Tet. Lett.* 1995, 36, 8937–8940. In addition, separation may be achieved by selective cystallization, optionally in the presence of a chiral acid or base thereby forming a chiral salt. other features of the invention will become apparent in the course of the following descriptions of exemplary embodiments which are given for illustration of the invention and are not intended to be limiting thereof.

EXAMPLES

Abbreviations used in the Examples are defined as follows: anal. for combustion analysis, "g" for gram or grams, HRMS for high resolution mass spectrometry, "mg" for milligram or milligrams, "mL" for milliliter or milliliters, "mmol" for millimole or millimoles, "h" for hour or hours, "HPLC" for high performance liquid chromatography, "M" for molar, "min" for minute or minutes, "MHz" for megahertz, "MS" for mass spectroscopy, "TLC" for thin layer chromatography.

For further clarification of the stereochemistry, in compounds with stereochemistry designated as "rel-(3S,5S)" the 3-substituent is cis to the 5-trifluoromethyl group while in compounds with stereochemistry designated as "rel-(3R,5S)" the 3-substituent is trans to the 5-trifluoromethyl group.

Example 1

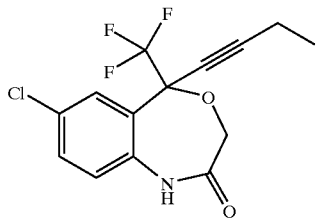

Preparation of 5-(1-Butynyl)-7-chloro-1,5-dihydro-5 (trifluoromethyl)-4,1-benzoxazepin-2(3H)-one Part A: Preparation of 1-(5-Chloro-2triphenylmethylanino)phenyl-2,2,2-trifluoroethanone 1-(2-Amino-5-chlorophenyl)-2,2,2-trifluoroethanone (see U.S. Pat. No. 5,519,021)(22.4 g, 100 mmol), trityl chloride (30.0 g, 107 mmol), triethylamine (11.6 g, 115 mmol) and 4-(dimethylamino)pyridine (0.5 g, 4 mmol) were dissolved in DMF (50 mL) and held 14 h at 60° C. The resulting slurry was cooled to room temperature, diluted with 20 mL water and filtered to give 35.9 g (77%) of the title compound.

Part B: Preparation of 6-Amino-3-chloro-α-(1-butynyl)-α-(trifluoromethyl)benzyl alcohol To a −30° solution of 1.4 g of 1-butyne in 30 mL of dry THF was added dropwise over S min, 7.5 mL of a 1.6 M solution of n-butyllithium in hexane. The reaction mixture was allowed to warm to 0° and then stirred at this temperature for 30 min after which time 1.4 g of 1-(5-chloro-2-triphenylmethylamino)phenyl-2,2,2-trifluoroethanone was added in one portion. The reaction mixture was stirred at 0° for 30 min after which time it was quenched with saturated aqueous ammonium chloride and poured onto water. This mixture was extracted twice with ether and the combined extracts were washed with brine dried and evaporated to a pure solid. This material was was dissolved in 20 mL of methanol and treated with 0.370 mL of 12 N aqueous hydrochloric acid for 15 min. The reaction mixture was partitioned between water and ether, and the ether layer was washed with aqueous bicarbonate, brine, dried and evaporated. The residue was dissolved in methanol and after cooling in ice for 1 h, the precipitated methyl trityl ether was filtered off. After evaporation of the filtrate, crystallization from hexanes afforded 675 mg of the title compound as a crystalline solid.

Part C: Preparation of 5-(1-Butynyl)-7-chloro-1,5-dihydro-5-(trifluoromethyl)-4,1-benzoxazepin-2(3H)-one To a stirred ice-cooled solution of 167 mg of 6-amino-3-chloro-α-(1-butynyl)-α-(trifluoromethyl)benzyl alcohol in 15 mL of dry ether was added 0.100 mL of dry pyridine and 0.066 mL of bromoacetyl bromide. After 30 min, the reaction mixture was diluted with ether, washed with water and aqueous sodium bicarbonate, dried and evaporated. The residue was dissolved in 15 mL of dry DMF and was treated at room temperature with 25 mg of 100% sodium hydride for 1.5 h. The reaction was partitioned between ethyl acetate and water and the ethyl acetate layer was washed with brine, dried and evaporated. The crude product was purified by preparative silica gel TLC (elution with ethyl acetate/hexanes 1:2) affording after crystallization from ethyl acetate/hexanes 106 mg of the title compound as colorless crystals: mp 167–168°; Anal. Calcd. for $C_{14}H_{11}NO_2ClF_3$: C, 52.93; H, 3.49; N, 4.42. Found: C, 52.73; H, 3.64; N, 4.13.

Example 2

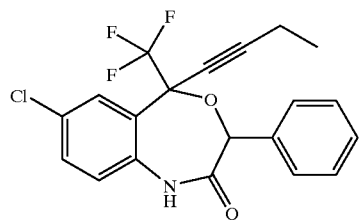

Preparation of rel-(3S,5S)-5-(1-Butynyl)-7-chloro-1,5-dihydro-3-phenyl-5-(trifluormethyl)-4,1-benzoxazepin-2(3H)-one To a stirred ice-cooled solution of 278 mg of 6-amino-3-chloro-α-(1-butynyl)-α-(trifluoromethyl)benzyl alcohol (Example 1, Part B) in 25 mL of dry ether was added 0.150 mL of dry pyridine and 0.200 mL of α-chlorophenacetyl bromide. After 30 min, the reaction mixture was diluted with ether, washed with water and aqueous sodium bicarbonate, dried and evaporated. The residue was dissolved in 15 mL of dry DMF, 50 mg of potassium iodide and 28 mg of 100% sodium hydride were added and this solution was heated at 60° for 12 h. The reaction was partitioned between ethyl acetate and water and the ethyl acetate layer was washed with brine, dried and evaporated. The crude product was subjected to column chromatography over silica gel (elution with ethyl acetate/hexanes 1:3) affording a mixture of diastereomers. These were separated by column chromatography over silica gel (elution with 1% methanol in methylene chloride) and the less polar isomer (27 mg) was crystallized from hexane to give 13 mg of the title compound as colorless crystals: mp 198–199°; HRMS Calcd. for $C_{20}H_{16}NO_2CF_3$ (M+H)$^+$: 394.082166. Found: 394.080316.

Example 3

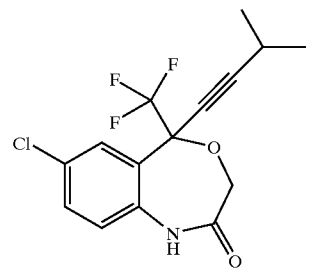

Preparation of 7-Chloro-1,5-dihydro-5-(isopropylethynyl)-5-(trifluoromethyl)-4,1-benzoxazepin-2(3H)-one Part A: Preparation of 6-Amino-3-chloro-α-(isopropylethynyl)-α-(trifluoromethyl)benzyl alcohol To an ice-cooled solution of 3.06 g (45 mmol) of isopropylacetylene in 90 mL of dry THF was added dropwise over 5 min, 25 mL of a 1.6 M solution of n-butyllithium in hexane (40 mmol). After 30 min at 0°, a solution of 9.3 g of 1-(5-chloro-2-triphenylmethylamino)phenyl-2,2,2-trifluoroethanone (Example 1, Part A) in 40 mL of dry THF was added dropwise over 5 min. The reaction mixture was stirred at 0° for 15 min after which time it was quenched with saturated aqueous ammonium chloride and poured onto water. This mixture was extracted twice with ether and the combined extracts were washed with brine, dried, and evaporated to a pure solid. This material was was dissolved in 100 mL of methanol and treated with 2.0 mL of 12 N aqueous hydrochloric acid for 15 min. The reaction mixture was partitioned between water and ether, and the ether layer was washed with aqueous bicarbonate, brine, dried, and evaporated. The residue was dissolved in 200 mL of methanol and after cooling in ice for 1 h, the precipitated methyl trityl ether was filtered off. After evaporation of the filtrate, crystallization from 80 mL of hexanes afforded 4.40 g (75.4%) of the title compound as a crystalline solid.

Part B: Preparation of 7-Chloro-1,5-dihydro-5-(isopropylethynyl)-5-(trifluoromethyl)-4,1-benzoxazepin-2(3H)-one To a stirred ice-cooled solution of 4.37 g (15 mmol) of 6-amino-3-chloro-α-(isopropylethynyl)-α-(trifluoromethyl) benzyl alcohol in 200 mL of dry ether was added 2.4 mL of dry pyridine and, quickly dropwise, 1.40 mL (16 mmol) of bromoacetyl bromide. After 30 min, the reaction mixture was diluted with ether, washed with water and aqueous sodium bicarbonate, dried and evaporated. The residue was dissolved in 150 mL of dry DMF and was treated at 0° with 400 mg of 100% sodium hydride (16.7 mmol) for 20 min. The cooling bath was removed, and the reaction was allowed to proceed at ambient temperature for 1.5 h. The reaction mixture was poured onto a mixture of 1.2 L of water and 300 mL of saturated aqueous sodium chloride and this was extracted 3 times with ether. The combined extracts were washed with brine, dried, and evaporated to a solid which was crystallized by dissolving in hot ethyl acetate and adding hexanes. This material was recrystallized from ethyl acetate/hexane to afford 3.125 g of pure title compound as a crystalline solid: mp 183–183.5°; HRMS Calcd. for $C_{15}H_{14}NO_2ClF_3$ (M+H)$^+$: 332.066516. Found: 332.065892.

Example 4

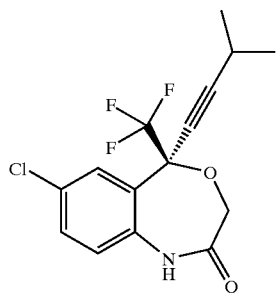

Preparation of (+)-(5S)-7-Chloro-1,5-dihydro-5-(isopropylethynyl)-5-(trifluoromethyl)-4,1-benzoxazepin-2(3H)-one The racemic material from Example 3, Part B above was separated by preparative HPLC on a Chiralcel column maintained at ambient temperature with elution with 10% isopropylamine in carbon dioxide at a pressure of 150 Atm. and a flow rate of 2.0 mL/min. The slower moving isomer was collected and crystallized from hexane: mp 135–136°; [α]$^{25}$+9.69°.

Example 5

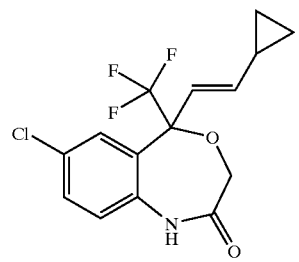

Preparation of trans-7-Chloro-5-(2-cyclopropylethenyl)-1,5-dihydro-5-(trifluoromethyl)-4,1-benzoxazepin-2(3H)-one

Part A: Preparation of 3-Chloro-6-(triphenylmethyl) amino-α-cyclopropylethynyl-α-(trifluoromethyl) benzyl alcohol To an ice-cooled solution of 4.5 g (67.55 mmol) of cyclopropylacetylene in 130 mL of dry THF was added dropwise over 5 min, 37.5 mL (60 mmol) of 1.6 M n-butyllithium. The reaction mixture was allowed to warm to 0° over 30 min after which time a solution of 13.95 g (30.0 mmol) of 1-(5-chloro-2-triphenylmethylamino)phenyl-2,2,2-trifluoroethanone (Example 1, Part A) in 50 mL of dry THF was added dropwise over 5 min. The reaction mixture was stirred at 0° for 30 min after which time it was quenched with saturated aqueous ammonium chloride and poured onto water. This mixture was extracted twice with ether and the combined extracts were washed with brine dried and evaporated to pure title compound as a glassy solid.

Part B: Preparation of trans-6-Amino-3-chloro-α-(2-cyclopropylethenyl)-α-(trifluoromethyl)benzyl alcohol The reaction product from part A was dissolved in 100 mL of dry THF and treated overnight with 20 mL of a 1 M solution of lithium aluminum hydride in THF. At this time TLC showed incomplete reaction so an aditional 10 mL of 1 M lithium aluminum hydride was added. After 30 min the reaction was quenched by the addition of 0.800 mL of concentrated aqueous ammonium hydroxide. After gas evoution ceased, the mixture was diluted with ether, filtered through celite, and evaporated. The residue was dissolved in 150 mL of methanol and treated with 3.0 mL of 12 N aqueous hydrochloric acid for 30 min. The reaction mixture was poured onto aqueous bicarbonate and extracted twice with ether. The ether layer was washed with brine, dried and evaporated. The residue was dissolved in 100 mL of boiling methanol after cooling in ice for 1 h, the precipitated methyl trityl ether was filtered off. The filtrate was evaporated to a solid which was suspended in 100 mL of boiling hexane. Pure colorless crystals of the title compound (4.04 g) were collected from the cooled mixture.

Part C: Preparation of trans-7-Chloro-5-(2-cyclopropylethenyl)-1,5-dihydro-5-(trifluoromethyl)-4,1-benzoxazepin-2(3H)-one To a stirred 0° solution of 230 mg of trans-6-amino-3-chloro-α-cyclopropylethenyl-α-(trifluoromethyl)benzyl alcohol in 10 mL of dry ether was added 0.140 mL of dry pyridine and 0.075 mL of bromoacetyl bromide. After 30 min, the reaction mixture was diluted with ether, washed with water and aqueous sodium bicarbonate, dried and evaporated. The residue was dissolved in 8 mL of dry DMF and was treated at 0° with 24 mg of 100% sodium hydride. After 15 min the cooling bath was removed and stirring was continued at ambient temperature for 3 h. The reaction was poured onto aqueous ammonium chloride and extracted with ether. The ether layer was washed with brine, dried and evaporated. The crude product was purified by column chromatiography over silica gel (elution with ethyl acetate/hexanes 1:3) affording after crystallization from ethyl acetate/hexanes 127 mg of the title compound as colorless crystals: mp 157–158°; HRMS Calcd. for $C_{15}H_{14}NO_2ClF_3$ $(M+H)^+$: 332.066516. Found: 332.064517.

Example 6

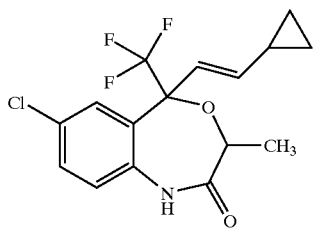

Preparation of rel-(3S,5S)-trans-7-Chloro-5-(2-cyclopropylethenyl)-1,5-dihydro-3-methyl-5-(trifluoromethyl)-4,1-benzoxazepin-2(3H)-one To a stirred ice-cooled solution of 291 mg of trans-6-Amino-3-chloro-α-cyclopropylethenyl-α-(trifluoromethyl) benzyl alcohol (from Example 5, Part C) in 13 mL of dry ether was added 0.180 mL of dry pyridine and 0.120 mL of bromopropionyl bromide. After 1 h, the reaction mixture was diluted with ether, washed with water and aqueous sodium bicarbonate, dried and evaporated. The residue was dissolved in 10 mL of dry DMF and was treated at 0° with 40 mg of 100% sodium hydride. After 15 min the cooling bath was removed and stirring was continued at ambient temperature for 20 h. The reaction was poured onto aqueous ammonium chloride and extracted with ether. The ether layer was washed with brine, dried and evaporated. The residue was dissolved in a small amount of ethyl acetate, and addition of hexane resulted in the crystallization of 40 mg of the title compound as colorless crystals: mp 171–172°; HRMS: Calcd. for $C_{16}H_{16}NO_2ClF_3$ $(M+H)^+$: 346.082166. Found: 346.080681. A second crop of slightly less pure product weighed 41 mg.

Example 7

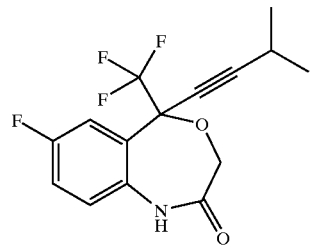

Preparation of 1,5-Dihydro-7-fluoro-5-isopropylethynyl-5-(trifluoromethyl)-4,1-benzoxazepin-2(3H)-one Part A: Preparation of N-(4-Fluorophenyl)-2,2-dimethylpropanamide To an ice-cooled solution of 125 mL of 4-fluoroaniline and 18.4 mL of triethylamine in 300 mL of methylene chloride was added dropwise over 30 min 14.8 mL of trimethylacetyl chloride. After addition was complete, the cooling bath was removed and stirring was continued at ambient temperature for 1 h. The reaction mixture was brought to pH 3 with 6N HCl and was partitioned between methylene chloride and water. Evaporation of the organic layer afforded a solid which was collected and washed with hexane to afford 21.35 g (83%) of the title compound as a crystalline solid.

Part B: Preparation of 1-(2-Amino-5-fluorophenyl)-2,2,2-trifluoroethanone

To an ice-cooled solution of 4.0 g of N-(4-fluorophenyl)-2,2-dimethylpropanamide in 80 mL of dry THF was added dropwise over 30 min 30.8 mL of a 1.6 M solution of n-butyllithium in hexane. After addition was complete, the reaction mixture was stirred an additional 1 h at 0° after which time 5.63 mL of ethyl trifluoroacetate was added quickly dropwise. The cooling bath was removed and the reaction was allowed to proceed at ambient temperature for 40 min. The reaction was quenched by the addition of aqueous ammonium chloride and the reaction mixture was partitioned between ether and water. The ether layer was washed with brine, dried and evaporated to 6.29 g of the title compound as an orange oil. The bulk of this material (6.0 g) was dissloved in ethylene glycol dimethyl ether, 30 mL of 6N HCl was added nd the mixture was heated at reflux for 1.5 h. The cooled reaction mixture was diluted with water, and made basic by the addition of solid sodium carbonate. This was extracted with ether, and the combined extacts were dried and evaporated. The residue was purified by column chromatography over silica gel (elution with 10–20% ethyl acetate in hexanes) affording 2.10 g of the title compound as an orange solid.

Part C: Preparation of 6-Amino-3-fluoro-α-isopropylethynyl-α-(trifluoromethyl)benzyl alcohol To an ice-cooled solution of 1.89 mL of isopropylacetylene in 35 mL of dry THF was added dropwise over 5 min, 10.0 mL of 1.6 M n-butyllithium. The reaction mixture was stirred at 0° for 30 min after which time 828 mg of 1-(2-amino-5-fluorophenyl)-2,2,2-trifluoroethanone was added. The reaction mixture was stirred at 0° for 1.25 h after which time it was quenched with saturated aqueous ammonium chloride and poured onto water. This mixture was extracted twice with ether and the combined extracts were washed with brine dried and evaporated. The residue was purified by column chromatography on silica gel (elution with ethyl acetate/hexanes) affording 220 mg of the title compound as a tan solid.

Part D: 1,5-Dihydro-7-fluoro-5-isopropylethynyl-5-(trifluoromethyl)-4,1-benzoxazepin-2(3H)-one To a stirred 0° solution of 210 mg of 6-Amino-3-fluoro-α-isopropylethynyl-α-(trifluoromethyl)benzyl alcohol in 20 mL of dry ether was added 0.120 mL of dry pyridine and 0.080 mL of bromoacetyl bromide. After 30 min, the reaction mixture was diluted with ether, washed with water and aqueous sodium bicarbonate, dried and evaporated. The residue was dissolved in 20 mL of dry DMF and was treated at room temperature with 33 mg of 100% sodium hydride for 30 min. The reaction was partitioned between ethyl acetate and water and the ethyl acetate layer was washed with brine, dried and evaporated. The crude product was purified by column chromatography over silica gel (elution with ethyl acetate/hexanes 1:2) affording after crystallization from ethyl acetate/hexanes 89 mg of the title compound as colorless crystals: mp 172–173°; Anal. Calcd. for C$_{15}$H$_{13}$NO$_2$F$_4$: C, 57.15; H, 4.17; N, 4.44. Found: C, 57.10; H, 3.98; N, 4.21.

Example 8

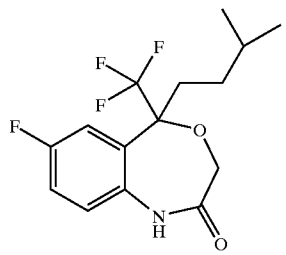

Preparation of 1,5-Dihydro-7-fluoro-5-(3-methylbutyl)-5-(trifluoromethyl)-4,1-benzoxazepin-2(3H)-one A solution of 32 mg of 7-fluoro-5-isopropylethynyl-5-(trifluoromethyl)-4,1-benzoxazepin-2-one in 4 mL of ethanol was stirred under 1 atmosphere of hydrogen in the presence of 5 mg of 10% palladium on carbon for 12 h. Filtration and evaporation afforded a solid material which was recrystallized from ethyl acetate/hexanes to afford 18 mg of the title compound as colorless crystals: HRMS: Calcd. for C$_{15}$H$_{18}$NO$_2$F$_4$ (M+H)$^+$: 320.127367. Found: 320.127936.

Example 9

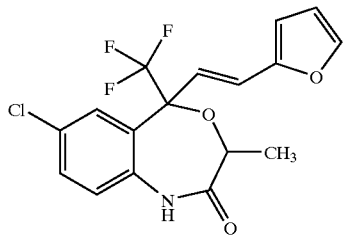

Preparation of rel-(3S,5S)-trans-7-Chloro-1,5-dihydro-5-(2-furan-2-ylethenyl)-3-methyl-5-(trifluoromethyl)-4,1-benzoxazepin-2(3H)-one Part A: Preparation of 1,1-dibromo-2-furan-2-yl-ethylene To a stirred solution of 9.6 g (29 mmol) of carbon tetrabromide in 120 mL of dry methylene chloride at 0° was added 15.2 g (58 mmol) of triphenylphosphine. After 15 min 3.0 mL (22.5 mmol) of triethylamine was added, and after stirring another 5 min at 0°, the reaction mixture was cooled to −78°. At this temperature 1.50 mL (22.5 mmol) of 2-furaldehyde was added quickly dropwise, and after addition was complete, the mixture was stirred a −70° for 30 min. The reaction mixture was poured onto a rapidly stirring saturated solution of sodium bicarbonate in water. The methylene chloride phase was removed and the aqueous layer was extracted with additional methylene chloride. The combined extracts were evaporated to a solid which was stirred in 500 mL of hexanes for 2 h. After filtration, the filtrate was concentrated to a volume of 50 mL and the filtered again to remove precipitated solid. Final evaporation of the filtrate afforded 3.1 g (58%) of the title compound.

Part B: Preparation of 3-Chloro-6-(triphenylmethy)amino-α-(2-furanyl)ethynyl-α-(trifluoromethyl)benzyl alcohol To a solution of 2.88 g (11.4 mmol) of 1,1-dibromo-2-furan-2-ylethene in 40 mL of dry THF at −20° was added dropwise over 5 min, 14.25 mL (22.8 mmol) of 1.6 M n-butyllithium. The reaction mixture was allowed to warm to 0° over 30 min at which time a solution of 4.2 g (9.0 mmol) of 1-(5-chloro-2-triphenylmethylamino)phenyl-2,2,2-trifluoroethanone in 12 mL of dry THF was added dropwise over 1 min. The reaction mixture was stirred at 0° for 30 min after which time it was poured onto saturated aqueous ammonium chloride. This mixture was extracted twice with ether and the combined extracts were washed with brine, dried, and evaporated to 5.6 g of 3-chloro-6-(triphenylmethy)amino-α-(furan-2-yl)ethynyl-α-(trifluoromethyl)benzyl alcohol as a dark colored solid.

Part C: Preparation of trans-6-Amino-3-chloro-(2-furan-2-yl)ethenyl-α-(trifluoromethyl)benzyl alcohol To a stirred solution of 3.35 g of 3-chloro-6-(triphenylmethy)amino-α-(furan-2-yl)ethynyl-α-(trifluoromethyl)benzyl alcohol in 25 mL of dry THF was added 6 mL of 1.0 M lithium aluminum hydride in THF. After 1 h the reaction was quenched by the addition of 0.54 mL of concentrated aqueous ammonium hydroxide. After gas evolution ceased, the mixture was diluted with ether, filtered through celite, and evaporated. The residue was dissolved in 30 mL of methanol and treated with 0.70 mL of 12 N aqueous hydrochloric acid for 30 min. The reaction mixture was poured onto aqueous bicarbonate and extracted with ether. The ether layer was washed with brine, dried and evaporated. The residue was dissolved in methanol after cooling in ice for 1 h and the precipitated methyl trityl ether was filtered off. After evaporation of the filtrate, crystallization from hexanes afforded 888 mg of trans-3-chloro-6-amino-α-(furan-2-yl)ethenyl-α-(trifluoromethyl)benzyl alcohol as crystals.

Part D: Preparation of rel-(3S,5S)-trans-7-Chloro-1,5-dihydro-5-(2-furan-2-yl)ethenyl-3-methyl-5-(trifluoromethyl)-4,1-benzoxazepin-2(3H)-one To a stirred 0° solution of 317 mg of trans-3-chloro-6-amino-α-(furan-2-yl)ethenyl-α-(trifluoromethyl)benzyl alcohol in 15 mL of dry ether was added 0.100 mL of dry pyridine and 0.125 mL of bromopropionyl bromide. After 30 min, the reaction mixture was diluted with ether, washed with water and aqueous sodium bicarbonate, dried and evaporated. The residue was dissolved in 15 mL of dry DMF, 268 mg of lithium iodide and 489 mg of cesium carbonate was added, and the resulting heterogeneous mixture was stirred at room temperature for 24 h. The reaction mixture was then poured onto water and extracted twice with ether. The combined extracts were washed with water and brine, dried and evaporated to 350 mg of crude product from which 108 mg of a single isomer could be isolated by crystallization (ethyl acetate/hexanes). This material was purified further on a short silica gel column, and then recrystallized from ethyl acetate/hexanes to give 86 mg of the title compound as colorless crystals: mp 205–206.5°; Anal. Calcd. for C$_{17}$H$_{13}$NO$_3$F$_3$Cl: C, 54.93; H, 3.54; N, 3.78. Found: C, 54.83; H, 3.40; N, 3.61.

Example 10

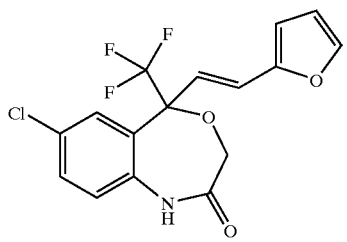

Preparation of trans-7-Chloro-1,5-dihydro-5-(2-furan-2-yl)ethenyl-5-(trifluoromethyl)-4,1-benzoxazepin-2(3H)-one To a stirred ice-cooled solution of 159 mg of trans-3-chloro-6-amino-α-(furan-2-yl)ethenyl-α-(trifluoromethyl) benzyl alcohol (from Example 9, Part C) in 8 mL of dry ether was added 0.050 mL of dry pyridine and 0.055 mL of bromoacetyl bromide. After 30 min, the reaction mixture was diluted with ether, washed with water and aqueous sodium bicarbonate, dried, and evaporated. The residue was dissolved in 8 mL of dry DMF, 245 mg of cesium carbonate was added, and the resulting heterogeneous mixture was stirred at room temperature for 1.5 h. The reaction mixture was then poured onto water and extracted twice with ether. The combined extracts were washed with water and brine, dried and evaporated to crude product from which 86 mg of crystalline material was obtained (ethyl acetate/hexanes). This material was purified further on a short silica gel column (elution with ethyl acetate/hexanes 1:1), and then recrystallized from ethyl acetate/hexanes to give 68 mg of title compound: mp 199–200°; Anal. Calcd. for $C_{16}H_{11}NO_3F_3Cl$: C, 53.72; H, 3.11; N, 3.93. Found: C, 54.09; H, 3.35; N, 3.83.

Example 11

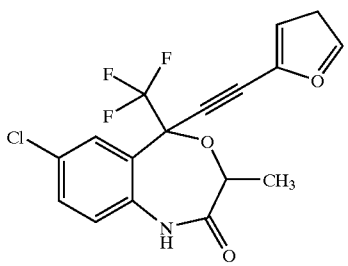

Preparation of rel-(3S,5S)-7-Chloro-1,5-dihydro-5-(2-furanyl)ethynyl-3-methyl-5-(trifluoromethyl)-4,1-benzoxazepin-2(3H)-one Part A: Preparation of 6-Amino-3-chloro-α-(furan-2yl)ethynyl-α-(trifluoromethyl)benzyl alcohol To a stirred solution of 2.0 g of 3-Chloro-6-(triphenylmethy)amino-α-(2-furanyl)ethynyl-α-(trifluoromethyl)benzyl alcohol (Example 9, Part B) in 20 mL of methanol was added 0.125 mL of 12 N aqueous hydrochloric acid, and the resulting solution was stirred at ambient temperature for 30 min. The reaction mixture was poured onto aqueous bicarbonate and extracted with ether. The ether layer was washed with brine, dried and evaporated. The residue was dissolved in methanol after cooling in ice for 1 h, the precipitated methyl trityl ether was filtered off. After evaporation of the filtrate, the residue was chromatographed over silica gel (elution with hexanes/ethyl acetate 3:1) affording after crystalization from hexane/ethyl acetate 280 mg of the title compound.

Part B: Preparation of rel-(3S,5S)-7-Chloro-1,5-dihydro-5-(2-furanyl)ethynyl-3-methyl-5-(trifluoromethyl)-4,1-benzoxazepin-2(3H)-one To a stirred ice-cooled solution of 265 mg of 6-amino-3-chloro-α-(furan-2-yl)ethynyl-α-(trifluoromethyl)benzyl alcohol in 10 mL of dry ether was added 0.150 mL of dry pyridine and 0.100 mL of bromopropionyl bromide. After 30 min, the reaction mixture was diluted with ether, washed with water and aqueous sodium bicarbonate, dried and evaporated. The residue was dissolved in 10 mL of dry DMF at 0°, 25 mg of 100% sodium hydride was added, and the resulting mixture was stirred for 15 min at 0° and at room temperature for 30 min. The reaction mixture was then poured onto water and extracted twice with ether. The combined extracts were washed with water and brine, dried and evaporated to a residue which was purified by column chromatography on silica gel (elution with 17–33% ethyl acetate in hexanes) affording after crystallization from ethyl acetate/hexanes 5 mg of the title compound: HRMS: Calcd. for $C_{17}H_{12}NO_3C_1F_3$ (M+H)$^+$: 369.037956. Found: 369.036835.

Example 12

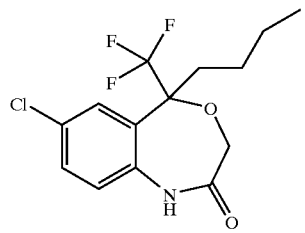

Preparation of 5-Butyl-7-chloro-1,5-dihydro-5-(trifluoromethyl)-4,1-benzoxazepin-2(3H)-one Part A: Preparation of 6-Amino-3-chloro-α-butyl-α-(trifluoromethyl)benzyl alcohol To an ice-cooled solution of 465 mg (1 mmol) of 1-(5chloro-2-triphenylmethylamino)phenyl-2,2,2-trifluoroethanone in 15 mL of dry THF was added dropwise 2 mmol of n-butylmagnesium chloride in ether. The reaction mixture was stirred at 0° for 30 min after which time it was quenched with saturated aqueous ammonium chloride and poured onto water. This mixture was extracted twice with ether and the combined extracts were washed with brine, dried, and evaporated to a pure solid. This material was was dissolved in 10 mL of methanol and treated with 0.100 mL of 12 N aqueous hydrochloric acid for 1 h. The reaction mixture was partitioned between water and ether, and the ether layer was washed with aqueous bicarbonate, brine, dried and evaporated. Crystallization from hexanes afforded 195 mg of the title compound as a crystalline solid.

Part B: Preparation of 5-Butyl-7-chloro-1,5-dihydro-5-(trifluoromethyl)-4,1-benzoxazepin-2 (3H)-one To a stirred ice-cooled solution of 185 mg of 6-amino-3-chloro-α-butyl-α-(trifluoromethyl)benzyl alcohol in 15 ML of dry ether was added 0.100 mL of dry pyridine and 0.060 mL of bromoacetyl bromide. After 30 min, the reaction mixture was diluted with ether, washed with water and aqueous sodium bicarbonate, dried and evaporated. The residue was dissolved in 8 mL of dry DMF and was treated at room temperature with 40 mg of 100% sodium hydride for 16 h. The reaction was partitioned between ethyl acetate and water and the ethyl acetate layer was washed with brine, dried, and evaporated. The crude product was purified first by column chromatography over silica gel (elution with ethyl acetate/hexanes 1:3), and then by preparative silica gel TLC (elution with 2.5% methanol in methylene chloride) affording 32 mg of the title compound as an amorphous solid: HRMS: Calcd. for $C_{14}H_{16}NO_2ClF_3$ $(M+H)^+$: 322.082166. Found: 322.080685.

Example 13

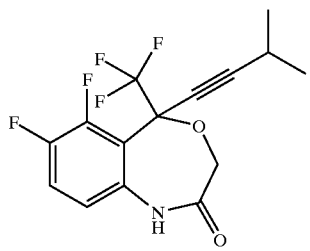

Preparation of 4-Isopropylethynyl-4-trifluoromethyl-5,6-difluoro-1,4-dihydro-2H-3,1-benzoxazin-2-one Part A: Preparation of N-triLethylacetyl-3,4-difluoroanilide To a solution of 3,4-difluoroaniline (19 mL, 191 mmol) in methylene chloride (500 mL) at 0° was added triethylamine (32 mL, 230 mmol) followed dropwise with trimethylacetyl chloride (24 mL, 191 mmol) and the resulting reaction mixture was allowed to stir at room temperature for 3 h. The reaction mixture was poured onto 3N HCl and extracted with methylene chloride (3×100 mL) and the combined organic extracts were dried over anhydrous $NaSO_4$ and concentrated in vacuo. The residue was taken up in hexanes (300 mL) and filtered through a sintered glass funnel. The solids are washed thoroughly with hexanes (500 mL) and dried under vacuum to give 37.36 g of the pivaloyl amide as a solid (40.68 g theoretical, 92% yield).

Part B: Preparation of N-TriLmethylacetyl 5,6-difluoro-2-trifluoroacetylanilide.

To a solution of N-trimethylacetyl-3,4-difluoroanilide (4.0 g, 14.6 mmol) in THF (60 mL) at −78° C. was added dropwise 1.6M nBuLi in hexane (22 mL, 35 mmol) and the resulting reaction mixture was allowed to stir at −78° C. for 1 h. Ethyl trifluoroacetate (4 mL, 33.6 mmol) was added to the reaction mixture and the resulting solution was allowed to stir with warming to room temperature (ice bath removed after the addition of reagent) for 0.5 h. The reaction mixture was poured onto saturated $NH_4Cl$ and extracted with ether (3×50 mL). The combined ether extracts were dried over anhydrous $MgSO_4$ and concentrated in vacuo to give an orange oil. This product was used in the next step of the synthetic sequence without further purification.

Part C: Preparation of 5,6-Difluoro-2-trifluoroacetylaniline.

To a solution of the orange oil in dimethoxyethane (15 mL) was added 6N HCl (75 mL) and the resulting mixture was allowed to reflux for 2 h. The reaction mixture was cooled, made basic with solid $Na_2CO_3$ and extracted with ether (3×50 mL). The combined ether extracts were dried over anhydrous $MgSO_4$ and concentrated in vacuo. Chromatography ($SiO_2$, 20% EtOAc-hexanes eluant) provided 2110 mg of 5,6-Difluoro-2-trifluoroacetylaniline as a yellow solid (3285 mg theoretical, 64% yield).

Part D: Preparation of 1-(2,3-difluoro-6-triphenylmethylamino)phenyl-2,2,2-trifluoroethanone A solution of 500 mg of 5,6-Difluoro-2trifluoroacetylaniline, 693 mg of triphenylmethanol, and 8 mg of p-toluenesulfonic acid in 50 mL of toluene was heated a reflux for 3.5 h using a Dean-Stark trap for water separation. After evaporation of thhe solvent, the residue was purified by column chromatography over silica gel (5% ethylacetate in hexanes as eluent) affording 760 mg of the title compound as a yellow foam.

Part E: Preparation of 6-Amino-2,3-difluoro-α-(isopropylethynyl)-α-(trifluoromethyl)benzyl alcohol To an ice-cooled solution of 250 mg of isopropylacetylene in 10 mL of dry THF was added dropwise 1.90 mL of a 1.6 M solution of n-butyllithium in hexane. After 30 min at 0°, 450 mg of 1-(2,3-difluoro-6-triphenylmethylamino)phenyl-2,2,2-trifluoroethanone in 3 mL of dry THF was added quickly dropwise. The reaction mixture was stirred at 0° for 20 min after which time it was poured onto saturated aqueous ammonium chloride. This mixture was extracted twice with ether and the combined extracts were washed with brine dried and evaporated to an orange solid. 248 mg of this material was was dissolved in 5 mL of methanol and treated with 0.05 mL of 12 N aqueous hydrochloric acid for 20 min. The reaction mixture was partitioned between water and ether, and the ether layer was washed with aqueous bicarbonate, brine, dried, and evaporated. The crude product was purified by column chromatography over silica gel (elution with ethyl acetate/hexanes 1:3) affording 81 mg of the title compound.

Part F: Preparation of 6,7-Difluoro-1,5-dihydro-5-(isopropylethynyl)-5-(trifluoromethyl)-4,1-benzoxazepin-2(3H)-one To a stirred ice-cooled solution of 81 mg of 6-Amino-2,3-difluoro-α-(isopropylethynyl)-α-(trifluoromethyl)benzyl alcohol in 8 mL of dry ether was added 0.55 mL of dry pyridine and 0.032 mL of bromoacetyl bromide. After 30 min, the reaction mixture was diluted with ether, washed with water and aqueous sodium bicarbonate, dried and evaporated. The residue was dissolved in 10 mL of dry DMF and was treated at 0° with 10 mg of 100% sodium hydride for 20 min. The cooling bath was removed, and the reaction was allowed to proceed at ambient temperature for 1 h. The reaction was quenched with one drop of acetic acid and then the mixture was concentrated in vacuo. The residue was dissolved in ethyl acetate and this solution was washed with water and brine, dried and evaporated to a solid which was crystallized from ethyl acetate/hexanes affording 28 mg of the title compound as colorless crystals: mp 192.5–193.5°; HRMS: Calcd. for $C_{15}H_{13}NO_2F_5$ $(M+H)^+$: 334.086645. Found: 334.084917.

Example 14

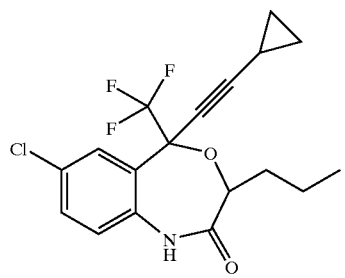

Preparation of rel-(3S,5S)-7-Chloro-5-cyclopropylethynyl-1,5-dihydro-3-propyl-5-(trifluoromethyl)-4,1-benzoxazepin-2(3H)-one (Example 14a) and rel-(3R,5S)-7-Chloro-5-cyclopropylethynyl-1,5-dihydro-3-propyl-5-(trifluoromethyl)-4,1-benzoxazepin-2(3H)-one (Example 14b)

Part A: Preparation of 6-Amino-3-chloro-α-cyclopropylethynyl-α-(trifluoromethyl)benzyl alcohol To a stirred solution of 3.0 g of 3-Chloro-6-(triphenylmethyl)amino-α-cyclopropylethynyl-α-(trifluoromethyl)benzyl alcohol (Example 5, Part A) in 30 mL of methanol was added 0.60 mL of 12 N aqueous hydrochloric acid, and this mixture was stirred at ambient temperature for 10 min. The reaction mixture was poured onto aqueous bicarbonate and extracted twice with ether. The combined extracts were washed withh brine, dried, and evaporated. The residue was dissolved in 20 mL of methanol and after cooling in ice for 1 h, the precipitated methyl trityl ether was filtered off. After evaporation of the filtrate, the crude solid was recrystallized from hexanes affording 1.16 g of the title compound as a purple solid.

Part B: Preparation of rel-(3S,5S)-7-Chloro-5cyclopropylethynyl-1,5-dihydro-3-propyl-5-(trifluoromethyl)-4,1-benzoxazepin-2(3H)-one and rel-(3R,5S)-7-Chloro-5cyclopropylethynyl-1,5-dihydro-3-propyl-5-(trifluoromethyl)-4,1-benzoxazepin-2(3H)-one To a stirred ice-cooled solution of 290 mg of 6-amino-3-chloro-α-cyclopropylethynyl-α-(trifluoromethyl)benzyl alcohol in 15 mL of dry ether was added 0.100 mL of dry pyridine and 220 mg of α-bromobutyryl chloride. After 30 min, the reaction mixture was diluted with ether, washed with water and aqueous sodium bicarbonate, dried and evaporated. The residue was dissolved in 15 mL of dry DMF, 268 mg of lithium iodide and 978 mg of cesium carbonate was added, and the resulting heterogeneous mixture was stirred at room temperature overnight. The reaction mixture was then poured onto water and extracted twice with ether. The combined extracts were washed with water and brine, dried and evaporated to 300 mg of crude product. This material was subjected to column chromatography over silica gel (elution with 5–25% ethyl acetate in hexanes) affording after crystallization from ethyl acetate/hexanes: 115 mg of rel-(3S,5S)-7-chloro-5-cyclopropylethynyl-1,5-dihydro-3-propyl-5-(trifluoromethyl)-4,1-benzoxazepin-2(3H)-one as colorless crystals: mp 191–192°; Anal. Calcd. for $C_{18}H_{17}NO_2F_3Cl$: C, 58.15; H, 4.62; N, 3.78. Found: C, 57.89; H, 4.61; N, 3.60, and 25 mg of rel-(3R,5S)-7-chloro-5-cyclopropylethynyl-1,5-dihydro-3-propyl-5-(trifluoromethyl)-4,1-benzoxazepin-2(3H)-one: mp 141°; HRMS: Calcd. for $C_{18}H_{18}NO_2F_3Cl$ $(M+H)^+$: 372.097816. Found: 372.096539.

Example 15

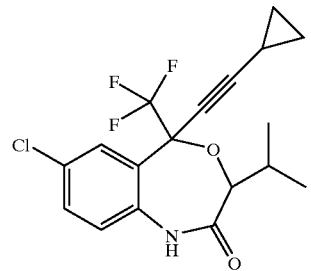

Preparation of rel-(3S,5S)-7-Chloro-5-cyclopropylethynyl-1,5-dihydro-3-isopropyl-5-(trifluoromethyl)-4,1-benzoxazepin-2(3H)-one To a stirred ice-cooled solution of 290 mg of 6-amino-3-chloro-α-cyclopropylethynyl-α-(trifluoromethyl)benzyl alcohol (Example 14, Part A) in 15 mL of dry ether was added 0.100 mL of dry pyridine and 228 mg of α-bromoisobutyryl chloride. After 30 min, the reaction mixture was diluted with ether, washed with water and aqueous sodium bicarbonate, dried and evaporated. The residue was dissolved in 15 mL of dry DMF, 268 mg of lithium iodide and 978 mg of cesium carbonate was added, and the resulting heterogeneous mixture was stirred at room temperature overnight. The reaction mixture was then poured onto water and etracted twice with ether. The combined extracts were washed with water and brine, dried and evaporated. Since TLC showed the reaction had only gone halfway to completion, the crude product was redissloved in 15 mL of DMF and subjected to the same reaction conditions as above for another 24 h. After the same work-up, the crude product was purified by column chromatography over silica gel (elution with 5–15% ethyl acetate in hexanes) and then recrystallized from ethyl acetate/hexanes to give 45 mg of the title compound as colorless crystals: mp 167°; Anal. Calcd. for $C_{18}H_{17}NO_2F_3Cl$: C, 58.15; H, 4.62; N, 3.78. Found: C, 58.11; H, 4.59; N, 3.70.

Example 16

7-Chloro-5-phenylethynyl-1,5-dihydro-5-(trifluoromethyl)-4,1-benzoxazepin-2(3H)-one The title compound was prepared in a manner similar to the product of Example 7, except that diisopropylethylamine was used as a base rather than sodium hydride: mp 190–191°; Anal. Calcd. for $C_{18}H_{11}NO_2F_3Cl$: C, 59.11; H, 3.03; N, 3.84. Found: C, 58.95; H, 3.12; N, 3.83.

Example 17 rel-(3S,5S)-7-Chloro-5-isopropylethynyl-1,5-dihydro-3-methyl-5-(trifluoromethyl)-4,1-benzoxazepin-2(3H)-one The title compound was prepared in a manner similar to the product of Example 7: mp 181–182.8°; Anal. Calcd. for $C_{16}H_{15}NO_2F_3Cl$: C, 55.58; H, 4.37; N, 4.05. Found: C, 55.37; H, 4.39; N, 3.87.

Example 18

7-Chloro-5-cyclopropylethynyl-1,5-dihydro-5-(trifluoromethyl)-4,1-benzoxazepin-2(3H)-one The title compound was prepared in a manner similar to the product of Example 7: mp 199.5–200.5°; Anal. Calcd.

Example 19

7-Chloro-5-isopropylethynyl-1,5-dihydro-5-(trifluoromethyl)-4,1-benzoxazepin-2(3H)-one The title compound was prepared in a manner similar to the product of Example 7: mp 168–1690; Anal. Calcd. for $C_{16}H_{16}NO_2F_3Cl$: C, 58.72; H, 4.94; N, 4.29. Found: C, 58.68; H, 4.90; N, 4.29.

Example 20 trans-7-Chloro-5-(2-isopropylethenyl)-1,5-dihydro-5-(trifluoromethyl)-4,1-benzoxazepin-2(3H)-one The title compound was prepared in a manner similar to the product of Example 5: mp 148–149°; HRMS: Calcd. for $C_{15}H_{16}NO_2F_3Cl$ (M+H)+: 334.082166. Found: 334.081071.

Example 21

7-Methoxy-5-(3-methylbutyl)-1,5-dihydro-5-(trifluoromethyl)-4,1-benzoxazepin-2(3H)-one The title compound was prepared in a manner similar to the product of Example 8: mp 129–130°; Anal. Calcd. for $C_{16}H_{20}NO_3F_3$: C, 58.00; H, 6.08; N, 4.24. Found: C, 57.86; H, 5.95; N, 4.12.

Example 22 rel-(3S,5S)-7-Chloro-5-cyclopropylethynyl-1,5-dihydro-3-ethyl-5-(trifluoromethyl)-4,1-benzoxazepin-2(3H)-one The title compound was obtained along with the title compound of Example 23 by a procedure similar to that of Example 7: mp 180–181°; Anal. Calcd. for $C_{17}H_{15}NO_2F_3Cl$: C, 57.07; H, 4.24; N, 3.93. Found: C, 56.85; H, 4.04; N, 3.95.

Example 23 rel-(3R,5S)-7-Chloro-5-cyclopropylethynyl-1,5-dihydro-3-ethyl-5-(trifluoromethyl)-4,1-benzoxazepin-2(3H)-one The title compound was obtained along with the title compound of Example 22 by a procedure similar to that of Example 7: mp 129–130°; HRMS. Calcd. for $C_{17}H_{15}NO_2F_3Cl$ (M+H)+: 358.082166. Found: 358.081980.

Example 24

7-Chloro-5-(3-pyridylethynyl)-1,5-dihydro-5-(trifluoromethyl)-4,1-benzoxazepin-2(3H)-one The title compound was prepared in a manner similar to the product of Example 11 except that sodium hydrid rather than cesium carbonate was the base used in the final reaction step: mp 219–221°; HRMS: Calcd. for $C_{17}H_{11}N_2O_2F_3Cl$ (M+H)+: 367.046115. Found: 367.046761.

Example 25 trans-7-Chloro-5-(3-pyrid-3-ylethenyl)-1,5-dihydro-5-(trifluoromethyl)-4,1-benzoxazepin-2(3H)-one The title compound was prepared in a manner similar to the product of Example 9 except that sodium hydride rather than cesium carbonate was the base used in the final reaction step: mp 199–201°; HRMS: Calcd. for $C_{17}H_{13}N_2O_2F_3Cl$ (M+H)+: 369.061765. Found: 369.060918.

Example 26 trans-7-Fluoro-5-(2-isopropylethenyl)-1,5-dihydro-5-(trifluoromethyl)-4,1-benzoxazepin-2(3H)-one The title compound was prepared in a manner similar to the product of Example 5: mp 145–156°.

Example 27 trans-6,7-Difluoro-5-(2-isopropylethenyl)-1,5-dihydro-5-(trifluoromethyl)-4,1-benzoxazepin-2(3H)-one The title compound was prepared in a manner similar to the product of Example 5: mp 159–160°; HRMS: Calcd. for $C_{15}H_{15}NO_2F_5$ (M+H)+: 336.102295. Found: 336.102028.

Example 28 rel-(3S,5S)-7-Chloro-5-cyclopropylethynyl-1,5-dihydro-3-methyl-5-(trifluoromethyl)-4,1-benzoxazepin-2(3H)-one The title compound was prepared in a manner similar to the product of Example 14: mp 169–174°; HRMS: Calcd. for

Example 29 rel-(3S,5S)-trans-7-Chloro-5-(2-cyclopropylethenyl)-1,5-dihydro-3-methyl-5-(trifluoromethyl)-4,1-benzoxazepin-2(3H)-one To a stirred ice-cooled solution of 987 mg of trans-6-amino-3 -chloro-α-cyclopropylethenyl-α-(trifluoromethyl) benzyl alcohol (from Example 5, Part B) in 50 mL of dry ether was added 0.350 mL of dry pyridine and 1.66 g of α-bromopropionyl bromide. The cooling bath was removed and then after 30 min at ambient temperature, the reaction mixture was diluted with ether, washed with water and aqueous sodium bicarbonate, dried and evaporated. The residue was dissolved in 50 mL of dry DMF, 2.35 g of lithium iodide and 2.3 g of cesium carbonate was added, and the resulting heterogeneous mixture was stirred at room temperature for 3 days. The reaction mixture was then poured onto water and extracted twice with ether. The combined extracts were washed with water and brine, dried and evaporated to crude product. The title compound was obtained by crystallization from ethyl acetate/hexanes, and recrystallization from ethyl acetate afforded 650 mg of pure title compound: mp 171–172°; HRMS: Calcd. for $C_{16}H_{168}NO_2F_3Cl$ (M+H)+: 346.082166. Found: 346.080681: mp 147–147.5°; HRMS: Calcd. for $C_{17}H_{18}NO_2F_3Cl$ (M+H)+: 360.097816. Found: 360.097869

Example 30 rel-(3S,5S)-trans-7-Chloro-5-(2-cyclopropylethenyl)-1,5-dihydro-3-propyl-5-(trifluoromethyl)-4,1-benzoxazepin-2(3H)-one The title compound was prepared in a manner similar to the product Example 29: mp 167–167° HRMS: Calcd. for $C_{18}H_{19}NO_2F_3Cl$ (M+H)+: 374.113467. Found: 374.114742.

Example 31 rel-(3S,5S)-7-Chloro-5-(3-furanylethynyl)-1,5-dihydro-3-methyl-5-(trifluoromethyl)-4,1-benzoxazepin-2(3H)-one The title compound was prepared in a manner similar to the product of Example 11 except that cesium carbonate/ lithium iodide rather than sodium hydride was used in the final reaction step: mp 214–215°.

Example 32 rel-(3S,5S)-7-Chloro-5-(3-furanylethynyl)-1,5-dihydro-3-ethyl-5-(trifluoromethyl)-4,1-benzoxazepin-2(3H)-one The title compound was prepared in a manner similar to the product of Example 11 except that cesium carbonate/lithium iodide rather than sodium hydride was used in the final reaction step: mp 169–170°; HRMS: Calcd. for $C_{18}H_{14}NO_3F_3Cl$ (M+H)$^+$: 384.061431. Found: 384.058632.

Example 33 rel-(3S,5S)-6,7-Difluoro-5-cyclopropylethynyl-1,5-dihydro-3-methyl-5-(trifluoromethyl)-4,1-benzoxazepin-2(3H)-one The title compound was prepared in a manner similar to the product of Example 14: mp 219–220°.

Example 34 rel-(3S,5S)-6,7-Difluoro-5-cyclopropylethynyl-1,5-dihydro-3-ethyl-5-(trifluoromethyl)-4,1-benzoxazepin-2(3H)-one The title compound was prepared in a manner similar to the product of Example 14: mp 180.4–181.4°.

Example 35 rel-(3S,5S)-trans-6,7-Difluoro-5-(2-cyclopropylethenyl)-1,5-dihydro-3-methyl-5-(trifluoramethyl)-4,1-benzoxazepin-2(3H)-one The title compound was prepared in a manner similar to the product of Example 6 except that cesium carbonate/lithium iodide rather than sodium hydride was used in the final reaction step: mp 192–193°; HRMS: Calcd. for $C_{16}H_{15}NO_2F_5$ (M+H)$^+$: 348.102295. Found: 348.102515.

Example 36

(+)-(3S,5S)-7-Chloro-5-cyclopropylethynyl-1,5-dihydro-3-methyl-5-(trifluoromethyl)-4,1-benzoxazepin-2(3H)-one The title compound can be prepared from the product of Example 28 in a manner similar to the procedure described in Example 4: mp 145–146°; Anal. Calcd. for $C_{16}H_{13}NO_2F_3Cl$ C, 55.91; H, 3.81; N, 4.07. Found: C, 55.80; H, 3.75; N, 3.88. $[\alpha]^{25}$ +94.200.

Example 37

(3S)-7-Chloro-5-cyclopropylethynyl-1,5-dihydro-5-(trifluoromethyl)-4,1-benzoxazepin-2(3H)-one The title compound can be prepared from the product of Example 18 in a manner similar to the procedure described in Example 4: mp 135–136°; Anal. Calcd. for $C_{15}H_{11}NO_2F_3Cl$ C, 54.64; H, 3.36; N, 4.26. Found: C, 54.69; H, 3.17; N, 4.00.

Example 38 rel-(3S,5S)-trans-7-Chloro-5-(2-cyclopropylethenyl)-1,5-dihydro-3-ethyl-5-(trifluoromethyl)-4,1-benzoxazepin-2(3H)-one The title compound can be prepared in a manner similar to the procedure described in Example 29 ; mp 147–147.5°; HRMS: Calcd. for $C_{17}H_{18}NO_2F_3Cl$ (M+H)$^+$: 360.097816. Found: 360.097869

Example 39

(+)-(3S,5S)-trans-7-Chloro-5-(2-cyclopropylethenyl)-1,5-dihydro-3-methyl-5-(trifluoromethyl)-4,1-benzoxazepin-2(3H)-one The title compound can be prepared from the product of Example 29 in a manner similar to the procedure described in Example 4: mp 175–175.5°; Anal. Calcd. for $C_{16}H_{15}NO_2F_3Cl$ C, 55.58; H, 4.37; N, 4.05. Found: C, 55.38; H, 4.21; N, 3.83. $[\alpha]^{25}$ +61.70.

Example 40

(+)-(3S,5S)-trans-7-Chloro-5-(2-cyclopropylethenyl)-1,5-dihydro-3-ethyl-5-(trifluoromethyl)-4,1-benzoxazepin-2(3H)-one The title compound can be prepared from the product of Example 38 in a manner similar to the procedure described in Example 4: mp 163–1640; $[\alpha]^{25}$ +22.7°.

Example 41 rel-(3S,5S)-7-Chloro-5-(2-cyclopropylethynyl)-1,5-dihydro-3-ethenyl-5-(trifluoromethyl)-4,1-benzoxazepin-2(3H)-one Part A: Preparation of 1-(5-Chloro-2-(4-methoxyphenyl)methylamino)phenyl-2,2,2-trifluoroethanone A mixture of 6.0 g of 1-(2-amino-5-chlorophenyl)-2,2,2-trifluoroethanone, 3.84 mL of 4-methoxybenzyl alcohol, 114 mg of p-toluensulfonic acid, and 25 mL of dry acetonitrile was heated at 80° for 3.5 hr. An additional 0.5 g of 4-methoxybenzyl alcohol was added and heating was continued for another 2 hr. The cooled solution was diluted with ethyl brine, dried and evaporated. This material was subjected to column chromatography over silica gel (elution with 5–10% ethyl acetate in hexanes) affording 8.2 g of 1-(5-chloro-2-(4-methoxyphenyl)methylamino)phenyl-2,2,2-trifluoroethanone as a yellow solid.

Part B: Preparation of 3-Chloro-6-(4-methoxyphenyl)methylamino-cyclopropylethynyl-α-(trifluoromethyl)benzyl alcohol To an ice-cooled solution of 3.92 g (59.6 mmol) of cyclopropylacetylene in 100 mL of dry THF was added dropwise over 5 min, 33.0 mL (52.4 mmol) of 1.6 M n-butyllithium. The reaction mixture was allowed to stir at 0° for 30 min after which time it was cooled to −40° and a solution of 8.20 g (23.85 mmol) of 1-(5-chloro-2-(4-methoxyphenyl)methylamino)phenyl-2,2,2-trifluoroethanone in 20 mL of dry THF was added dropwise over 5 min. The reaction mixture was stirred at −40° for 2.0 h after which time it was quenched with saturated aqueous ammonium chloride and poured onto water. This mixture was extracted twice with ether and the combined extracts were washed with brine, dried, and evaporated to an oil. This material was subjected to column chromatography over silica gel (elution with 5–20% ethyl acetate in hexanes) affording 6.0 g of the title compound as a solid.

Part C: 3-(2-Bromoethyl)-7-chloro-5-cyclopropylethynyl-1,5-dihydro-1-(4-methoxybenzyl)-5-(trifluoromethyl)-4,1-benzoxazepin-2(3H)-one To a solution of 1.64 g of 3-chloro-6-(4-methoxyphenyl)methylamino-α-cyclopropylethynyl1-(trifluoromethyl)

benzyl alcohol and 2.0 mL of diisopropylethylamine in 30 mL of dry methylene chloride was added 1.6 g of 2,4-dibromobutyryl chloride. After stirring at room temperature overnight, the mixture ws poured onto water and extracted with ether. The ether layer was washed with aqueous sodium bicarbonate, dried, and evaporated to an oil. This material was subjected to column chromatography over silica gel (elution with 5–10% ethyl acetate in hexanes) affording 1.13 g of the title compound as a mixture of diastereomers.

Part D: rel-(3S,5S)-3-(2-Bromoethyl)-7-chloro-5-cyclopropylethynyl-1,5-dihydro-5-(trifluoromethyl)-4,1-benzoxazepin-2(3H)-one To a room temperature solution of 1.13 g of 3-(2-bromoethyl)-7-chloro-5-cyclopropylethynyl-1,5-dihydro-1-(4-methoxybenzyl)-5-(trifluoromethyl)-4,1-benzoxazepin-2 (3H)-one in 50 mL of acetonitrile was added 25 mL of water and 5.7 g of ceric ammonium nitrate. After 30 min, the reaction mixture was partitioned between water and ether, and the organic layer was washed with aqueous bicarbonate and brine, dried and evaporated. This produced two diastereomeric products which were separated by column chromatography over silica gel (elution with 10–25% ethyl acetate in hexanes). The first diastereomer eluted (270 mg) was the title compound.

Part E: rel-(3S,5S)-7-Chloro-5-(2-cyclopropylethynyl)-1,5-dihydro-3-ethen yl-5-(trifluoromethyl)-4,1-benzoxazepin-2(3H)-one To a room temperature solution of 409 mg (1.8 mmol) of 2-nitrophenylselenocyanate in 5.0 mL of THF was added 16 mL of ethanol and 90 mg of sodium borohydride. After stirring 1 h, a solution of 260 mg of rel-(3S,5S)-3-(2-Bromoethyl)-7-chloro-5-cyclopropylethynyl-1,5-dihydro-5-(trifluoromethyl)-4,1-benzoxazepin-2(3H)-one in 1.5 mL of dry THF and 8 mL of ethanol was added, and the resulting mixture was stirred at ambient temperature for 2 h, at which time an additional 20 for an additional 2 h. The reaction mixture was partitioned between water and ether, and the organic layer was washed with aqueous bicarbonate and brine, dried and evaporated. The crude product was purified by column chromatography over silica gel (elution with 10–25% ethyl acetate in hexanes) to give 130 mg of the title compound as a pure solid: HRMS: Calcd. for $C_{17}H_{14}NO_2F_3Cl$ $(M+H)^+$: 354.0508. Found: 354.0487.

Example 42 rel-(3S,5S)-trans-7-Chloro-5-(2-cyclopropylethenyl)-1,5-dihydro-3-ethenyl-5-(trifluoromethyl)-4,1-benzoxazepin-2(3H)-one Part A: Preparation of trans-3-Chloro-6-(4-methoxyphenyl)methylamin-α-cyclopropylethenyl-α-(trifluoromethyl)benzyl alcohol To a solution of 1.23 g of 3-chloro-6-(4-methoxyphenyl) methylamino-α-cyclopropylethynyl-α-(trifluoromethyl) benzyl alcohol (from Example 41, Part B) in 12 mL of dry THF was added 15 mL of a 1M solution of lithium aluminum hydride in THF. The reaction mixture was stirred at ambient temperature for 3 days after which time it was quenched by the dropwise addition of 1.1 mL of concentrated aqueous ammonium hydroxide. This mixture was poured onto water and extracted with ether. The extracts were washed with brine, dried and evaporated to afford 1.15 g of the title compound as a pure oil.

Part B: trans-3-(2-Bromoethyl)-7-chloro-5-cyclopropylethenyl-1,5-dihydro-1-(4-methoxybenzyl)-5-(trifluoromethyl)-4,1-benzoxazepin-2(3H)-one To a solution of 1.65 g of trans-3-chloro-6-(4-methoxyphenyl)methylamino-α-cyclopropylethenyl-α-diisopropylethylamine in 30 mL of dry methylene chloride was added 1.6 g of 2,4-dibromobutyryl chloride. After stirring at room temperature overnight, the mixture was poured onto water and extracted with ether. The ether layer was washed with aqueous sodium bicarbonate, dried and evaporated to an oil. This material was subjected to column chromatography over silica gel (elution with 5–33% ethyl acetate in hexanes) affording the title compound. A later eluting fraction (160 mg) proved to be uncyclized material, This was combined with 300 mg of cesium carbonate in 4 mL of DMF and stirred overnight at room temperature. The reaction mixture was poured onto water and extracted with ether. the organic layer was washed with brine, dried and evaporated to give when combined with the product obtained from the column chromatography 750 mg of the title compound as a mixture of diastereomers.

Part C: rel-(3S,5S)-trans-3-(2-Bromoethyl)-7-chloro-5-cyclopropylethenyl-1,5-dihydro-5-(trifluoromethyl)-4,1-benzoxazepin-2 (3H)-one To a room temperature solution of 750 mg of trans-3-(2bromoethyl)-7-chloro-5-cyclopropylethenyl-1,5-dihydro-1-(4-methoxybenzyl)-5-(trifluoromethyl)-4,1-benzoxazepin-2(3H)-one in 35 mL of acetonitrile was added 18 mL of water and 3.78 g of ceric ammonium nitrate. After 20 min, the reaction mixture was partitioned between water and ether, and the organic layer was washed with aqueous bicarbonate and brine, dried and evaporated. This produced two diastereomeric products which were separated by column chromatography over silica gel (elution with 10–25% ethyl acetate in hexanes). The first diastereomer eluted (162 mg) was the title compound.

Part D: rel-(3S,5S)-trans-7-Chloro-5-(2-cyclopropylethenyl)-1,5-dihydro-3-ethenyl-5-(trifluoromethyl)-4,1-benzoxazepin-2(3H)-one To a room temperature solution of 238 mg (1.05 mmol) of 2-nitrophenylselenocyanate in 3.0 mL of THF was added 9 mL of ethanol and 66 mg of sodium borohydride. After stirring 1.5 h, a solution of 153 mg of rel-(3S,5S)-trans-3-(2-bromoethyl)-7-chloro-5-cyclopropylethenyl-1,5-dihydro-5-(trifluoromethyl)-4,1-benzoxazepin-2(3H)-one in 1.5 mL of dry THF and 5 mL of ethanol was added, and the resulting mixture was stirred at ambient temperature for 32 h. The reaction mixture was partitioned between water and ether, and the organic layer was washed.with aqueous bicarbonate and brine, dried and evaporated. The crude product was purified by column chromatography over silica gel (elution with 10–25% ethyl acetate in hexanes) to give 73 mg of the title compound as a pure solid which can be recrystallized from ethanol-hexanes: mp 165.5–166.5°; HRMS: Calcd. for $C_{17}H_{16}NO_2F_3Cl$ $(M+H)^+$: 358.082166. Found: 358.081658.

Example 43 rel-(3S,5S)-7-Chloro-5-(2-cyclopropylethynyl)-1,5-dihydro-3-cyclopropyl-5-(trifluoramethyl)-4,1-benzoxazepin-2(3H)-one To a solution of 71 mg of rel-(3S,5S)-7-chloro-5-(2-cyclopropylethynyl)-1,5-dihydro-3-ethenyl-5-

(trifluoromethyl)-4,1-benzoxazepin-2(3H)-one (from Example 41) in 7.5 mL of anhydrous ether was added first 4 mg of palladium (II) acetate and then a solution of approximately 1.23 mmol of diazomethane in 3.5 mL of ether. After stirring 30 min at room temperature, the reaction mixture was filtered through a pad of filter-aid and the filtrate was evaporated to dryness. The crude product was purified by column chromatography over silica gel (elution with methylene chloride) to give 65 mg of the title compound as a pure solid was recrystallized from ether-hexanes to afford 36 mg: mp 192–192.5°; HRMS: Calcd. for $C_{18}H_{14}NO_2F_3Cl$ (M−H)⁻: 368.0665. Found: 368.0657.

Example 44 rel-(3S,5S)-trans-7-Chloro-5-(2-cyclopropylethenyl)-1,5-dihydro-3-cyclopropyl-5-(trifluoromethyl)-4,1-benzoxazepin-2(3H)-one To a solution of 73 mg of rel-(3S,5S)-trans-7-chloro-5-(2-cyclopropylethenyl)-1,5-dihydro-3-ethenyl-5-(trifluoromethyl)-4,1-benzoxazepin-2(3H)-one (from Example 42) in 7.5 mL of anhydrous ether was added first 4 mg of palladium (II) acetate and then a solution of approximately 1.23 mmol of diazomethane in 3.5 mL of ether. After stirring 30 min at room temperature, the reaction mixture was filtered through a pad of filter-aid and the filtrate was evaporated to dryness. The crude product was purified by column chromatography over silica gel (elution with methylene chloride) to give 47 mg of the title compound as a pure solid was recrystallized from ether-hexanes to afford 31 mg: mp 143–144°; HRMS: Calcd. for $C_{18}H_{16}NO_2F_3Cl$ (M−H)⁻: 370.0822. Found: 370.0801.

Example 45 rel-(3S,5S)-6,7-Difluoro-5-(2-cyclopropylethynyl)-1,5-dihydro-3-ethenyl-5-(trifluoromethyl)-4,1-benzoxazepin-2(3H)-one The title compound can be prepared in a manner similar to the procedure described in Example 41: mp 171–172°; HRMS: Calcd. for $C_{17}H_{13}NO_2F_5$ (M+H)⁺: 358.0866. Found: 358.0881.

Example 46 rel-(3S,5S)-6,7-Difluoro-5-(2-cyclopropylethynyl)-1,5-dihydro-3-cyclopropyl-5-(trifluoromethyl)-4,1-benzoxazepin-2(3H)-one The title compound can be prepared from the product of Example 45 in a manner similar to the procedure described in Example 43: mp 222–222.50; HRMS: Calcd. for $C_{18}H_{15}NO_2F_5$ (M+H)⁺: 373.1023. Found: 372.1013.

Example 47 rel-(3S,5S)-7-Fluoro-5-(2-cyclopropylethynyl)-1,5-dihydro-3-ethenyl-5-(trifluoromethyl)-4,1-benzoxazepin-2(3H)-one The title compound can be prepared in a manner similar to the procedure described in Example 41: Calcd. for $C_{17}H_{12}NO_2F_4$ (M−H)⁻: 338.0804. Found: 338.0815.

Example 48 rel-(3S,5S)-7-Fluoro-5-(2-cyclopropylethynyl)-1,5-dihydro-3-methyl-5-(trifluoromethyl)-4,1-benzoxazepin-2(3H)-one The title compound can be prepared in a manner similar to the procedure described in Example 14: mp 184–185°; HRMS: Calcd. for $C_{16}H_{14}NO_2F_4$ (M+H)⁺: 328.0961. Found: 328.0955.

Example 49 rel-(3S,5S)-7-Fluoro-5-(2-cyclopropylethynyl)-1,5-dihydro-3-ethyl-5-(trifluoromethyl)-4,1-benzoxazepin-2(3H)-one The title compound can be prepared in a manner similar to the procedure described in Example 14: mp 186°; Anal. Calcd. for $C_{17}H_{15}NO_2F_4$: C, 59.83; H, 4,43; N, 4.10. Found: C, 59.56; H, 4.37; N, 4.02.

Example 50 rel-(3S,5S)-trans-7-Fluoro-5-(2-cyclopropylethenyl)-1,5-dihydro-3-methyl-5-(trifluoromethyl)-4,1-benzoxazepin-2(3H)-one The title. compound can be prepared in a manner similar Calcd. for $C_{16}H_{16}NO_2F_4$ (M+H)⁺: 330.1117. Found: 330.1118.

Example 51 rel-(3S,5S)-trans-7-Fluoro-5-(2-cyclopropylethenyl)-1,5-dihydro-3-ethyl-5-(trifluoromethyl)-4,1-benzoxazepin-2(3H)-one The title compound can be prepared in a manner similar to the procedure described in Example 29: mp 148–149°; HRMS: Calcd. for $C_{17}H_{183}NO_2F_4$ (M+H)⁺: 344.1274. Found: 344.1265.

Example 52 rel-(3S,5S)-6,7-Methylenedioxy-5-(2-cyclopropylethynyl)-1,5-dihydro-3-methyl-5-(trifluoromethyl)-4,1-benzoxazepin-2(3H)-one The title compound can be prepared in a manner similar to the procedure described in Example 14: mp 252–253°.

Example 53 rel-(3S,5S)-6,7-Methylenedioxy-5-(2-cyclopropylethynyl)-1,5-dihydro-3-ethyl-5-(trifluoromethyl)-4,1-benzoxazepin-2(3H)-one The title compound can be prepared in a manner similar to the procedure described in Example 14: mp 201–202°; HRMS: Calcd. for $C_{18}H_{17}NO_4F_3$ (M+): 367.1031. Found: 367.1041.

Example 54 rel-(3S,5S)-trans-6,7-Methylenedioxy-5-(2-cyclopropylethenyl)-1,5-dihydro-3-methyl-5-(trifluoromethyl)-4,1-benzoxazepin-2(3H)-one The title compound can be prepared in a manner similar to the procedure described Example 29: mp 236–237°; HRMS: Calcd. for $C_{17}H_{17}NO_4F_3$ (M+H)⁺: 356.1110. Found: 356.1110.

Example 55 rel-(3S,5S)-trans-6,7-Methylenedioxy-5-(2-cyclopropylethenyl)-1,5-dihydro-3-ethyl-5-(trifluoromethyl)-4,1-benzoxazepin-2(3H)-one The title compound can be prepared in a manner similar to the procedure described in Example 29: mp 188–190°; HRMS: Calcd. for $C_{18}H_{19}NO_4F_3$ (M+H)⁺: 370.1267. Found: 370.1269.

TABLE 1

[Structure: benzazepinone with CF3, R2 at position 5, O at 4, Ra at position 3, G at positions 6/7/8]

| Ex. # | G | R² | Rᵃ | m.p. (° C.) | Mass Spec |
|---|---|---|---|---|---|
| 1 | 7-Cl | C≡C-Et | H | 167–168 | |
| 2 | 7-Cl | (S)-C≡C-Et | (S)-Ph | 198–199 | 394.08 |
| 3 | 7-Cl | C≡C-iPr | H | 183–183.5 | 332.07 |
| 4 (+) | 7-Cl | (S)-C≡C-iPr | H | 135–136 | |
| 5 | 7-Cl | trans-C=C-cycPr | H | 157–158 | 332.06 |
| 6 | 7-Cl | trans-C=C-cycPr | (S)-CH₃ | 171–172 | 346.08 |
| 7 | 7-F | C≡C-iPr | H | 172–173 | |
| 8 | 7-F | 3-methylbutyl | H | | 320.13 |
| 9 | 7-Cl | (S)-trans-C=C-2-furan | (S)-CH₃ | 205–206.5 | |
| 10 | 7-Cl | trans-C=C-2-furan | H | 199–200 | |
| 11 | 7-Cl | (S)-C≡C-2-furan | (S)-CH₃ | | 369.04 |
| 12 | 7-Cl | butyl | H | | 322.08 |
| 13 | 6,7-diF | C≡C-iPr | H | 192.5–193.5 | 334.08 |
| 14a | 7-Cl | (S)-C≡C-cycPr | (S)-CH₃ | 191–92 | |
| 14b | 7-Cl | (S)-C≡C-cycPr | (R)-CH₃ | 141 | 372.10 |
| 15 | 7-Cl | (S)-C≡C-cycPr | (S)-iPr | 167 | |
| 16 | 7-Cl | C≡C-Ph | H | 190–191 | |
| 17 | 7-Cl | (S)-C≡C-iPr | (S)-CH₃ | 181–182.8 | |
| 18 | 7-Cl | C≡C-cycPr | H | 199.5–200.5 | |
| 19 | 7-Cl | C≡C-iPr | H | 168–169 | |
| 20 | 7-Cl | trans-C=C-cycPr | H | 148–149 | |
| 21 | 7-CH₃O | C≡C-cycPr | H | 129–130 | |
| 22 | 7-Cl | (S)-C≡C-cycPr | (S)-Et | 180–181 | |
| 23 | 7-Cl | (S)-C≡C-cycPr | (R)-Et | 129–130 | 358.08 |
| 24 | 7-Cl | C≡C-3-pyridyl | H | 219–221 | 367.05 |
| 25 | 7-Cl | trans-C=C-3-pyridyl | H | 199–201 | 369.06 |
| 26 | 7-F | trans-C=C-iPr | H | 145–156 | |
| 27 | 6,7-F | trans-C=C-iPr | H | 159–160 | 336.10 |
| 28 | 7-Cl | (S)-C≡C-cycPr | (S)-CH₃ | 169–174 | 343.06 |
| 29 | 7-Cl | (S)-trans-C=C-cycPr | (S)-CH₃ | 147–147.5 | 360.10 |
| 30 | 7-Cl | (S)-trans-C=C-cycPr | (S)-Pr | 165–167 | 374.11 |
| 31 | 7-Cl | (S)-C≡C-3-furan | (S)-CH₃ | 214–215 | |
| 32 | 7-Cl | (S)-C≡C-3-furan | (S)-Et | 169–170 | 384.06 |
| 33 | 6,7-F | (S)-C≡C-cycPr | (S)-CH₃ | 219–220 | |
| 34 | 6,7-F | (S)-C≡C-cycPr | (S)-Et | 180.4–181.4 | |
| 35 | 6,7-F | (S)-C≡C-cycPr | (S)-CH₃ | 192–193 | 348.10 |
| 36 (+) | 7-Cl | (S)-C≡C-cycPr | (S)-CH₃ | 145–146 | |
| 37 | 7-Cl | (S)-C≡C-cycPr | H | 135–136 | |
| 38 | 7-Cl | (S)-trans-C=C-cycPr | (S)-Et | 147–147.5 | 360.10 |
| 39 (+) | 7-Cl | (S)-C≡C-cycPr | (S)-CH₃ | 175–175.5 | |
| 40 (+) | 7-Cl | (S)-trans-C=C-cycPr | (S)-Et | 163–164 | |
| 41 | 7-Cl | (S)-C≡C-cycPr | (S)-CH=CH₂ | | 354.05 |
| 42 | 7-Cl | (S)-trans-C=C-cycPr | (S)-CH=CH₂ | 165.5–166.5 | 358.08 |
| 43 | 7-Cl | (S)-C≡C-cycPr | (S)-cycPr | 192–192.5 | 368.07 |
| 44 | 7-Cl | (S)-trans-C=C-cycPr | (S)-cycPr | 143–144 | 370.08 |
| 45 | 6,7-F | (S)-C≡C-cycPr | (S)-CH=CH₂ | 171–172 | 358.09 |
| 46 | 6,7-F | (S)-C≡C-cycPr | (S)-cycPr | 222–222.5 | 372.10 |
| 47 | 7-F | (S)-C≡C-cycPr | (S)-CH=CH₂ | | 338.08 |
| 48 | 7-F | (S)-C≡C-cycPr | (S)-CH₃ | 184–185 | 328.10 |
| 49 | 7-F | (S)-C≡C-cycPr | (S)-Et | 186 | |
| 50 | 7-F | (S)-trans-C=C-cycPr | (S)-CH₃ | 180–182 | 330.11 |
| 51 | 7-F | (S)-trans-C=C-cycPr | (S)-Et | 148–149 | 344.13 |
| 52 | 6,7-(CH₂)₂O | (S)-C≡C-cycPr | (S)-CH₃ | 252–252 | |
| 53 | 6,7-(CH₂)₂O | (S)-C≡C-cycPr | (S)-Et | 201–202 | 367.10 |
| 54 | 6,7-(CH₂)₂O | (S)-trans-C=C-cycPr | (S)-CH₃ | 236–237 | 356.11 |
| 55 | 6,7-(CH₂)₂O | (S)-trans-C=C-cycPr | (S)-Et | 188–190 | 370.13 |

*Unless otherwise noted, stereochemistry is (+/−).

Tables 2 and 3 show representative compounds of the present invention. Each formula shown at the start of Table 2 and 3 is intended to be paired with each entry in the table which follows.

TABLE 2

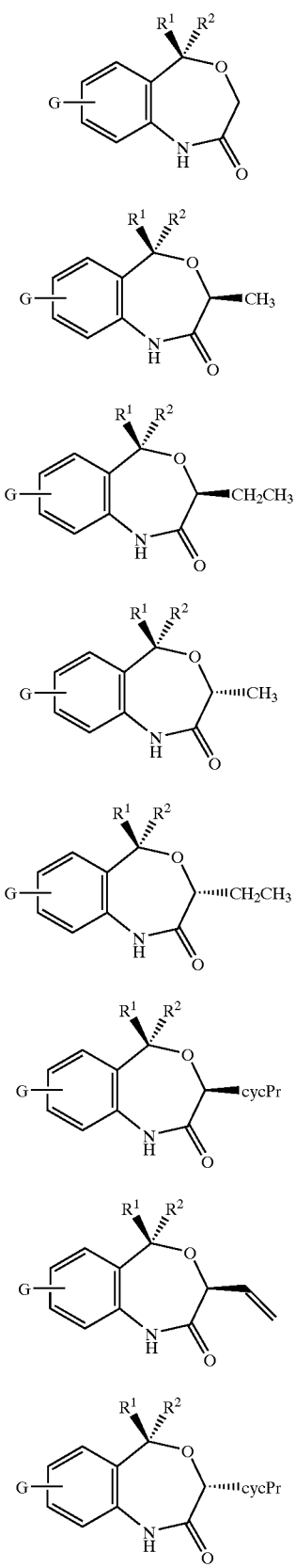

a, b, c, d, e, f, g, h

TABLE 2-continued

| Ex. # | G | R¹ | R² |
|---|---|---|---|
| 201 | 6-Cl | CF₃ | n-butyl |
| 202 | 6-Cl | CF₃ | C≡C—Et |
| 203 | 6-Cl | CF₃ | C≡C-iPr |
| 204 | 6-Cl | CF₃ | C≡C-cycPr |
| 205 | 6-Cl | CF₃ | C≡C-2-pyridyl |
| 206 | 6-Cl | CF₃ | C≡C-3-pyridyl |
| 207 | 6-Cl | CF₃ | C≡C-2-furanyl |
| 208 | 6-Cl | CF₃ | C≡C-3-furanyl |
| 209 | 6-Cl | CF₃ | C≡C-2-thienyl |
| 210 | 6-Cl | CF₃ | C≡C-3-thienyl |
| 211 | 6-Cl | CF₃ | CH=CH—Et |
| 212 | 6-Cl | CF₃ | CH=CH-iPr |
| 213 | 6-Cl | CF₃ | CH=CH-cycPr |
| 214 | 6-Cl | CF₃ | CH=CH-2-pyridyl |
| 215 | 6-Cl | CF₃ | CH=CH-3-pyridyl |
| 216 | 6-Cl | CF₃ | CH=CH-2-furanyl |
| 217 | 6-Cl | CF₃ | CH=CH-3-furanyl |
| 218 | 6-Cl | CF₃ | CH=CH-2-thienyl |
| 219 | 6-Cl | CF₃ | CH=CH-3-thienyl |
| 220 | 6-Cl | CF₃ | CH₂—C≡C-cycPr |
| 221 | 6-Cl | CF₃ | CH₂—C≡C-2-furanyl |
| 222 | 6-Cl | CF₃ | CH₂CH=CH-cycPr |
| 223 | 6-Cl | CF₃ | CH₂CH=CH-2-furanyl |
| 224 | 6-Cl | CF₃ | CH=CHCH₂-cycPr |
| 225 | 6-Cl | CF₃ | CH=CHCH₂-2-furanyl |
| 226 | 7-Cl | CF₃ | n-butyl |
| 227 | 7-Cl | CF₃ | C≡C—Et |
| 228 | 7-Cl | CF₃ | C≡C-iPr |
| 229 | 7-Cl | CF₃ | C≡C-cycPr |
| 230 | 7-Cl | CF₃ | C≡C-2-pyridyl |
| 231 | 7-Cl | CF₃ | C≡C-3-pyridyl |
| 232 | 7-Cl | CF₃ | C≡C-2-furanyl |
| 233 | 7-Cl | CF₃ | C≡C-3-furanyl |
| 234 | 7-Cl | CF₃ | C≡C-2-thienyl |
| 235 | 7-Cl | CF₃ | C≡C-3-thienyl |
| 236 | 7-Cl | CF₃ | CH=CH—Et |
| 237 | 7-Cl | CF₃ | CH=CH-iPr |
| 238 | 7-Cl | CF₃ | CH=CH-cycPr |
| 239 | 7-Cl | CF₃ | CH=CH-2-pyridyl |
| 240 | 7-Cl | CF₃ | CH=CH-3-pyridyl |
| 241 | 7-Cl | CF₃ | CH=CH-2-furanyl |
| 242 | 7-Cl | CF₃ | CH=CH-3-furanyl |
| 243 | 7-Cl | CF₃ | CH=CH-2-thienyl |
| 244 | 7-Cl | CF₃ | CH=CH-3-thienyl |
| 245 | 7-Cl | CF₃ | CH₂—C≡C-cycPr |
| 246 | 7-Cl | CF₃ | CH₂—C≡C-2-furanyl |
| 247 | 7-Cl | CF₃ | CH₂CH=CH-cycPr |
| 248 | 7-Cl | CF₃ | CH₂CH=CH-2-furanyl |
| 249 | 7-Cl | CF₃ | CH=CHCH₂-cycPr |
| 250 | 7-Cl | CF₃ | CH=CHCH₂-2-furanyl |
| 251 | 6-F | CF₃ | n-butyl |
| 252 | 6-F | CF₃ | C≡C—Et |
| 253 | 6-F | CF₃ | C≡C-iPr |
| 254 | 6-F | CF₃ | C≡C-cycPr |
| 255 | 6-F | CF₃ | C≡C-2-pyridyl |
| 256 | 6-F | CF₃ | C≡C-3-pyridyl |
| 257 | 6-F | CF₃ | C≡C-2-furanyl |
| 258 | 6-F | CF₃ | C≡C-3-furanyl |
| 259 | 6-F | CF₃ | C≡C-2-thienyl |
| 260 | 6-F | CF₃ | C≡C-3-thienyl |
| 261 | 6-F | CF₃ | CH=CH—Et |

TABLE 2-continued

| | | | |
|---|---|---|---|
| 262 | 6-F | CF$_3$ | CH=CH-iPr |
| 263 | 6-F | CF$_3$ | CH=CH-cycPr |
| 264 | 6-F | CF$_3$ | CH=CH-2-pyridyl |
| 265 | 6-F | CF$_3$ | CH=CH-3-pyridyl |
| 266 | 6-F | CF$_3$ | CH=CH-2-furanyl |
| 267 | 6-F | CF$_3$ | CH=CH-3-furanyl |
| 268 | 6-F | CF$_3$ | CH=CH-2-thienyl |
| 269 | 6-F | CF$_3$ | CH=CH-3-thienyl |
| 270 | 6-F | CF$_3$ | CH$_2$—C≡C-cycPr |
| 271 | 6-F | CF$_3$ | CH$_2$—C≡C-2-furanyl |
| 272 | 6-F | CF$_3$ | CH$_2$CH=CH-cycPr |
| 273 | 6-F | CF$_3$ | CH$_2$CH=CH-2-furanyl |
| 274 | 6-F | CF$_3$ | CH=CHCH$_2$-cycPr |
| 275 | 6-F | CF$_3$ | CH=CHCH$_2$-2-furanyl |
| 276 | 7-F | CF$_3$ | n-butyl |
| 277 | 7-F | CF$_3$ | C≡C—Et |
| 278 | 7-F | CF$_3$ | C≡C-iPr |
| 279 | 7-F | CF$_3$ | C≡C-cycPr |
| 280 | 7-F | CF$_3$ | C≡C-2-pyridyl |
| 281 | 7-F | CF$_3$ | C≡C-3-pyridyl |
| 282 | 7-F | CF$_3$ | C≡C-2-furanyl |
| 283 | 7-F | CF$_3$ | C≡C-3-furanyl |
| 284 | 7-F | CF$_3$ | C≡C-2-thienyl |
| 285 | 7-F | CF$_3$ | C≡C-3-thienyl |
| 286 | 7-F | CF$_3$ | CH=CH—Et |
| 287 | 7-F | CF$_3$ | CH=CH-iPr |
| 288 | 7-F | CF$_3$ | CH=CH-cycPr |
| 289 | 7-F | CF$_3$ | CH=CH-2-pyridyl |
| 290 | 7-F | CF$_3$ | CH=CH-3-pyridyl |
| 291 | 7-F | CF$_3$ | CH=CH-2-furanyl |
| 292 | 7-F | CF$_3$ | CH=CH-3-furanyl |
| 293 | 7-F | CF$_3$ | CH=CH-2-thienyl |
| 294 | 7-F | CF$_3$ | CH=CH-3-thienyl |
| 295 | 7-F | CF$_3$ | CH$_2$—C≡C-cycPr |
| 296 | 7-F | CF$_3$ | CH$_2$—C≡C-2-furanyl |
| 297 | 7-F | CF$_3$ | CH$_2$CH=CH-cycPr |
| 298 | 7-F | CF$_3$ | CH$_2$CH=CH-2-furanyl |
| 299 | 7-F | CF$_3$ | CH=CHCH$_2$-cycPr |
| 300 | 7-F | CF$_3$ | CH=CHCH$_2$-2-furanyl |
| 301 | 6,7-diCl | CF$_3$ | n-butyl |
| 302 | 6,7-diCl | CF$_3$ | C≡C—Et |
| 303 | 6,7-diCl | CF$_3$ | C≡C-iPr |
| 304 | 6,7-diCl | CF$_3$ | C≡C-cycPr |
| 305 | 6,7-diCl | CF$_3$ | C≡C-2-pyridyl |
| 306 | 6,7-diCl | CF$_3$ | C≡C-3-pyridyl |
| 307 | 6,7-diCl | CF$_3$ | C≡C-2-furanyl |
| 308 | 6,7-diCl | CF$_3$ | C≡C-3-furanyl |
| 309 | 6,7-diCl | CF$_3$ | C≡C-2-thienyl |
| 310 | 6,7-diCl | CF$_3$ | C≡C-3-thienyl |
| 311 | 6,7-diCl | CF$_3$ | CH=CH—Et |
| 312 | 6,7-diCl | CF$_3$ | CH=CH-iPr |
| 313 | 6,7-diCl | CF$_3$ | CH=CH-cycPr |
| 314 | 6,7-diCl | CF$_3$ | CH=CH-2-pyridyl |
| 315 | 6,7-diCl | CF$_3$ | CH=CH-3-pyridyl |
| 316 | 6,7-diCl | CF$_3$ | CH=CH-2-furanyl |
| 317 | 6,7-diCl | CF$_3$ | CH=CH-3-furanyl |
| 318 | 6,7-diCl | CF$_3$ | CH=CH-2-thienyl |
| 319 | 6,7-diCl | CF$_3$ | CH=CH-3-thienyl |
| 320 | 6,7-diCl | CF$_3$ | CH$_2$—C≡C-cycPr |
| 321 | 6,7-diCl | CF$_3$ | CH$_2$—C≡C-2-furanyl |
| 322 | 6,7-diCl | CF$_3$ | CH$_2$CH=CH-cycPr |
| 323 | 6,7-diCl | CF$_3$ | CH$_2$CH=CH-2-furanyl |
| 324 | 6,7-diCl | CF$_3$ | CH=CHCH$_2$-cycPr |
| 325 | 6,7-diCl | CF$_3$ | CH=CHCH$_2$-2-furanyl |
| 326 | 6,7-diF | CF$_3$ | n-butyl |
| 327 | 6,7-diF | CF$_3$ | C≡C—Et |
| 328 | 6,7-diF | CF$_3$ | C≡C-iPr |
| 329 | 6,7-diF | CF$_3$ | C≡C-cycPr |
| 330 | 6,7-diF | CF$_3$ | C≡C-2-pyridyl |
| 331 | 6,7-diF | CF$_3$ | C≡C-3-pyridyl |
| 332 | 6,7-diF | CF$_3$ | C≡C-2-furanyl |
| 333 | 6,7-diF | CF$_3$ | C≡C-3-furanyl |
| 334 | 6,7-diF | CF$_3$ | C≡C-2-thienyl |
| 335 | 6,7-diF | CF$_3$ | C≡C-3-thienyl |
| 336 | 6,7-diF | CF$_3$ | CH=CH—Et |
| 337 | 6,7-diF | CF$_3$ | CH=CH-iPr |
| 338 | 6,7-diF | CF$_3$ | CH=CH-cycPr |
| 339 | 6,7-diF | CF$_3$ | CH=CH-2-pyridyl |
| 340 | 6,7-diF | CF$_3$ | CH=CH-3-pyridyl |
| 341 | 6,7-diF | CF$_3$ | CH=CH-2-furanyl |
| 342 | 6,7-diF | CF$_3$ | CH=CH-3-furanyl |
| 343 | 6,7-diF | CF$_3$ | CH=CH-2-thienyl |
| 344 | 6,7-diF | CF$_3$ | CH=CH-3-thienyl |
| 345 | 6,7-diF | CF$_3$ | CH$_2$—C≡C-cycPr |
| 346 | 6,7-diF | CF$_3$ | CH$_2$—C≡C-2-furanyl |
| 347 | 6,7-diF | CF$_3$ | CH$_2$CH=CH-cycPr |
| 348 | 6,7-diF | CF$_3$ | CH$_2$CH=CH-2-furanyl |
| 349 | 6,7-diF | CF$_3$ | CH=CHCH$_2$-cycPr |
| 350 | 6,7-diF | CF$_3$ | CH=CHCH$_2$-2-furanyl |
| 351 | 6-Cl, 7-F | CF$_3$ | n-butyl |
| 352 | 6-Cl, 7-F | CF$_3$ | C≡C—Et |
| 353 | 6-Cl, 7-F | CF$_3$ | C≡C-iPr |
| 354 | 6-Cl, 7-F | CF$_3$ | C≡C-cycPr |
| 355 | 6-Cl, 7-F | CF$_3$ | C≡C-2-pyridyl |
| 356 | 6-Cl, 7-F | CF$_3$ | C≡C-3-pyridyl |
| 357 | 6-Cl, 7-F | CF$_3$ | C≡C-2-furanyl |
| 358 | 6-Cl, 7-F | CF$_3$ | C≡C-3-furanyl |
| 359 | 6-Cl, 7-F | CF$_3$ | C≡C-2-thienyl |
| 360 | 6-Cl, 7-F | CF$_3$ | C≡C-3-thienyl |
| 361 | 6-Cl, 7-F | CF$_3$ | CH=CH—Et |
| 362 | 6-Cl, 7-F | CF$_3$ | CH=CH-iPr |
| 363 | 6-Cl, 7-F | CF$_3$ | CH=CH-cycPr |
| 364 | 6-Cl, 7-F | CF$_3$ | CH=CH-2-pyridyl |
| 365 | 6-Cl, 7-F | CF$_3$ | CH=CH-3-pyridyl |
| 366 | 6-Cl, 7-F | CF$_3$ | CH=CH-2-furanyl |
| 367 | 6-Cl, 7-F | CF$_3$ | CH=CH-3-furanyl |
| 368 | 6-Cl, 7-F | CF$_3$ | CH=CH-2-thienyl |
| 369 | 6-Cl, 7-F | CF$_3$ | CH=CH-3-thienyl |
| 370 | 6-Cl, 7-F | CF$_3$ | CH$_2$—C≡C-cycPr |
| 371 | 6-Cl, 7-F | CF$_3$ | CH$_2$—C≡C-2-furanyl |
| 372 | 6-Cl, 7-F | CF$_3$ | CH$_2$CH=CH-cycPr |
| 373 | 6-Cl, 7-F | CF$_3$ | CH$_2$CH=CH-2-furanyl |
| 374 | 6-Cl, 7-F | CF$_3$ | CH=CHCH$_2$-cycPr |
| 375 | 6-Cl, 7-F | CF$_3$ | CH=CHCH$_2$-2-furanyl |
| 376 | 6-F, 7-Cl | CF$_3$ | n-butyl |
| 377 | 6-F, 7-Cl | CF$_3$ | C≡C—Et |
| 378 | 6-F, 7-Cl | CF$_3$ | C≡C-iPr |
| 379 | 6-F, 7-Cl | CF$_3$ | C≡C-cycPr |
| 380 | 6-F, 7-Cl | CF$_3$ | C≡C-2-pyridyl |
| 381. | 6-F, 7-Cl | CF$_3$ | C≡C-3-pyridyl |
| 382 | 6-F, 7-Cl | CF$_3$ | C≡C-2-furanyl |
| 383 | 6-F, 7-Cl | CF$_3$ | C≡C-3-furanyl |
| 384 | 6-F, 7-Cl | CF$_3$ | C≡C-2-thienyl |
| 385 | 6-F, 7-Cl | CF$_3$ | C≡C-3-thienyl |
| 386 | 6-F, 7-Cl | CF$_3$ | CH=CH—Et |
| 387 | 6-F, 7-Cl | CF$_3$ | CH=CH-iPr |
| 388 | 6-F, 7-Cl | CF$_3$ | CH=CH-cycPr |
| 389 | 6-F, 7-Cl | CF$_3$ | CH=CH-2-pyridyl |
| 390 | 6-F, 7-Cl | CF$_3$ | CH=CH-3-pyridyl |
| 391 | 6-F, 7-Cl | CF$_3$ | CH=CH-2-furanyl |
| 392 | 6-F, 7-Cl | CF$_3$ | CH=CH-3-furanyl |
| 393 | 6-F, 7-Cl | CF$_3$ | CH=CH-2-thienyl |
| 394 | 6-F, 7-Cl | CF$_3$ | CH=CH-3-thienyl |
| 395 | 6-F, 7-Cl | CF$_3$ | CH$_2$—C≡C-cycPr |
| 396 | 6-F, 7-Cl | CF$_3$ | CH$_2$—C≡C-2-furanyl |
| 397 | 6-F, 7-Cl | CF$_3$ | CH$_2$CH=CH-cycPr |
| 398 | 6-F, 7-Cl | CF$_3$ | CH$_2$CH=CH-2-furanyl |
| 399 | 6-F, 7-Cl | CF$_3$ | CH=CHCH$_2$-cycPr |
| 400 | 6-F, 7-Cl | CF$_3$ | CH=CHCH$_2$-2-furanyl |
| 401 | 7-CH$_3$ | CF$_3$ | n-butyl |

TABLE 2-continued

| | | | |
|---|---|---|---|
| 402 | 7-CH₃ | CF₃ | C≡C—Et |
| 403 | 7-CH₃ | CF₃ | C≡C-iPr |
| 404 | 7-CH₃ | CF₃ | C≡C-cycPr |
| 405 | 7-CH₃ | CF₃ | C≡C-2-pyridyl |
| 406 | 7-CH₃ | CF₃ | C≡C-3-pyridyl |
| 407 | 7-CH₃ | CF₃ | C≡C-2-furanyl |
| 408 | 7-CH₃ | CF₃ | C≡C-3-furanyl |
| 409 | 7-CH₃ | CF₃ | C≡C-2-thienyl |
| 410 | 7-CH₃ | CF₃ | C≡C-3-thienyl |
| 411 | 7-CH₃ | CF₃ | CH=CH—Et |
| 412 | 7-CH₃ | CF₃ | CH=CH-iPr |
| 413 | 7-CH₃ | CF₃ | CH=CH-cycPr |
| 414 | 7-CH₃ | CF₃ | CH=CH-2-pyridyl |
| 415 | 7-CH₃ | CF₃ | CH=CH-3-pyridyl |
| 416 | 7-CH₃ | CF₃ | CH=CH-2-furanyl |
| 417 | 7-CH₃ | CF₃ | CH=CH-3-furanyl |
| 418 | 7-CH₃ | CF₃ | CH=CH-2-thienyl |
| 419 | 7-CH₃ | CF₃ | CH=CH-3-thienyl |
| 420 | 7-CH₃ | CF₃ | CH₂—C≡C-cycPr |
| 421 | 7-CH₃ | CF₃ | CH₂—C≡C-2-furanyl |
| 422 | 7-CH₃ | CF₃ | CH₂CH=CH-cycPr |
| 423 | 7-CH₃ | CF₃ | CH₂CH=CH-2-furanyl |
| 424 | 7-CH₃ | CF₃ | CH=CHCH₂-cycPr |
| 425 | 7-CH₃ | CF₃ | CH=CHCH₂-2-furanyl |
| 426 | 7-OCH₃ | CF₃ | n-butyl |
| 427 | 7-OCH₃ | CF₃ | C≡C—Et |
| 428 | 7-OCH₃ | CF₃ | C≡C-iPr |
| 429 | 7-OCH₃ | CF₃ | C≡C-cycPr |
| 430 | 7-OCH₃ | CF₃ | C≡C-2-pyridyl |
| 431 | 7-OCH₃ | CF₃ | C≡C-3-pyridyl |
| 432 | 7-OCH₃ | CF₃ | C≡C-2-furanyl |
| 433 | 7-OCH₃ | CF₃ | C≡C-3-furanyl |
| 434 | 7-OCH₃ | CF₃ | C≡C-2-thienyl |
| 435 | 7-OCH₃ | CF₃ | C≡C-3-thienyl |
| 436 | 7-OCH₃ | CF₃ | CH=CH—Et |
| 437 | 7-OCH₃ | CF₃ | CH=CH-iPr |
| 438 | 7-OCH₃ | CF₃ | CH=CH-cycPr |
| 439 | 7-OCH₃ | CF₃ | CH=CH-2-pyridyl |
| 440 | 7-OCH₃ | CF₃ | CH=CH-3-pyridyl |
| 441 | 7-OCH₃ | CF₃ | CH=CH-2-furanyl |
| 442 | 7-OCH₃ | CF₃ | CH=CH-3-furanyl |
| 443 | 7-OCH₃ | CF₃ | CH=CH-2-thienyl |
| 444 | 7-OCH₃ | CF₃ | CH=CH-3-thienyl |
| 445 | 7-OCH₃ | CF₃ | CH₂—C≡C-cycPr |
| 446 | 7-OCH₃ | CF₃ | CH₂—C≡C-2-furanyl |
| 447 | 7-OCH₃ | CF₃ | CH₂CH=CH-cycPr |
| 448 | 7-OCH₃ | CF₃ | CH₂CH=CH-2-furanyl |
| 449 | 7-OCH₃ | CF₃ | CH=CHCH₂-cycPr |
| 450 | 7-OCH₃ | CF₃ | CH=CHCH₂-2-furanyl |
| 451 | 7-pyrazol-6-yl | CF₃ | n-butyl |
| 452 | 7-pyrazol-6-yl | CF₃ | C≡C—Et |
| 453 | 7-pyrazol-6-yl | CF₃ | C≡C-iPr |
| 454 | 7-pyrazol-6-yl | CF₃ | C≡C-cycPr |
| 455 | 7-pyrazol-6-yl | CF₃ | C≡C-2-pyridyl |
| 456 | 7-pyrazol-6-yl | CF₃ | C≡C-3-pyridyl |
| 457 | 7-pyrazol-6-yl | CF₃ | C≡C-2-furanyl |
| 458 | 7-pyrazol-6-yl | CF₃ | C≡C-3-furanyl |
| 459 | 7-pyrazol-6-yl | CF₃ | C≡C-2-thienyl |
| 460 | 7-pyrazol-6-yl | CF₃ | C≡C-3-thienyl |
| 461 | 7-pyrazol-6-yl | CF₃ | CH=CH—Et |
| 462 | 7-pyrazol-6-yl | CF₃ | CH=CH-iPr |
| 463 | 7-pyrazol-6-yl | CF₃ | CH=CH-cycPr |
| 464 | 7-pyrazol-6-yl | CF₃ | CH=CH-2-pyridyl |
| 465 | 7-pyrazol-6-yl | CF₃ | CH=CH-3-pyridyl |
| 466 | 7-pyrazol-6-yl | CF₃ | CH=CH-2-furanyl |
| 467 | 7-pyrazol-6-yl | CF₃ | CH=CH-3-furanyl |
| 468 | 7-pyrazol-6-yl | CF₃ | CH=CH-2-thienyl |
| 469 | 7-pyrazol-6-yl | CF₃ | CH=CH-3-thienyl |
| 470 | 7-pyrazol-6-yl | CF₃ | CH₂—C≡C-cycPr |
| 471 | 7-pyrazol-6-yl | CF₃ | CH₂—C≡C-2-furanyl |
| 472 | 7-pyrazol-6-yl | CF₃ | CH₂CH=CH-cycPr |
| 473 | 7-pyrazol-6-yl | CF₃ | CH₂CH=CH-2-furanyl |
| 474 | 7-pyrazol-6-yl | CF₃ | CH=CHCH₂-cycPr |
| 475 | 7-pyrazol-6-yl | CF₃ | CH=CHCH₂-2-furanyl |
| 476 | 6,7-OCH₂O— | CF₃ | n-butyl |
| 477 | 6,7-OCH₂O— | CF₃ | C≡C—Et |
| 478 | 6,7-OCH₂O— | CF₃ | C≡C-iPr |
| 479 | 6,7-OCH₂O— | CF₃ | C≡C-cycPr |
| 480 | 6,7-OCH₂O— | CF₃ | C≡C-2-pyridyl |
| 481 | 6,7-OCH₂O— | CF₃ | C≡C-3-pyridyl |
| 482 | 6,7-OCH₂O— | CF₃ | C≡C-2-furanyl |
| 483 | 6,7-OCH₂O— | CF₃ | C≡C-3-furanyl |
| 484 | 6,7-OCH₂O— | CF₃ | C≡C-2-thienyl |
| 485 | 6,7-OCH₂O— | CF₃ | C≡C-3-thienyl |
| 486 | 6,7-OCH₂O— | CF₃ | CH=CH—Et |
| 487 | 6,7-OCH₂O— | CF₃ | CH=CH-iPr |
| 488 | 6,7-OCH₂O— | CF₃ | CH=CH-cycPr |
| 489 | 6,7-OCH₂O— | CF₃ | CH=CH-2-pyridyl |
| 490 | 6,7-OCH₂O— | CF₃ | CH=CH-3-pyridyl |
| 491 | 6,7-OCH₂O— | CF₃ | CH=CH-2-furanyl |
| 492 | 6,7-OCH₂O— | CF₃ | CH=CH-3-furanyl |
| 493 | 6,7-OCH₂O— | CF₃ | CH=CH-2-thienyl |
| 494 | 6,7-OCH₂O— | CF₃ | CH=CH-3-thienyl |
| 495 | 6,7-OCH₂O— | CF₃ | CH₂—C≡C-cycPr |
| 496 | 6,7-OCH₂O— | CF₃ | CH₂—C≡C-2-furanyl |
| 497 | 6,7-OCH₂O— | CF₃ | CH₂CH=CH-cycPr |
| 498 | 6,7-OCH₂O— | CF₃ | CH₂CH=CH-2-furanyl |
| 499 | 6,7-OCH₂O— | CF₃ | CH=CHCH₂-cycPr |
| 500 | 6,7-OCH₂O— | CF₃ | CH=CHCH₂-2-furanyl |
| 501 | 7-CONH₂ | CF₃ | n-butyl |
| 502 | 7-CONH₂ | CF₃ | C≡C—Et |
| 503 | 7-CONH₂ | CF₃ | C≡C-iPr |
| 504 | 7-CONH₂ | CF₃ | C≡C-cycPr |
| 505 | 7-CONH₂ | CF₃ | C≡C-2-pyridyl |
| 506 | 7-CONH₂ | CF₃ | C≡C-3-pyridyl |
| 507 | 7-CONH₂ | CF₃ | C≡C-2-furanyl |
| 508 | 7-CONH₂ | CF₃ | C≡C-3-furanyl |
| 509 | 7-CONH₂ | CF₃ | C≡C-2-thienyl |
| 510 | 7-CONH₂ | CF₃ | C≡C-3-thienyl |
| 511 | 7-CONH₂ | CF₃ | CH=CH—Et |
| 512 | 7-CONH₂ | CF₃ | CH=CH-iPr |
| 513 | 7-CONH₂ | CF₃ | CH=CH-cycPr |
| 514 | 7-CONH₂ | CF₃ | CH=CH-2-pyridyl |
| 515 | 7-CONH₂ | CF₃ | CH=CH-3-pyridyl |
| 516 | 7-CONH₂ | CF₃ | CH=CH-2-furanyl |
| 517 | 7-CONH₂ | CF₃ | CH=CH-3-furanyl |
| 518 | 7-CONH₂ | CF₃ | CH=CH-2-thienyl |
| 519 | 7-CONH₂ | CF₃ | CH=CH-3-thienyl |
| 520 | 7-CONH₂ | CF₃ | CH₂—C≡C-cycPr |
| 521 | 7-CONH₂ | CF₃ | CH₂—C≡C-2-furanyl |
| 522 | 7-CONH₂ | CF₃ | CH₂CH=CH-cycPr |
| 523 | 7-CONH₂ | CF₃ | CH₂CH=CH-2-furanyl |

TABLE 2-continued

| | | | |
|---|---|---|---|
| 524 | 7-CONH$_2$ | CF$_3$ | CH=CHCH$_2$-cycPr |
| 525 | 7-CONH$_2$ | CF$_3$ | CH=CHCH$_2$-2-furanyl |
| 526 | 6-Cl | C$_2$F$_5$ | n-butyl |
| 527 | 6-Cl | C$_2$F$_5$ | C≡C—Et |
| 528 | 6-Cl | C$_2$F$_5$ | C≡C-iPr |
| 529 | 6-Cl | C$_2$F$_5$ | C≡C-cycPr |
| 530 | 6-Cl | C$_2$F$_5$ | C≡C-2-pyridyl |
| 531 | 6-Cl | C$_2$F$_5$ | C≡C-3-pyridyl |
| 532 | 6-Cl | C$_2$F$_5$ | C≡C-2-furanyl |
| 533 | 6-Cl | C$_2$F$_5$ | C≡C-3-furanyl |
| 534 | 6-Cl | C$_2$F$_5$ | C≡C-2-thienyl |
| 535 | 6-Cl | C$_2$F$_5$ | C≡C-3-thienyl |
| 536 | 6-Cl | C$_2$F$_5$ | CH=CH—Et |
| 537 | 6-Cl | C$_2$F$_5$ | CH=CH-iPr |
| 538 | 6-Cl | C$_2$F$_5$ | CH=CH-cycPr |
| 539 | 6-Cl | C$_2$F$_5$ | CH=CH-2-pyridyl |
| 540 | 6-Cl | C$_2$F$_5$ | CH=CH-3-pyridyl |
| 541 | 6-Cl | C$_2$F$_5$ | CH=CH-2-furanyl |
| 542 | 6-Cl | C$_2$F$_5$ | CH=CH-3-furanyl |
| 543 | 6-Cl | C$_2$F$_5$ | CH=CH-2-thienyl |
| 544 | 6-Cl | C$_2$F$_5$ | CH=CH-3-thienyl |
| 545 | 6-Cl | C$_2$F$_5$ | CH$_2$—C≡C-cycPr |
| 546 | 6-Cl | C$_2$F$_5$ | CH$_2$—C≡C-2-furanyl |
| 547 | 6-Cl | C$_2$F$_5$ | CH$_2$CH=CH-cycPr |
| 548 | 6-Cl | C$_2$F$_5$ | CH$_2$CH=CH-2-furanyl |
| 549 | 6-Cl | C$_2$F$_5$ | CH=CHCH$_2$-cycPr |
| 550 | 6-Cl | C$_2$F$_5$ | CH=CHCH$_2$-2-furanyl |
| 551 | 7-Cl | C$_2$F$_5$ | n-butyl |
| 552 | 7-Cl | C$_2$F$_5$ | C≡C—Et |
| 553 | 7-Cl | C$_2$F$_5$ | C≡C-iPr |
| 554 | 7-Cl | C$_2$F$_5$ | C≡C-cycPr |
| 555 | 7-Cl | C$_2$F$_5$ | C≡C-2-pyridyl |
| 556 | 7-Cl | C$_2$F$_5$ | C≡C-3-pyridyl |
| 557 | 7-Cl | C$_2$F$_5$ | C≡C-2-furanyl |
| 558 | 7-Cl | C$_2$F$_5$ | C≡C-3-furanyl |
| 559 | 7-Cl | C$_2$F$_5$ | C≡C-2-thienyl |
| 560 | 7-Cl | C$_2$F$_5$ | C≡C-3-thienyl |
| 561 | 7-Cl | C$_2$F$_5$ | CH=CH—Et |
| 562 | 7-Cl | C$_2$F$_5$ | CH=CH-iPr |
| 563 | 7-Cl | C$_2$F$_5$ | CH=CH-cycPr |
| 564 | 7-Cl | C$_2$F$_5$ | CH=CH-2-pyridyl |
| 565 | 7-Cl | C$_2$F$_5$ | CH=CH-3-pyridyl |
| 566 | 7-Cl | C$_2$F$_5$ | CH=CH-2-furanyl |
| 567 | 7-Cl | C$_2$F$_5$ | CH=CH-3-furanyl |
| 568 | 7-Cl | C$_2$F$_5$ | CH=CH-2-thienyl |
| 569 | 7-Cl | C$_2$F$_5$ | CH=CH-3-thienyl |
| 570 | 7-Cl | C$_2$F$_5$ | CH$_2$—C≡C-cycPr |
| 571 | 7-Cl | C$_2$F$_5$ | CH$_2$—C≡C-2-furanyl |
| 572 | 7-Cl | C$_2$F$_5$ | CH$_2$CH=CH-cycPr |
| 573 | 7-Cl | C$_2$F$_5$ | CH$_2$CH=CH-2-furanyl |
| 574 | 7-Cl | C$_2$F$_5$ | CH=CHCH$_2$-cycPr |
| 575 | 7-Cl | C$_2$F$_5$ | CH=CHCH$_2$-2-furanyl |
| 576 | 6-F | C$_2$F$_5$ | n-butyl |
| 577 | 6-F | C$_2$F$_5$ | C≡C—Et |
| 578 | 6-F | C$_2$F$_5$ | C≡C-iPr |
| 579 | 6-F | C$_2$F$_5$ | C≡C-cycPr |
| 580 | 6-F | C$_2$F$_5$ | C≡C-2-pyridyl |
| 581 | 6-F | C$_2$F$_5$ | C≡C-3-pyridyl |
| 582 | 6-F | C$_2$F$_5$ | C≡C-2-furanyl |
| 583 | 6-F | C$_2$F$_5$ | C≡C-3-furanyl |
| 584 | 6-F | C$_2$F$_5$ | C≡C-2-thienyl |
| 585 | 6-F | C$_2$F$_5$ | C≡C-3-thienyl |
| 586 | 6-F | C$_2$F$_5$ | CH=CH—Et |
| 587 | 6-F | C$_2$F$_5$ | CH=CH-iPr |
| 588 | 6-F | C$_2$F$_5$ | CH=CH-cycPr |
| 589 | 6-F | C$_2$F$_5$ | CH=CH-2-pyridyl |
| 590 | 6-F | C$_2$F$_5$ | CH=CH-3-pyridyl |
| 591 | 6-F | C$_2$F$_5$ | CH=CH-2-furanyl |
| 592 | 6-F | C$_2$F$_5$ | CH=CH-3-furanyl |
| 593 | 6-F | C$_2$F$_5$ | CH=CH-2-thienyl |
| 594 | 6-F | C$_2$F$_5$ | CH=CH-3-thienyl |
| 595 | 6-F | C$_2$F$_5$ | CH$_2$—C≡C-cycPr |
| 596 | 6-F | C$_2$F$_5$ | CH$_2$—C≡C-2-furanyl |
| 597 | 6-F | C$_2$F$_5$ | CH$_2$CH=CH-cycPr |
| 598 | 6-F | C$_2$F$_5$ | CH$_2$CH=CH-2-furanyl |
| 599 | 6-F | C$_2$F$_5$ | CH=CHCH$_2$-cycPr |
| 600 | 6-F | C$_2$F$_5$ | CH=CHCH$_2$-2-furanyl |
| 601 | 7-F | C$_2$F$_5$ | n-butyl |
| 602 | 7-F | C$_2$F$_5$ | C≡C—Et |
| 603 | 7-F | C$_2$F$_5$ | C≡C-iPr |
| 604 | 7-F | C$_2$F$_5$ | C≡C-cycPr |
| 605 | 7-F | C$_2$F$_5$ | C≡C-2-pyridyl |
| 606 | 7-F | C$_2$F$_5$ | C≡C-3-pyridyl |
| 607 | 7-F | C$_2$F$_5$ | C≡C-2-furanyl |
| 608 | 7-F | C$_2$F$_5$ | C≡C-3-furanyl |
| 609 | 7-F | C$_2$F$_5$ | C≡C-2-thienyl |
| 610 | 7-F | C$_2$F$_5$ | C≡C-3-thienyl |
| 611 | 7-F | C$_2$F$_5$ | CH=CH—Et |
| 612 | 7-F | C$_2$F$_5$ | CH=CH-iPr |
| 613 | 7-F | C$_2$F$_5$ | CH=CH-cycPr |
| 614 | 7-F | C$_2$F$_5$ | CH=CH-2-pyridyl |
| 615 | 7-F | C$_2$F$_5$ | CH=CH-3-pyridyl |
| 616 | 7-F | C$_2$F$_5$ | CH=CH-2-furanyl |
| 617 | 7-F | C$_2$F$_5$ | CH=CH-3-furanyl |
| 618 | 7-F | C$_2$F$_5$ | CH=CH-2-thienyl |
| 619 | 7-F | C$_2$F$_5$ | CH=CH-3-thienyl |
| 620 | 7-F | C$_2$F$_5$ | CH$_2$—C≡C-cycPr |
| 621 | 7-F | C$_2$F$_5$ | CH$_2$—C≡C-2-furanyl |
| 622 | 7-F | C$_2$F$_5$ | CH$_2$CH=CH-cycPr |
| 623 | 7-F | C$_2$F$_5$ | CH$_2$CH=CH-2-furanyl |
| 624 | 7-F | C$_2$F$_5$ | CH=CHCH$_2$-cycPr |
| 625 | 7-F | C$_2$F$_5$ | CH=CHCH$_2$-2-furanyl |
| 626 | 6,7-diCl | C$_2$F$_5$ | n-butyl |
| 627 | 6,7-diCl | C$_2$F$_5$ | C≡C—Et |
| 628 | 6,7-diCl | C$_2$F$_5$ | C≡C-iPr |
| 629 | 6,7-diCl | C$_2$F$_5$ | C≡C-cycPr |
| 630 | 6,7-diCl | C$_2$F$_5$ | C≡C-2-pyridyl |
| 631 | 6,7-diCl | C$_2$F$_5$ | C≡C-3-pyridyl |
| 632 | 6,7-diCl | C$_2$F$_5$ | C≡C-2-furanyl |
| 633 | 6,7-diCl | C$_2$F$_5$ | C≡C-3-furanyl |
| 634 | 6,7-diCl | C$_2$F$_5$ | C≡C-2-thienyl |
| 635 | 6,7-diCl | C$_2$F$_5$ | C≡C-3-thienyl |
| 636 | 6,7-diCl | C$_2$F$_5$ | CH=CH—Et |
| 637 | 6,7-diCl | C$_2$F$_5$ | CH=CH-iPr |
| 638 | 6,7-diCl | C$_2$F$_5$ | CH=CH-cycPr |
| 639 | 6,7-diCl | C$_2$F$_5$ | CH=CH-2-pyridyl |
| 640 | 6,7-diCl | C$_2$F$_5$ | CH=CH-3-pyridyl |
| 641 | 6,7-diCl | C$_2$F$_5$ | CH=CH-2-furanyl |
| 642 | 6,7-diCl | C$_2$F$_5$ | CH=CH-3-furanyl |
| 643 | 6,7-diCl | C$_2$F$_5$ | CH=CH-2-thienyl |
| 644 | 6,7-diCl | C$_2$F$_5$ | CH=CH-3-thienyl |
| 645 | 6,7-diCl | C$_2$F$_5$ | CH$_2$—C≡C-cycPr |
| 646 | 6,7-diCl | C$_2$F$_5$ | CH$_2$—C≡C-2-furanyl |
| 647 | 6,7-diCl | C$_2$F$_5$ | CH$_2$CH=CH-cycPr |
| 648 | 6,7-diCl | C$_2$F$_5$ | CH$_2$CH=CH-2-furanyl |
| 649 | 6,7-diCl | C$_2$F$_5$ | CH=CHCH$_2$-cycPr |
| 650 | 6,7-diCl | C$_2$F$_5$ | CH=CHCH$_2$-2-furanyl |
| 651 | 6,7-diF | C$_2$F$_5$ | n-butyl |
| 652 | 6,7-diF | C$_2$F$_5$ | C≡C—Et |
| 653 | 6,7-diF | C$_2$F$_5$ | C≡C-iPr |
| 654 | 6,7-diF | C$_2$F$_5$ | C≡C-cycPr |
| 655 | 6,7-diF | C$_2$F$_5$ | C≡C-2-pyridyl |
| 656 | 6,7-diF | C$_2$F$_5$ | C≡C-3-pyridyl |
| 657 | 6,7-diF | C$_2$F$_5$ | C≡C-2-furanyl |
| 658 | 6,7-diF | C$_2$F$_5$ | C≡C-3-furanyl |
| 659 | 6,7-diF | C$_2$F$_5$ | C≡C-2-thienyl |
| 660 | 6,7-diF | C$_2$F$_5$ | C≡C-3-thienyl |
| 661 | 6,7-diF | C$_2$F$_5$ | CH=CH—Et |
| 662 | 6,7-diF | C$_2$F$_5$ | CH=CH-iPr |
| 663 | 6,7-diF | C$_2$F$_5$ | CH=CH-cycPr |
| 664 | 6,7-diF | C$_2$F$_5$ | CH=CH-2-pyridyl |
| 665 | 6,7-diF | C$_2$F$_5$ | CH=CH-3-pyridyl |

TABLE 2-continued

| | | | |
|---|---|---|---|
| 666 | 6,7-diF | $C_2F_5$ | CH=CH-2-furanyl |
| 667 | 6,7-diF | $C_2F_5$ | CH=CH-3-furanyl |
| 668 | 6,7-diF | $C_2F_5$ | CH=CH-2-thienyl |
| 669 | 6,7-diF | $C_2F_5$ | CH=CH-3-thienyl |
| 670 | 6,7-diF | $C_2F_5$ | $CH_2$—C≡C-cycPr |
| 671 | 6,7-diF | $C_2F_5$ | $CH_2$—C≡C-2-furanyl |
| 672 | 6,7-diF | $C_2F_5$ | $CH_2CH$=CH-cycPr |
| 673 | 6,7-diF | $C_2F_5$ | $CH_2CH$=CH-2-furanyl |
| 674 | 6,7-diF | $C_2F_5$ | CH=$CHCH_2$-cycPr |
| 675 | 6,7-diF | $C_2F_5$ | CH=$CHCH_2$-2-furanyl |
| 676 | 6-Cl, 7-F | $C_2F_5$ | n-butyl |
| 677 | 6-Cl, 7-F | $C_2F_5$ | C≡C—Et |
| 678 | 6-Cl, 7-F | $C_2F_5$ | C≡C-iPr |
| 679 | 6-Cl, 7-F | $C_2F_5$ | C≡C-cycPr |
| 680 | 6-Cl, 7-F | $C_2F_5$ | C≡C-2-pyridyl |
| 681 | 6-Cl, 7-F | $C_2F_5$ | C≡C-3-pyridyl |
| 682 | 6-Cl, 7-F | $C_2F_5$ | C≡C-2-furanyl |
| 683 | 6-Cl, 7-F | $C_2F_5$ | C≡C-3-furanyl |
| 684 | 6-Cl, 7-F | $C_2F_5$ | C≡C-2-thienyl |
| 685 | 6-Cl, 7-F | $C_2F_5$ | C≡C-3-thienyl |
| 686 | 6-Cl, 7-F | $C_2F_5$ | CH=CH—Et |
| 687 | 6-Cl, 7-F | $C_2F_5$ | CH=CH-iPr |
| 688 | 6-Cl, 7-F | $C_2F_5$ | CH=CH-cycPr |
| 689 | 6-Cl, 7-F | $C_2F_5$ | CH=CH-2-pyridyl |
| 690 | 6-Cl, 7-F | $C_2F_5$ | CH=CH-3-pyridyl |
| 691 | 6-Cl, 7-F | $C_2F_5$ | CH=CH-2-furanyl |
| 692 | 6-Cl, 7-F | $C_2F_5$ | CH=CH-3-furanyl |
| 693 | 6-Cl, 7-F | $C_2F_5$ | CH=CH-2-thienyl |
| 694 | 6-Cl, 7-F | $C_2F_5$ | CH=CH-3-thienyl |
| 695 | 6-Cl, 7-F | $C_2F_5$ | $CH_2$—C≡C-cycPr |
| 696 | 6-Cl, 7-F | $C_2F_5$ | $CH_2$—C≡C-2-furanyl |
| 697 | 6-Cl, 7-F | $C_2F_5$ | $CH_2CH$=CH-cycPr |
| 698 | 6-Cl, 7-F | $C_2F_5$ | $CH_2CH$=CH-2-furanyl |
| 699 | 6-Cl, 7-F | $C_2F_5$ | CH=$CHCH_2$-cycPr |
| 700 | 6-Cl, 7-F | $C_2F_5$ | CH=$CHCH_2$-2-furanyl |
| 701 | 6-F, 7-Cl | $C_2F_5$ | n-butyl |
| 702 | 6-F, 7-Cl | $C_2F_5$ | C≡C—Et |
| 703 | 6-F, 7-Cl | $C_2F_5$ | C≡C-iPr |
| 704 | 6-F, 7-Cl | $C_2F_5$ | C≡C-cycPr |
| 705 | 6-F, 7-Cl | $C_2F_5$ | C≡C-2-pyridyl |
| 706 | 6-F, 7-Cl | $C_2F_5$ | C≡C-3-pyridyl |
| 707 | 6-F, 7-Cl | $C_2F_5$ | C≡C-2-furanyl |
| 708 | 6-F, 7-Cl | $C_2F_5$ | C≡C-3-furanyl |
| 709 | 6-F, 7-Cl | $C_2F_5$ | C≡C-2-thienyl |
| 710 | 6-F, 7-Cl | $C_2F_5$ | C≡C-3-thienyl |
| 711 | 6-F, 7-Cl | $C_2F_5$ | CH=CH—Et |
| 712 | 6-F, 7-Cl | $C_2F_5$ | CH=CH-iPr |
| 713 | 6-F, 7-Cl | $C_2F_5$ | CH=CH-cycPr |
| 714 | 6-F, 7-Cl | $C_2F_5$ | CH=CH-2-pyridyl |
| 715 | 6-F, 7-Cl | $C_2F_5$ | CH=CH-3-pyridyl |
| 716 | 6-F, 7-Cl | $C_2F_5$ | CH=CH-2-furanyl |
| 717 | 6-F, 7-Cl | $C_2F_5$ | CH=CH-3-furanyl |
| 718 | 6-F, 7-Cl | $C_2F_5$ | CH=CH-2-thienyl |
| 719 | 6-F, 7-Cl | $C_2F_5$ | CH=CH-3-thienyl |
| 720 | 6-F, 7-Cl | $C_2F_5$ | $CH_2$—C≡C-cycPr |
| 721 | 6-F, 7-Cl | $C_2F_5$ | $CH_2$—C≡C-2-furanyl |
| 722 | 6-F, 7-Cl | $C_2F_5$ | $CH_2CH$=CH-cycPr |
| 723 | 6-F, 7-Cl | $C_2F_5$ | $CH_2CH$=CH-2-furanyl |
| 724 | 6-F, 7-Cl | $C_2F_5$ | CH=$CHCH_2$-cycPr |
| 725 | 6-F, 7-Cl | $C_2F_5$ | CH=$CHCH_2$-2-furanyl |
| 726 | 7-$CH_3$ | $C_2F_5$ | n-butyl |
| 727 | 7-$CH_3$ | $C_2F_5$ | C≡C—Et |
| 728 | 7-$CH_3$ | $C_2F_5$ | C≡C-iPr |
| 729 | 7-$CH_3$ | $C_2F_5$ | C≡C-cycPr |
| 730 | 7-$CH_3$ | $C_2F_5$ | C≡C-2-pyridyl |
| 731 | 7-$CH_3$ | $C_2F_5$ | C≡C-3-pyridyl |
| 732 | 7-$CH_3$ | $C_2F_5$ | C≡C-2-furanyl |
| 733 | 7-$CH_3$ | $C_2F_5$ | C≡C-3-furanyl |
| 734 | 7-$CH_3$ | $C_2F_5$ | C≡C-2-thienyl |
| 735 | 7-$CH_3$ | $C_2F_5$ | C≡C-3-thienyl |
| 736 | 7-$CH_3$ | $C_2F_5$ | CH=CH—Et |
| 737 | 7-$CH_3$ | $C_2F_5$ | CH=CH-iPr |
| 738 | 7-$CH_3$ | $C_2F_5$ | CH=CH-cycPr |
| 739 | 7-$CH_3$ | $C_2F_5$ | CH=CH-2-pyridyl |
| 740 | 7-$CH_3$ | $C_2F_5$ | CH=CH-3-pyridyl |
| 741 | 7-$CH_3$ | $C_2F_5$ | CH=CH-2-furanyl |
| 742 | 7-$CH_3$ | $C_2F_5$ | CH=CH-3-furanyl |
| 743 | 7-$CH_3$ | $C_2F_5$ | CH=CH-2-thienyl |
| 744 | 7-$CH_3$ | $C_2F_5$ | CH=CH-3-thienyl |
| 745 | 7-$CH_3$ | $C_2F_5$ | $CH_2$—C≡C-cycPr |
| 746 | 7-$CH_3$ | $C_2F_5$ | $CH_2$—C≡C-2-furanyl |
| 747 | 7-$CH_3$ | $C_2F_5$ | $CH_2CH$=CH-cycPr |
| 748 | 7-$CH_3$ | $C_2F_5$ | $CH_2CH$=CH-2-furanyl |
| 749 | 7-$CH_3$ | $C_2F_5$ | CH=$CHCH_2$-cycPr |
| 750 | 7-$CH_3$ | $C_2F_5$ | CH=$CHCH_2$-2-furanyl |
| 751 | 7-$OCH_3$ | $C_2F_5$ | n-butyl |
| 752 | 7-$OCH_3$ | $C_2F_5$ | C≡C—Et |
| 753 | 7-$OCH_3$ | $C_2F_5$ | C≡C-iPr |
| 754 | 7-$OCH_3$ | $C_2F_5$ | C≡C-cycPr |
| 755 | 7-$OCH_3$ | $C_2F_5$ | C≡C-2-pyridyl |
| 756 | 7-$OCH_3$ | $C_2F_5$ | C≡C-3-pyridyl |
| 757 | 7-$OCH_3$ | $C_2F_5$ | C≡C-2-furanyl |
| 758 | 7-$OCH_3$ | $C_2F_5$ | C≡C-3-furanyl |
| 759 | 7-$OCH_3$ | $C_2F_5$ | C≡C-2-thienyl |
| 760 | 7-$OCH_3$ | $C_2F_5$ | C≡C-3-thienyl |
| 761 | 7-$OCH_3$ | $C_2F_5$ | CH=CH—Et |
| 762 | 7-$OCH_3$ | $C_2F_5$ | CH=CH-iPr |
| 763 | 7-$OCH_3$ | $C_2F_5$ | CH=CH-cycPr |
| 764 | 7-$OCH_3$ | $C_2F_5$ | CH=CH-2-pyridyl |
| 765 | 7-$OCH_3$ | $C_2F_5$ | CH=CH-3-pyridyl |
| 766 | 7-$OCH_3$ | $C_2F_5$ | CH=CH-2-furanyl |
| 767 | 7-$OCH_3$ | $C_2F_5$ | CH=CH-3-furanyl |
| 768 | 7-$OCH_3$ | $C_2F_5$ | CH=CH-2-thienyl |
| 769 | 7-$OCH_3$ | $C_2F_5$ | CH=CH-3-thienyl |
| 770 | 7-$OCH_3$ | $C_2F_5$ | $CH_2$—C≡C-cycPr |
| 771 | 7-$OCH_3$ | $C_2F_5$ | $CH_2$—C≡C-2-furanyl |
| 772 | 7-$OCH_3$ | $C_2F_5$ | $CH_2CH$=CH-cycPr |
| 773 | 7-$OCH_3$ | $C_2F_5$ | $CH_2CH$=CH-2-furanyl |
| 774 | 7-$OCH_3$ | $C_2F_5$ | CH=$CHCH_2$-cycPr |
| 775 | 7-$OCH_3$ | $C_2F_5$ | CH=$CHCH_2$-2-furanyl |
| 776 | 7-pyrazol-6-yl | $C_2F_5$ | n-butyl |
| 777 | 7-pyrazol-6-yl | $C_2F_5$ | C≡C—Et |
| 778 | 7-pyrazol-6-yl | $C_2F_5$ | C≡C-iPr |
| 779 | 7-pyrazol-6-yl | $C_2F_5$ | C≡C-cycPr |
| 780 | 7-pyrazol-6-yl | $C_2F_5$ | C≡C-2-pyridyl |
| 781 | 7-pyrazol-6-yl | $C_2F_5$ | C≡C-3-pyridyl |
| 782 | 7-pyrazol-6-yl | $C_2F_5$ | C≡C-2-furanyl |
| 783 | 7-pyrazol-6-yl | $C_2F_5$ | C≡C-3-furanyl |
| 784 | 7-pyrazol-6-yl | $C_2F_5$ | C≡C-2-thienyl |
| 785 | 7-pyrazol-6-yl | $C_2F_5$ | C≡C-3-thienyl |
| 786 | 7-pyrazol-6-yl | $C_2F_5$ | CH=CH—Et |
| 787 | 7-pyrazol-6-yl | $C_2F_5$ | CH=CH-iPr |
| 788 | 7-pyrazol-6-yl | $C_2F_5$ | CH=CH-cycPr |
| 789 | 7-pyrazol-6-yl | $C_2F_5$ | CH=CH-2-pyridyl |
| 790 | 7-pyrazol-6-yl | $C_2F_5$ | CH=CH-3-pyridyl |
| 791 | 7-pyrazol-6-yl | $C_2F_5$ | CH=CH-2-furanyl |

TABLE 2-continued

| | | | |
|---|---|---|---|
| 792 | 7-pyrazol-6-yl | $C_2F_5$ | CH=CH-3-furanyl |
| 793 | 7-pyrazol-6-yl | $C_2F_5$ | CH=CH-2-thienyl |
| 794 | 7-pyrazol-6-yl | $C_2F_5$ | CH=CH-3-thienyl |
| 795 | 7-pyrazol-6-yl | $C_2F_5$ | $CH_2$—C≡C-cycPr |
| 796 | 7-pyrazol-6-yl | $C_2F_5$ | $CH_2$—C≡C-2-furanyl |
| 797 | 7-pyrazol-6-yl | $C_2F_5$ | $CH_2$CH=CH-cycPr |
| 798 | 7-pyrazol-6-yl | $C_2F_5$ | $CH_2$CH=CH-2-furanyl |
| 799 | 7-pyrazol-6-yl | $C_2F_5$ | CH=CHCH$_2$-cycPr |
| 800 | 7-pyrazol-6-yl | $C_2F_5$ | CH=CHCH$_2$-2-furanyl |
| 801 | 6,7-OCH$_2$O— | $C_2F_5$ | n-butyl |
| 802 | 6,7-OCH$_2$O— | $C_2F_5$ | C≡C—Et |
| 803 | 6,7-OCH$_2$O— | $C_2F_5$ | C≡C-iPr |
| 804 | 6,7-OCH$_2$O— | $C_2F_5$ | C≡C-cycPr |
| 805 | 6,7-OCH$_2$O— | $C_2F_5$ | C≡C-2-pyridyl |
| 806 | 6,7-OCH$_2$O— | $C_2F_5$ | C≡C-3-pyridyl |
| 807 | 6,7-OCH$_2$O— | $C_2F_5$ | C≡C-2-furanyl |
| 808 | 6,7-OCH$_2$O— | $C_2F_5$ | C≡C-3-furanyl |
| 809 | 6,7-OCH$_2$O— | $C_2F_5$ | C≡C-2-thienyl |
| 810 | 6,7-OCH$_2$O— | $C_2F_5$ | C≡C-3-thienyl |
| 811 | 6,7-OCH$_2$O— | $C_2F_5$ | CH=CH—Et |
| 812 | 6,7-OCH$_2$O— | $C_2F_5$ | CH=CH-iPr |
| 813 | 6,7-OCH$_2$O— | $C_2F_5$ | CH=CH-cycPr |
| 814 | 6,7-OCH$_2$O— | $C_2F_5$ | CH=CH-2-pyridyl |
| 815 | 6,7-OCH$_2$O— | $C_2F_5$ | CH=CH-3-pyridyl |
| 816 | 6,7-OCH$_2$O— | $C_2F_5$ | CH=CH-2-furanyl |
| 817 | 6,7-OCH$_2$O— | $C_2F_5$ | CH=CH-3-furanyl |
| 818 | 6,7-OCH$_2$O— | $C_2F_5$ | CH=CH-2-thienyl |
| 819 | 6,7-OCH$_2$O— | $C_2F_5$ | CH=CH-3-thienyl |
| 820 | 6,7-OCH$_2$O— | $C_2F_5$ | $CH_2$—C≡C-cycPr |
| 821 | 6,7-OCH$_2$O— | $C_2F_5$ | $CH_2$—C≡C-2-furanyl |
| 822 | 6,7-OCH$_2$O— | $C_2F_5$ | $CH_2$CH=CH-cycPr |
| 823 | 6,7-OCH$_2$O— | $C_2F_5$ | $CH_2$CH=CH-2-furanyl |
| 824 | 6,7-OCH$_2$O— | $C_2F_5$ | CH=CHCH$_2$-cycPr |
| 825 | 6,7-OCH$_2$O— | $C_2F_5$ | CH=CHCH$_2$-2-furanyl |
| 826 | 7-CONH$_2$ | $C_2F_5$ | n-butyl |
| 827 | 7-CONH$_2$ | $C_2F_5$ | C≡C—Et |
| 828 | 7-CONH$_2$ | $C_2F_5$ | C≡C-iPr |
| 829 | 7-CONH$_2$ | $C_2F_5$ | C≡C-cycPr |
| 830 | 7-CONH$_2$ | $C_2F_5$ | C≡C-2-pyridyl |
| 831 | 7-CONH$_2$ | $C_2F_5$ | C≡C-3-pyridyl |
| 832 | 7-CONH$_2$ | $C_2F_5$ | C≡C-2-furanyl |
| 833 | 7-CONH$_2$ | $C_2F_5$ | C≡C-3-furanyl |
| 834 | 7-CONH$_2$ | $C_2F_5$ | C≡C-2-thienyl |
| 835 | 7-CONH$_2$ | $C_2F_5$ | C≡C-3-thienyl |
| 836 | 7-CONH$_2$ | $C_2F_5$ | CH=CH—Et |
| 837 | 7-CONH$_2$ | $C_2F_5$ | CH=CH-iPr |
| 838 | 7-CONH$_2$ | $C_2F_5$ | CH=CH-cycPr |
| 839 | 7-CONH$_2$ | $C_2F_5$ | CH=CH-2-pyridyl |
| 840 | 7-CONH$_2$ | $C_2F_5$ | CH=CH-3-pyridyl |
| 841 | 7-CONH$_2$ | $C_2F_5$ | CH=CH-2-furanyl |
| 842 | 7-CONH$_2$ | $C_2F_5$ | CH=CH-3-furanyl |
| 843 | 7-CONH$_2$ | $C_2F_5$ | CH=CH-2-thienyl |
| 844 | 7-CONH$_2$ | $C_2F_5$ | CH=CH-3-thienyl |
| 845 | 7-CONH$_2$ | $C_2F_5$ | $CH_2$—C≡C-cycPr |
| 846 | 7-CONH$_2$ | $C_2F_5$ | $CH_2$—C≡C-2-furanyl |
| 847 | 7-CONH$_2$ | $C_2F_5$ | $CH_2$CH=CH-cycPr |
| 848 | 7-CONH$_2$ | $C_2F_5$ | $CH_2$CH=CH-2-furanyl |
| 849 | 7-CONH$_2$ | $C_2F_5$ | CH=CHCH$_2$-cycPr |
| 850 | 7-CONH$_2$ | $C_2F_5$ | CH=CHCH$_2$-2-furanyl |
| 851 | 6-Cl | cycPr | n-butyl |
| 852 | 6-Cl | cycPr | C≡C—Et |
| 853 | 6-Cl | cycPr | C≡C-iPr |
| 854 | 6-Cl | cycPr | C≡C-cycPr |
| 855 | 6-Cl | cycPr | C≡C-2-pyridyl |
| 856 | 6-Cl | cycPr | C≡C-3-pyridyl |
| 857 | 6-Cl | cycPr | C≡C-2-furanyl |
| 858 | 6-Cl | cycPr | C≡C-3-furanyl |
| 859 | 6-Cl | cycPr | C≡C-2-thienyl |
| 860 | 6-Cl | cycPr | C≡C-3-thienyl |
| 861 | 6-Cl | cycPr | CH=CH—Et |
| 862 | 6-Cl | cycPr | CH=CH-iPr |
| 863 | 6-Cl | cycPr | CH=CH-cycPr |
| 864 | 6-Cl | cycPr | CH=CH-2-pyridyl |
| 865 | 6-Cl | cycPr | CH=CH-3-pyridyl |
| 866 | 6-Cl | cycPr | CH=CH-2-furanyl |
| 867 | 6-Cl | cycPr | CH=CH-3-furanyl |
| 868 | 6-Cl | cycPr | CH=CH-2-thienyl |
| 869 | 6-Cl | cycPr | CH=CH-3-thienyl |
| 870 | 6-Cl | cycPr | CH=C≡C-cycPr |
| 871 | 6-Cl | cycPr | $CH_2$—C≡C-2-furanyl |
| 872 | 6-Cl | cycPr | $CH_2$CH=CH-cycPr |
| 873 | 6-Cl | cycPr | $CH_2$CH=CH-2-furanyl |
| 874 | 6-Cl | cycPr | CH=CHCH$_2$-cycPr |
| 875 | 6-Cl | cycPr | CH=CHCH$_2$-2-furanyl |
| 876 | 7-Cl | cycPr | n-butyl |
| 877 | 7-Cl | cycPr | C≡C—Et |
| 878 | 7-Cl | cycPr | C≡C-iPr |
| 879 | 7-Cl | cycPr | C≡C-cycPr |
| 880 | 7-Cl | cycPr | C≡C-2-pyridyl |
| 881 | 7-Cl | cycPr | C≡C-3-pyridyl |
| 882 | 7-Cl | cycPr | C≡C-2-furanyl |
| 883 | 7-Cl | cycPr | C≡C-3-furanyl |
| 884 | 7-Cl | cycPr | C≡C-2-thienyl |
| 885 | 7-Cl | cycPr | C≡C-3-thienyl |
| 886 | 7-Cl | cycPr | CH=CH—Et |
| 887 | 7-Cl | cycPr | CH=CH-iPr |
| 888 | 7-Cl | cycPr | CH=CH-cycPr |
| 889 | 7-Cl | cycPr | CH=CH-2-pyridyl |
| 890 | 7-Cl | cycPr | CH=CH-3-pyridyl |
| 891 | 7-Cl | cycPr | CH=CH-2-furanyl |
| 892 | 7-Cl | cycPr | CH=CH-3-furanyl |
| 893 | 7-Cl | cycPr | CH=CH-2-thienyl |
| 894 | 7-Cl | cycPr | CH=CH-3-thienyl |
| 895 | 7-Cl | cycPr | $CH_2$—C≡C-cycPr |
| 896 | 7-Cl | cycPr | $CH_2$C≡C-2-furanyl |
| 897 | 7-Cl | cycPr | $CH_2$CH=CH-cycPr |
| 898 | 7-Cl | cycPr | $CH_2$CH=CH-2-furanyl |
| 899 | 7-Cl | cycPr | CH=CHCH$_2$-cycPr |
| 900 | 7-Cl | cycPr | CH=CHCH$_2$-2-furanyl |
| 901 | 6-F | cycPr | n-butyl |
| 902 | 6-F | cycPr | C≡C—Et |
| 903 | 6-F | cycPr | C≡C-iPr |
| 904 | 6-F | cycPr | C≡C-cycPr |
| 905 | 6-F | cycPr | C≡C-2-pyridyl |
| 906 | 6-F | cycPr | C≡C-3-pyridyl |
| 907 | 6-F | cycPr | C≡C-2-furanyl |
| 908 | 6-F | cycPr | C≡C-3-furanyl |
| 909 | 6-F | cycPr | C≡C-2-thienyl |
| 910 | 6-F | cycPr | C≡C-3-thienyl |
| 911 | 6-F | cycPr | CH=CH—Et |
| 912 | 6-F | cycPr | CH=CH-iPr |
| 913 | 6-F | cycPr | CH=CH-cycPr |
| 914 | 6-F | cycPr | CH=CH-2-pyridyl |
| 915 | 6-F | cycPr | CH=CH-3-pyridyl |
| 916 | 6-F | cycPr | CH=CH-2-furanyl |
| 917 | 6-F | cycPr | CH=CH-3-furanyl |
| 918 | 6-F | cycPr | CH=CH-2-thienyl |
| 919 | 6-F | cycPr | CH=CH-3-thienyl |
| 920 | 6-F | cycPr | $CH_2$—C≡C-cycPr |
| 921 | 6-F | cycPr | $CH_2$—C≡C-2-furanyl |
| 922 | 6-F | cycPr | $CH_2$CH=CH-cycPr |
| 923 | 6-F | cycPr | $CH_2$CH=CH-2-furanyl |
| 924 | 6-F | cycPr | CH=CHCH$_2$-cycPr |
| 925 | 6-F | cycPr | CH=CHCH$_2$-2-furanyl |

TABLE 2-continued

| | | | |
|---|---|---|---|
| 926 | 7-F | cycPr | n-butyl |
| 927 | 7-F | cycPr | C≡C—Et |
| 928 | 7-F | cycPr | C≡C-iPr |
| 929 | 7-F | cycPr | C≡C-cycPr |
| 930 | 7-F | cycPr | C≡C-2-pyridyl |
| 931 | 7-F | cycPr | C≡C-3-pyridyl |
| 932 | 7-F | cycPr | C≡C-2-furanyl |
| 933 | 7-F | cycPr | C≡C-3-furanyl |
| 934 | 7-F | cycPr | C≡C-2-thienyl |
| 935 | 7-F | cycPr | C≡C-3-thienyl |
| 936 | 7-F | cycPr | CH=CH—Et |
| 937 | 7-F | cycPr | CH=CH-iPr |
| 938 | 7-F | cycPr | CH=CH-cycPr |
| 939 | 7-F | cycPr | CH=CH-2-pyridyl |
| 940 | 7-F | cycPr | CH=CH-3-pyridyl |
| 941 | 7-F | cycPr | CH=CH-2-furanyl |
| 942 | 7-F | cycPr | CH=CH-3-furanyl |
| 943 | 7-F | cycPr | CH=CH-2-thienyl |
| 944 | 7-F | cycPr | CH=CH-3-thienyl |
| 945 | 7-F | cycPr | CH$_2$—C≡C-cycPr |
| 946 | 7-F | cycPr | CH$_2$—C≡C-2-furanyl |
| 947 | 7-F | cycPr | CH$_2$CH=CH-cycPr |
| 948 | 7-F | cycPr | CH$_2$CH=CH-2-furanyl |
| 949 | 7-F | cycPr | CH=CHCH$_2$-cycPr |
| 950 | 7-F | cycPr | CH=CHCH$_2$-2-furanyl |
| 951 | 6,7-diCl | cycPr | n-butyl |
| 952 | 6,7-diCl | cycPr | C≡C—Et |
| 953 | 6,7-diCl | cycPr | C≡C-iPr |
| 954 | 6,7-diCl | cycPr | C≡C-cycPr |
| 955 | 6,7-diCl | cycPr | C≡C-2-pyridyl |
| 956 | 6,7-diCl | cycPr | C≡C-3-pyridyl |
| 957 | 6,7-diCl | cycPr | C≡C-2-furanyl |
| 958 | 6,7-diCl | cycPr | C≡C-3-furanyl |
| 959 | 6,7-diCl | cycPr | C≡C-2-thienyl |
| 960 | 6,7-diCl | cycPr | C≡C-3-thienyl |
| 961 | 6,7-diCl | cycPr | CH=CH—Et |
| 962 | 6,7-diCl | cycPr | CH=CH-iPr |
| 963 | 6,7-diCl | cycPr | CH=CH-cycPr |
| 964 | 6,7-diCl | cycPr | CH=CH-2-pyridyl |
| 965 | 6,7-diCl | cycPr | CH=CH-3-pyridyl |
| 966 | 6,7-diCl | cycPr | CH=CH-2-furanyl |
| 967 | 6,7-diCl | cycPr | CH=CH-3-furanyl |
| 968 | 6,7-diCl | cycPr | CH=CH-2-thienyl |
| 969 | 6,7-diCl | cycPr | CH=CH-3-thienyl |
| 970 | 6,7-diCl | cycPr | CH$_2$—C≡C-cycPr |
| 971 | 6,7-diCl | cycPr | CH$_2$—C≡C-2-furanyl |
| 972 | 6,7-diCl | cycPr | CH$_2$CH=CH-cycPr |
| 973 | 6,7-diCl | cycPr | CH$_2$CH=CH-2-furanyl |
| 974 | 6,7-diCl | cycPr | CH=CHCH$_2$-cycPr |
| 975 | 6,7-diCl | cycPr | CH=CHCH$_2$-2-furanyl |
| 976 | 6,7-diF | cycPr | n-butyl |
| 977 | 6,7-diF | cycPr | C≡C—Et |
| 978 | 6,7-diF | cycPr | C≡C-iPr |
| 979 | 6,7-diF | cycPr | C≡C-cycPr |
| 980 | 6,7-diF | cycPr | C≡C-2-pyridyl |
| 981 | 6,7-diF | cycPr | C≡C-3-pyridyl |
| 982 | 6,7-diF | cycPr | C≡C-2-furanyl |
| 983 | 6,7-diF | cycPr | C≡C-3-furanyl |
| 984 | 6,7-diF | cycPr | C≡C-2-thienyl |
| 985 | 6,7-diF | cycPr | C≡C-3-thienyl |
| 986 | 6,7-diF | cycPr | CH=CH—Et |
| 987 | 6,7-diF | cycPr | CH=CH-iPr |
| 988 | 6,7-diF | cycPr | CH=CH-cycPr |
| 989 | 6,7-diF | cycPr | CH=CH-2-pyridyl |
| 990 | 6,7-diF | cycPr | CH=CH-3-pyridyl |
| 991 | 6,7-diF | cycPr | CH=CH-2-furanyl |
| 992 | 6,7-diF | cycPr | CH=CH-3-furanyl |
| 993 | 6,7-diF | cycPr | CH=CH-2-thienyl |
| 994 | 6,7-diF | cycPr | CH=CH-3-thienyl |
| 995 | 6,7-diF | cycPr | CH$_2$—C≡C-cycPr |
| 996 | 6,7-diF | cycPr | CH$_2$—C≡C-2-furanyl |
| 997 | 6,7-diF | cycPr | CH$_2$CH=CH-cycPr |
| 998 | 6,7-diF | cycPr | CH$_2$CH=CH-2-furanyl |
| 999 | 6,7-diF | cycPr | CH=CHCH$_2$-cycPr |
| 1000 | 6,7-diF | cycPr | CH=CHCH$_2$-2-furanyl |
| 1001 | 6-Cl, 7-F | cycPr | n-butyl |
| 1002 | 6-Cl, 7-F | cycPr | C≡C—Et |
| 1003 | 6-Cl, 7-F | cycPr | C≡C-iPr |
| 1004 | 6-Cl, 7-F | cycPr | C≡C-cycPr |
| 1005 | 6-Cl, 7-F | cycPr | C≡C-2-pyridyl |
| 1006 | 6-Cl, 7-F | cycPr | C≡C-3-pyridyl |
| 1007 | 6-Cl, 7-F | cycPr | C≡C-2-furanyl |
| 1008 | 6-Cl, 7-F | cycPr | C≡C-3-furanyl |
| 1009 | 6-Cl, 7-F | cycPr | C≡C-2-thienyl |
| 1010 | 6-Cl, 7-F | cycPr | C≡C-3-thienyl |
| 1011 | 6-Cl, 7-F | cycPr | CH=CH—Et |
| 1012 | 6-Cl, 7-F | cycPr | CH=CH-iPr |
| 1013 | 6-Cl, 7-F | cycPr | CH=CH-cycPr |
| 1014 | 6-Cl, 7-F | cycPr | CH=CH-2-pyridyl |
| 1015 | 6-Cl, 7-F | cycPr | CH=CH-3-pyridyl |
| 1016 | 6-Cl, 7-F | cycPr | CH=CH-2-furanyl |
| 1017 | 6-Cl, 7-F | cycPr | CH=CH-3-furanyl |
| 1018 | 6-Cl, 7-F | cycPr | CH=CH-2-thienyl |
| 1019 | 6-Cl, 7-F | cycPr | CH=CH-3-thienyl |
| 1020 | 6-Cl, 7-F | cycPr | CH$_2$—C≡C-cycPr |
| 1021 | 6-Cl, 7-F | cycPr | CH$_2$—C≡C-2-furanyl |
| 1022 | 6-Cl, 7-F | cycPr | CH$_2$CH=CH-cycPr |
| 1023 | 6-Cl, 7-F | cycPr | CH$_2$CH=CH-2-furanyl |
| 1024 | 6-Cl, 7-F | cycPr | CH=CHCH$_2$-cycPr |
| 1025 | 6-Cl, 7-F | cycPr | CH=CHCH$_2$-2-furanyl |
| 1026 | 6-F, 7-Cl | cycPr | n-butyl |
| 1027 | 6-F, 7-Cl | cycPr | C≡C—Et |
| 1028 | 6-F, 7-Cl | cycPr | C≡C-iPr |
| 1029 | 6-F, 7-Cl | cycPr | C≡C-cycPr |
| 1030 | 6-F, 7-Cl | cycPr | C≡C-2-pyridyl |
| 1031 | 6-F, 7-Cl | cycPr | C≡C-3-pyridyl |
| 1032 | 6-F, 7-Cl | cycPr | C≡C-2-furanyl |
| 1033 | 6-F, 7-Cl | cycPr | C≡C-3-furanyl |
| 1034 | 6-F, 7-Cl | cycPr | C≡C-2-thienyl |
| 1035 | 6-F, 7-Cl | cycPr | C≡C-3-thienyl |
| 1036 | 6-F, 7-Cl | cycPr | CH=CH—Et |
| 1037 | 6-F, 7-Cl | cycPr | CH=CH-iPr |
| 1038 | 6-F, 7-Cl | cycPr | CH=CH-cycPr |
| 1039 | 6-F, 7-Cl | cycPr | CH=CH-2-pyridyl |
| 1040 | 6-F, 7-Cl | cycPr | CH=CH-3-pyridyl |
| 1041 | 6-F, 7-Cl | cycPr | CH=CH-2-furanyl |
| 1042 | 6-F, 7-Cl | cycPr | CH=CH-3-furanyl |
| 1043 | 6-F, 7-Cl | cycPr | CH=CH-2-thienyl |
| 1044 | 6-F, 7-Cl | cycPr | CH=CH-3-thienyl |
| 1045 | 6-F, 7-Cl | cycPr | CH$_2$—C≡C-cycPr |
| 1046 | 6-F, 7-Cl | cycPr | CH$_2$—C≡C-2-furanyl |
| 1047 | 6-F, 7-Cl | cycPr | CH$_2$CH=CH-cycPr |
| 1048 | 6-F, 7-Cl | cycPr | CH$_2$CH=CH-2-furanyl |
| 1049 | 6-F, 7-Cl | cycPr | CH=CHCH$_2$-cycPr |
| 1050 | 6-F, 7-Cl | cycPr | CH=CHCH$_2$-2-furanyl |
| 1051 | 7-CH$_3$ | cycPr | n-butyl |
| 1052 | 7-CH$_3$ | cycPr | C≡C—Et |
| 1053 | 7-CH$_3$ | cycPr | C≡C-iPr |
| 1054 | 7-CH$_3$ | cycPr | C≡C-cycPr |
| 1055 | 7-CH$_3$ | cycPr | C≡C-2-pyridyl |
| 1056 | 7-CH$_3$ | cycPr | C≡C-3-pyridyl |
| 1057 | 7-CH$_3$ | cycPr | C≡C-2-furanyl |
| 1058 | 7-CH$_3$ | cycPr | C≡C-3-furanyl |
| 1059 | 7-CH$_3$ | cycPr | C≡C-2-thienyl |
| 1060 | 7-CH$_3$ | cycPr | C≡C-3-thienyl |
| 1061 | 7-CH$_3$ | cycPr | CH=CH—Et |
| 1062 | 7-CH$_3$ | cycPr | CH=CH-iPr |
| 1063 | 7-CH$_3$ | cycPr | CH=CH-cycPr |
| 1064 | 7-CH$_3$ | cycPr | CH=CH-2-pyridyl |
| 1065 | 7-CH$_3$ | cycPr | CH=CH-3-pyridyl |
| 1066 | 7-CH$_3$ | cycPr | CH=CH-2-furanyl |
| 1067 | 7-CH$_3$ | cycPr | CH=CH-3-furanyl |
| 1068 | 7-CH$_3$ | cycPr | CH=CH-2-thienyl |

TABLE 2-continued

| | | | |
|---|---|---|---|
| 1069 | 7-CH₃ | cycPr | CH=CH-3-thienyl |
| 1070 | 7-CH₃ | cycPr | CH₂—C≡C-cycPr |
| 1071 | 7-CH₃ | cycPr | CH₂—C≡C-2-furanyl |
| 1072 | 7-CH₃ | cycPr | CH₂CH=CH-cycPr |
| 1073 | 7-CH₃ | cycPr | CH₂CH=CH-2-furanyl |
| 1074 | 7-CH₃ | cycPr | CH=CHCH₂-cycPr |
| 1075 | 7-CH₃ | cycPr | CH=CHCH₂-2-furanyl |
| 1076 | 7-OCH₃ | cycPr | n-butyl |
| 1077 | 7-OCH₃ | cycPr | C≡C—Et |
| 1078 | 7-OCH₃ | cycPr | C≡C-iPr |
| 1079 | 7-OCH₃ | cycPr | C≡C-cycPr |
| 1080 | 7-OCH₃ | cycPr | C≡C-2-pyridyl |
| 1081 | 7-OCH₃ | cycPr | C≡C-3-pyridyl |
| 1082 | 7-OCH₃ | cycPr | C≡C-2-furanyl |
| 1083 | 7-OCH₃ | cycPr | C≡C-3-furanyl |
| 1084 | 7-OCH₃ | cycPr | C≡C-2-thienyl |
| 1085 | 7-OCH₃ | cycPr | C≡C-3-thienyl |
| 1086 | 7-OCH₃ | cycPr | CH=CH—Et |
| 1087 | 7-OCH₃ | cycPr | CH=CH-iPr |
| 1088 | 7-OCH₃ | cycPr | CH=CH-cycPr |
| 1089 | 7-OCH₃ | cycPr | CH=CH-2-pyridyl |
| 1090 | 7-OCH₃ | cycPr | CH=CH-3-pyridyl |
| 1091 | 7-OCH₃ | cycPr | CH=CH-2-furanyl |
| 1092 | 7-OCH₃ | cycPr | CH=CH-3-furanyl |
| 1093 | 7-OCH₃ | cycPr | CH=CH-2-thienyl |
| 1094 | 7-OCH₃ | cycPr | CH=CH-3-thienyl |
| 1095 | 7-OCH₃ | cycPr | CH₂—C≡C-cycPr |
| 1096 | 7-OCH₃ | cycPr | CH₂—C≡C-2-furanyl |
| 1097 | 7-OCH₃ | cycPr | CH₂CH=CH-cycPr |
| 1098 | 7-OCH₃ | cycPr | CH₂CH=CH-2-furanyl |
| 1099 | 7-OCH₃ | cycPr | CH=CHCH₂-cycPr |
| 1100 | 7-OCH₃ | cycPr | CH=CHCH₂-2-furanyl |
| 1101 | 7-pyrazol-6-yl | cycPr | n-butyl |
| 1102 | 7-pyrazol-6-yl | cycPr | C≡C—Et |
| 1103 | 7-pyrazol-6-yl | cycPr | C≡C-iPr |
| 1104 | 7-pyrazol-6-yl | cycPr | C≡C-cycPr |
| 1105 | 7-pyrazol-6-yl | cycPr | C≡C-2-pyridyl |
| 1106 | 7-pyrazol-6-yl | cycPr | C≡C-3-pyridyl |
| 1107 | 7-pyrazol-6-yl | cycPr | C≡C-2-furanyl |
| 1108 | 7-pyrazol-6-yl | cycPr | C≡C-3-furanyl |
| 1109 | 7-pyrazol-6-yl | cycPr | C≡C-2-thienyl |
| 1110 | 7-pyrazol-6-yl | cycPr | C≡C-3-thienyl |
| 1111 | 7-pyrazol-6-yl | cycPr | CH=CH—Et |
| 1112 | 7-pyrazol-6-yl | cycPr | CH=CH-iPr |
| 1113 | 7-pyrazol-6-yl | cycPr | CH=CH-cycPr |
| 1114 | 7-pyrazol-6-yl | cycPr | CH=CH-2-pyridyl |
| 1115 | 7-pyrazol-6-yl | cycPr | CH=CH-3-pyridyl |
| 1116 | 7-pyrazol-6-yl | cycPr | CH=CH-2-furanyl |
| 1117 | 7-pyrazol-6-yl | cycPr | CH=CH-3-furanyl |
| 1118 | 7-pyrazol-6-yl | cycPr | CH=CH-2-thienyl |
| 1119 | 7-pyrazol-6-yl | cycPr | CH=CH-3-thienyl |
| 1120 | 7-pyrazol-6-yl | cycPr | CH₂—C≡C-cycPr |
| 1121 | 7-pyrazol-6-yl | cycPr | CH₂—C≡C-2-furanyl |
| 1122 | 7-pyrazol-6-yl | cycPr | CH₂CH=CH-cycPr |
| 1123 | 7-pyrazol-6-yl | cycPr | CH₂—CH=CH-2-furanyl |
| 1124 | 7-pyrazol-6-yl | cycPr | CH=CHCH₂-cycPr |
| 1125 | 7-pyrazol-6-yl | cycPr | CH=CHCH₂-2-furanyl |
| 1126 | 6,7-OCH₂O— | cycPr | n-butyl |
| 1127 | 6,7-OCH₂O— | cycPr | C≡C—Et |
| 1128 | 6,7-OCH₂O— | cycPr | C≡C-iPr |
| 1129 | 6,7-OCH₂O— | cycPr | C≡C-cycPr |
| 1130 | 6,7-OCH₂O— | cycPr | C≡C-2-pyridyl |
| 1131 | 6,7-OCH₂O— | cycPr | C≡C-3-pyridyl |
| 1132 | 6,7-OCH₂O— | cycPr | C≡C-2-furanyl |
| 1133 | 6,7-OCH₂O— | cycPr | C≡C-3-furanyl |
| 1134 | 6,7-OCH₂O— | cycPr | C≡C-2-thienyl |
| 1135 | 6,7-OCH₂O— | cycPr | C≡C-3-thienyl |
| 1136 | 6,7-OCH₂O— | cycPr | CH=CH—Et |
| 1137 | 6,7-OCH₂O— | cycPr | CH=CH-iPr |
| 1138 | 6,7-OCH₂O— | cycPr | CH=CH-cycPr |
| 1139 | 6,7-OCH₂O— | cycPr | CH=CH-2-pyridyl |
| 1140 | 6,7-OCH₂O— | cycPr | CH=CH-3-pyridyl |
| 1141 | 6,7-OCH₂O— | cycPr | CH=CH-2-furanyl |
| 1142 | 6,7-OCH₂O— | cycPr | CH=CH-3-furanyl |
| 1143 | 6,7-OCH₂O— | cycPr | CH=CH-2-thienyl |
| 1144 | 6,7-OCH₂O— | cycPr | CH=CH-3-thienyl |
| 1145 | 6,7-OCH₂O— | cycPr | CH₂—C≡C-cycPr |
| 1146 | 6,7-OCH₂O— | cycPr | CH₂—C≡C-2-furanyl |
| 1147 | 6,7-OCH₂O— | cycPr | CH₂CH=CH-cycPr |
| 1148 | 6,7-OCH₂O— | cycPr | CH₂CH=CH-2-furanyl |
| 1149 | 6,7-OCH₂O— | cycPr | CH=CHCH₂-cycPr |
| 1150 | 6,7-OCH₂O— | cycPr | CH=CHCH₂-2-furanyl |
| 1151 | 6,7-OCH₂O— | cycPr | n-butyl |
| 1152 | 7-CONH₂ | cycPr | C≡C—Et |
| 1153 | 7-CONH₂ | cycPr | C≡C-iPr |
| 1154 | 7-CONH₂ | cycPr | C≡C-cycPr |
| 1155 | 7-CONH₂ | cycPr | C≡C-2-pyridyl |
| 1156 | 7-CONH₂ | cycPr | C≡C-3-pyridyl |
| 1157 | 7-CONH₂ | cycPr | C≡C-2-furanyl |
| 1158 | 7-CONH₂ | cycPr | C≡C-3-furanyl |
| 1159 | 7-CONH₂ | cycPr | C≡C-2-thienyl |
| 1160 | 7-CONH₂ | cycPr | C≡C-3-thienyl |
| 1161 | 7-CONH₂ | cycPr | CH=CH—Et |
| 1162 | 7-CONH₂ | cycPr | CH=CH-iPr |
| 1163 | 7-CONH₂ | cycPr | CH=CH-cycPr |
| 1164 | 7-CONH₂ | cycPr | CH=CH-2-pyridyl |
| 1165 | 7-CONH₂ | cycPr | CH=CH-3-pyridyl |
| 1166 | 7-CONH₂ | cycPr | CH=CH-2-furanyl |
| 1167 | 7-CONH₂ | cycPr | CH=CH-3-furanyl |
| 1168 | 7-CONH₂ | cycPr | CH=CH-2-thienyl |
| 1169 | 7-CONH₂ | cycPr | CH=CH-3-thienyl |
| 1170 | 7-CONH₂ | cycPr | CH₂—C≡C-cycPr |
| 1171 | 7-CONH₂ | cycPr | CH₂—C≡C-2-furanyl |
| 1172 | 7-CONH₂ | cycPr | CH₂CH=CH-cycPr |
| 1173 | 7-CONH₂ | cycPr | CH₂CH=CH-2-furanyl |
| 1174 | 7-CONH₂ | cycPr | CH=CHCH₂-cycPr |
| 1175 | 7-CONH₂ | cycPr | CH=CHCH₂-2-furanyl |

*Unless otherwise noted, stereochemistry is (+/−) and in $R^2$, all double bonds are trans.

TABLE 3

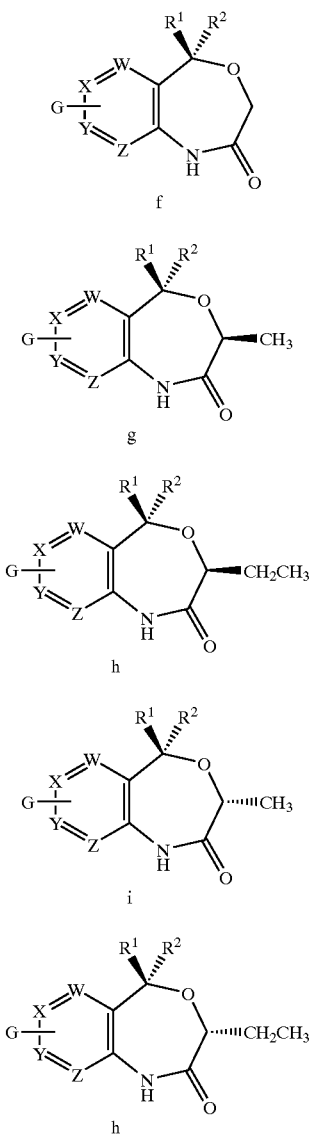

| Ex. # | W | X | Y | Z | R¹ | R² |
|---|---|---|---|---|---|---|
| 2001 | CH | CCl | CH | N | CF₃ | C≡C-nPr |
| 2002 | CH | CCl | CH | N | CF₃ | C≡C-Bu |
| 2003 | CH | CCl | CH | N | CF₃ | C≡C-iBu |
| 2004 | CH | CCl | CH | N | CF₃ | C≡C-tBu |
| 2005 | CH | CCl | CH | N | CF₃ | C≡C-Et |
| 2006 | CH | CCl | CH | N | CF₃ | C≡C-Me |
| 2007 | CH | CCl | CH | N | CF₃ | C≡C-Ph |
| 2008 | CH | CCl | CH | N | CF₃ | C≡C-2-Pyridyl |
| 2009 | CH | CCl | CH | N | CF₃ | C≡C-3-Pyridyl |
| 2010 | CH | CCl | CH | N | CF₃ | C≡C-4-Pyridyl |
| 2011 | CH | CCl | CH | N | CF₃ | C≡C-2-furanyl |
| 2012 | CH | CCl | CH | N | CF₃ | C≡C-3-furanyl |
| 2013 | CH | CCl | CH | N | CF₃ | C≡C-2-thienyl |
| 2014 | CH | CCl | CH | N | CF₃ | C≡C-3-thienyl |
| 2015 | CH | CCl | CH | N | CF₃ | CH=CH-cycPr |
| 2016 | CH | CCl | CH | N | CF₃ | CH=CH-iPr |
| 2017 | CH | CCl | CH | N | CF₃ | CH=CH-nPr |
| 2018 | CH | CCl | CH | N | CF₃ | CH=CH-Bu |
| 2019 | CH | CCl | CH | N | CF₃ | CH=CH-iBu |
| 2020 | CH | CCl | CH | N | CF₃ | CH=CH-tBu |
| 2021 | CH | CCl | CH | N | CF₃ | CH=CH-Et |
| 2022 | CH | CCl | CH | N | CF₃ | CH=CH-Me |
| 2023 | CH | CCl | CH | N | CF₃ | CH=CH-Ph |
| 2024 | CH | CCl | CH | N | CF₃ | CH=CH-2-Pyridyl |
| 2025 | CH | CCl | CH | N | CF₃ | CH=CH-3-Pyridyl |
| 2026 | CH | CCl | CH | N | CF₃ | CH=CH-4-Pyridyl |
| 2027 | CH | CCl | CH | N | CF₃ | CH=CH-2-furanyl |
| 2028 | CH | CCl | CH | N | CF₃ | CH=CH-3-furanyl |
| 2029 | CH | CCl | CH | N | CF₃ | CH=CH-2-thienyl |
| 2030 | CH | CCl | CH | N | CF₃ | CH=CH-3-thienyl |
| 2031 | CH | CCl | CH | N | CF₃ | CH₂CH₂CH₂CH₂CH₃ |
| 2032 | CH | CCl | CH | N | CF₃ | CH₂CH₂CH(CH₃)₂ |
| 2033 | CH | CCl | CH | N | CF₃ | CH₂CH₂CH₂CH₃ |
| 2034 | CH | CCl | CH | N | CF₃ | CH₂CH₂CH₃ |
| 2035 | CH | CCl | CH | N | CF₃ | CH₂CH₂-cycPr |
| 2036 | CH | CCl | CH | N | CF₃ | CH₂CH₂-tBu |
| 2037 | CH | CCl | CH | N | CF₃ | CH₂CH₂-2-Pyridyl |
| 2038 | CH | CCl | CH | N | CF₃ | CH₂CH₂-3-Pyridyl |
| 2039 | CH | CCl | CH | N | CF₃ | CH₂CH₂-4-Pyridyl |
| 2040 | CH | CCl | CH | N | CF₃ | CH₂CH₂-2-furanyl |
| 2041 | CH | CCl | CH | N | CF₃ | CH₂CH₂-3-furanyl |
| 2042 | CH | CCl | CH | N | CF₃ | CH₂CH₂-2-thienyl |
| 2043 | CH | CCl | CH | N | CF₃ | CH₂CH₂-3-thienyl |
| 2044 | CH | C(OCH₃) | CH | N | CF₃ | C≡C-cycPr |
| 2045 | CH | C(OCH₃) | CH | N | CF₃ | C≡C-iPr |
| 2046 | CH | C(OCH₃) | CH | N | CF₃ | C≡C-nPr |
| 2047 | CH | C(OCH₃) | CH | N | CF₃ | C≡C-Bu |
| 2048 | CH | C(OCH₃) | CH | N | CF₃ | C≡C-iBu |
| 2049 | CH | C(OCH₃) | CH | N | CF₃ | C≡C-tBu |
| 2050 | CH | C(OCH₃) | CH | N | CF₃ | C≡C-Et |
| 2051 | CH | C(OCH₃) | CH | N | CF₃ | C≡C-Me |
| 2052 | CH | C(OCH₃) | CH | N | CF₃ | C≡C-Ph |
| 2053 | CH | C(OCH₃) | CH | N | CF₃ | C≡C-2-Pyridyl |
| 2054 | CH | C(OCH₃) | CH | N | CF₃ | C≡C-3-Pyridyl |
| 2055 | CH | C(OCH₃) | CH | N | CF₃ | C≡C-4-Pyridyl |
| 2056 | CH | C(OCH₃) | CH | N | CF₃ | C≡C-2-furanyl |
| 2057 | CH | C(OCH₃) | CH | N | CF₃ | C≡C-3-furanyl |
| 2058 | CH | C(OCH₃) | CH | N | CF₃ | C≡C-2-thienyl |
| 2059 | CH | C(OCH₃) | CH | N | CF₃ | C≡C-3-thienyl |
| 2060 | CH | C(OCH₃) | CH | N | CF₃ | CH=CH-cycPr |
| 2061 | CH | C(OCH₃) | CH | N | CF₃ | CH=CH-iPr |
| 2062 | CH | C(OCH₃) | CH | N | CF₃ | CH=CH-nPr |
| 2063 | CH | C(OCH₃) | CH | N | CF₃ | CH=CH-Bu |
| 2064 | CH | C(OCH₃) | CH | N | CF₃ | CH=CH-iBu |
| 2065 | CH | C(OCH₃) | CH | N | CF₃ | CH=CH-tBu |
| 2066 | CH | C(OCH₃) | CH | N | CF₃ | CH=CH-Et |
| 2067 | CH | C(OCH₃) | CH | N | CF₃ | CH=CH-Me |
| 2068 | CH | C(OCH₃) | CH | N | CF₃ | CH=CH-Ph |
| 2069 | CH | C(OCH₃) | CH | N | CF₃ | CH=CH-2-Pyridyl |
| 2070 | CH | C(OCH₃) | CH | N | CF₃ | CH=CH-3-Pyridyl |
| 2071 | CH | C(OCH₃) | CH | N | CF₃ | CH=CH-4-Pyridyl |
| 2072 | CH | C(OCH₃) | CH | N | CF₃ | CH=CH-2-furanyl |
| 2073 | CH | C(OCH₃) | CH | N | CF₃ | CH=CH-3-furanyl |
| 2074 | CH | C(OCH₃) | CH | N | CF₃ | CH=CH-2-thienyl |
| 2075 | CH | C(OCH₃) | CH | N | CF₃ | CH=CH-3-thienyl |
| 2076 | CH | C(OCH₃) | CH | N | CF₃ | CH₂CH₂CH₂CH₂CH₃ |
| 2077 | CH | C(OCH₃) | CH | N | CF₃ | CH₂CH₂CH(CH₃)₂ |
| 2078 | CH | C(OCH₃) | CH | N | CF₃ | CH₂CH₂CH₂CH₃ |
| 2079 | CH | C(OCH₃) | CH | N | CF₃ | CH₂CH₂CH₃ |
| 2080 | CH | C(OCH₃) | CH | N | CF₃ | CH₂CH₂-cycPr |
| 2081 | CH | C(OCH₃) | CH | N | CF₃ | CH₂CH₂-tBu |
| 2082 | CH | C(OCH₃) | CH | N | CF₃ | CH₂CH₂-Ph |
| 2083 | CH | C(OCH₃) | CH | N | CF₃ | CH₂CH₂-2-Pyridyl |
| 2084 | CH | C(OCH₃) | CH | N | CF₃ | CH₂CH₂-3-Pyridyl |
| 2085 | CH | C(OCH₃) | CH | N | CF₃ | CH₂CH₂-4-Pyridyl |
| 2086 | CH | C(OCH₃) | CH | N | CF₃ | CH₂CH₂-2-furanyl |
| 2087 | CH | C(OCH₃) | CH | N | CF₃ | CH₂CH₂-3-furanyl |
| 2088 | CH | C(OCH₃) | CH | N | CF₃ | CH₂CH₂-2-thienyl |
| 2089 | CH | C(OCH₃) | CH | N | CF₃ | CH₂CH₂-3-thienyl |
| 2090 | CH | CH | CH | N | CF₃ | C≡C-cycPr |
| 2091 | CH | CH | CH | N | CF₃ | C≡C-iPr |
| 2092 | CH | CH | CH | N | CF₃ | C≡C-nPr |
| 2093 | CH | CH | CH | N | CF₃ | C≡C-Et |
| 2094 | CH | CH | CH | N | CF₃ | C≡C-3-Pyridyl |
| 2095 | CH | CH | CH | N | CF₃ | C≡C-2-furanyl |
| 2096 | CH | CH | CH | N | CF₃ | C≡C-3-furanyl |
| 2097 | CH | CH | CH | N | CF₃ | C≡C-2-thienyl |
| 2098 | CH | CH | CH | N | CF₃ | C≡C-3-thienyl |
| 2099 | CH | CCl | N | CH | CF₃ | C≡C-iPr |
| 2100 | CH | CCl | N | CH | CF₃ | C≡C-nPr |
| 2101 | CH | CCl | N | CH | CF₃ | C≡C-Bu |

TABLE 3-continued

| | | | | | | |
|---|---|---|---|---|---|---|
| 2102 | CH | CCl | N | CH | CF$_3$ | C≡C-iBu |
| 2103 | CH | CCl | N | CH | CF$_3$ | C≡C-tBu |
| 2104 | CH | CCl | N | CH | CF$_3$ | C≡C-Et |
| 2105 | CH | CCl | N | CH | CF$_3$ | C≡C-Me |
| 2106 | CH | CCl | N | CH | CF$_3$ | C≡C-Ph |
| 2107 | CH | CCl | N | CH | CF$_3$ | C≡C-2-Pyridyl |
| 2108 | CH | CCl | N | CH | CF$_3$ | C≡C-3-Pyridyl |
| 2109 | CH | CCl | N | CH | CF$_3$ | C≡C-4-Pyridyl |
| 2110 | CH | CCl | N | CH | CF$_3$ | C≡C-2-furanyl |
| 2111 | CH | CCl | N | CH | CF$_3$ | C≡C-3-furanyl |
| 2112 | CH | CCl | N | CH | CF$_3$ | C≡C-2-thienyl |
| 2113 | CH | CCl | N | CH | CF$_3$ | C≡C-3-thienyl |
| 2114 | CH | CCl | N | CH | CF$_3$ | CH=CH-cycPr |
| 2115 | CH | CCl | N | CH | CF$_3$ | CH=CH-iPr |
| 2116 | CH | CCl | N | CH | CF$_3$ | CH=CH-nPr |
| 2117 | CH | CCl | N | CH | CF$_3$ | CH=CH-Bu |
| 2118 | CH | CCl | N | CH | CF$_3$ | CH=CH-iBu |
| 2119 | CH | CCl | N | CH | CF$_3$ | CH=CH-tBu |
| 2120 | CH | CCl | N | CH | CF$_3$ | CH=CH-Et |
| 2121 | CH | CCl | N | CH | CF$_3$ | CH=CH-Me |
| 2122 | CH | CCl | N | CH | CF$_3$ | CH=CH-Ph |
| 2123 | CH | CCl | N | CH | CF$_3$ | CH=CH-2-Pyridyl |
| 2124 | CH | CCl | N | CH | CF$_3$ | CH=CH-3-Pyridyl |
| 2125 | CH | CCl | N | CH | CF$_3$ | CH=CH-4-Pyridyl |
| 2126 | CH | CCl | N | CH | CF$_3$ | CH=CH-2-furanyl |
| 2127 | CH | CCl | N | CH | CF$_3$ | CH=CH-3-furanyl |
| 2128 | CH | CCl | N | CH | CF$_3$ | CH=CH-2-thienyl |
| 2129 | CH | CCl | N | CH | CF$_3$ | CH=CH-3-thienyl |
| 2130 | CH | CCl | N | CH | CF$_3$ | CH$_2$CH$_2$CH$_2$CH$_2$CH$_3$ |
| 2131 | CH | CCl | N | CH | CF$_3$ | CH$_2$CH$_2$CH(CH$_3$)$_2$ |
| 2132 | CH | CCl | N | CH | CF$_3$ | CH$_2$CH$_2$CH$_2$CH$_3$ |
| 2133 | CH | CCl | N | CH | CF$_3$ | CH$_2$CH$_2$CH$_3$ |
| 2134 | CH | CCl | N | CH | CF$_3$ | CH$_2$CH$_2$-cycPr |
| 2135 | CH | CCl | N | CH | CF$_3$ | CH$_2$CH$_2$-tBu |
| 2136 | CH | CCl | N | CH | CF$_3$ | CH$_2$CH$_2$-Ph |
| 2137 | CH | CCl | N | CH | CF$_3$ | CH$_2$CH$_2$-2-Pyridyl |
| 2138 | CH | CCl | N | CH | CF$_3$ | CH$_2$CH$_2$-3-Pyridyl |
| 2139 | CH | CCl | N | CH | CF$_3$ | CH$_2$CH$_2$-4-Pyridyl |
| 2140 | CH | CCl | N | CH | CF$_3$ | CH$_2$CH$_2$-2-furanyl |
| 2141 | CH | CCl | N | CH | CF$_3$ | CH$_2$CH$_2$-3-furanyl |
| 2142 | CH | CCl | N | CH | CF$_3$ | CH$_2$CH$_2$-2-thienyl |
| 2143 | CH | CCl | N | CH | CF$_3$ | CH$_2$CH$_2$-3-thienyl |
| 2144 | CH | C(OCH$_3$) | N | CH | CF$_3$ | C≡C-iPr |
| 2145 | CH | C(OCH$_3$) | N | CH | CF$_3$ | C≡C-nPr |
| 2146 | CH | C(OCH$_3$) | N | CH | CF$_3$ | C≡C-Bu |
| 2147 | CH | C(OCH$_3$) | N | CH | CF$_3$ | C≡C-iBu |
| 2148 | CH | C(OCH$_3$) | N | CH | CF$_3$ | C≡C-tBu |
| 2149 | CH | C(OCH$_3$) | N | CH | CF$_3$ | C≡C-Et |
| 2150 | CH | C(OCH$_3$) | N | CH | CF$_3$ | C≡C-Me |
| 2151 | CH | C(OCH$_3$) | N | CH | CF$_3$ | C≡C-Ph |
| 2152 | CH | C(OCH$_3$) | N | CH | CF$_3$ | C≡C-2-Pyridyl |
| 2153 | CH | C(OCH$_3$) | N | CH | CF$_3$ | C≡C-3-Pyridyl |
| 2154 | CH | C(OCH$_3$) | N | CH | CF$_3$ | C≡C-4-Pyridyl |
| 2155 | CH | C(OCH$_3$) | N | CH | CF$_3$ | C≡C-2-furanyl |
| 2156 | CH | C(OCH$_3$) | N | CH | CF$_3$ | C≡C-3-furanyl |
| 2157 | CH | C(OCH$_3$) | N | CH | CF$_3$ | C≡C-2-thienyl |
| 2158 | CH | C(OCH$_3$) | N | CH | CF$_3$ | C≡C-3-thienyl |
| 2159 | CH | C(OCH$_3$) | N | CH | CF$_3$ | CH=CH-cycPr |
| 2160 | CH | C(OCH$_3$) | N | CH | CF$_3$ | CH=CH-iPr |
| 2161 | CH | C(OCH$_3$) | N | CH | CF$_3$ | CH=CH-nPr |
| 2162 | CH | C(OCH$_3$) | N | CH | CF$_3$ | CH=CH-Bu |
| 2163 | CH | C(OCH$_3$) | N | CH | CF$_3$ | CH=CH-iBu |
| 2164 | CH | C(OCH$_3$) | N | CH | CF$_3$ | CH=CH-tBu |
| 2165 | CH | C(OCH$_3$) | N | CH | CF$_3$ | CH=CH-Et |
| 2166 | CH | C(OCH$_3$) | N | CH | CF$_3$ | CH=CH-Me |
| 2167 | CH | C(OCH$_3$) | N | CH | CF$_3$ | CH=CH-Ph |
| 2168 | CH | C(OCH$_3$) | N | CH | CF$_3$ | CH=CH-2-Pyridyl |
| 2169 | CH | C(OCH$_3$) | N | CH | CF$_3$ | CH=CH-3-Pyridyl |
| 2170 | CH | C(OCH$_3$) | N | CH | CF$_3$ | CH=CH-4-Pyridyl |
| 2171 | CH | C(OCH$_3$) | N | CH | CF$_3$ | CH=CH-2-furanyl |
| 2172 | CH | C(OCH$_3$) | N | CH | CF$_3$ | CH=CH-3-furanyl |
| 2173 | CH | C(OCH$_3$) | N | CH | CF$_3$ | CH=CH-2-thienyl |
| 2174 | CH | C(OCH$_3$) | N | CH | CF$_3$ | CH=CH-3-thienyl |
| 2175 | CH | C(OCH$_3$) | N | CH | CF$_3$ | CH$_2$CH$_2$CH$_2$CH$_2$CH$_3$ |
| 2176 | CH | C(OCH$_3$) | N | CH | CF$_3$ | CH$_2$CH$_2$CH(CH$_3$)$_2$ |
| 2177 | CH | C(OCH$_3$) | N | CH | CF$_3$ | CH$_2$CH$_2$CH$_2$CH$_3$ |
| 2178 | CH | C(OCH$_3$) | N | CH | CF$_3$ | CH$_2$CH$_2$CH$_3$ |
| 2179 | CH | C(OCH$_3$) | N | CH | CF$_3$ | CH$_2$CH$_2$-cycPr |
| 2180 | CH | C(OCH$_3$) | N | CH | CF$_3$ | CH$_2$CH$_2$-tBu |
| 2181 | CH | C(OCH$_3$) | N | CH | CF$_3$ | CH$_2$CH$_2$-Ph |
| 2182 | CH | C(OCH$_3$) | N | CH | CF$_3$ | CH$_2$CH$_2$-2-Pyridyl |
| 2183 | CH | C(OCH$_3$) | N | CH | CF$_3$ | CH$_2$CH$_2$-3-Pyridyl |
| 2184 | CH | C(OCH$_3$) | N | CH | CF$_3$ | CH$_2$CH$_2$-4-Pyridyl |
| 2185 | CH | C(OCH$_3$) | N | CH | CF$_3$ | CH$_2$CH$_2$-2-furanyl |
| 2186 | CH | C(OCH$_3$) | N | CH | CF$_3$ | CH$_2$CH$_2$-3-furanyl |
| 2187 | CH | C(OCH$_3$) | N | CH | CF$_3$ | CH$_2$CH$_2$-2-thienyl |
| 2188 | CH | C(OCH$_3$) | N | CH | CF$_3$ | CH$_2$CH$_2$-3-thienyl |
| 2189 | CH | CH | N | CH | CF$_3$ | C≡C-cycPr |
| 2190 | CH | CH | N | CH | CF$_3$ | C≡C-iPr |
| 2191 | CH | CH | N | CH | CF$_3$ | C≡C-nPr |
| 2192 | CH | CH | N | CH | CF$_3$ | C≡C-Et |
| 2193 | CH | CH | N | CH | CF$_3$ | C≡C-3-Pyridyl |
| 2194 | CH | CH | N | CH | CF$_3$ | C≡C-2-furanyl |
| 2195 | CH | CH | N | CH | CF$_3$ | C≡C-3-furanyl |
| 2196 | CH | CH | N | CH | CF$_3$ | C≡C-2-thienyl |
| 2197 | CH | CH | N | CH | CF$_3$ | C≡C-3-thienyl |
| 2198 | CCl | N | CH | CH | CF$_3$ | C≡C-cycPr |
| 2199 | CCl | N | CH | CH | CF$_3$ | C≡C-iPr |
| 2200 | CCl | N | CH | CH | CF$_3$ | C≡C-nPr |
| 2201 | CCl | N | CH | CH | CF$_3$ | C≡C-Bu |
| 2202 | CCl | N | CH | CH | CF$_3$ | C≡C-iBu |
| 2203 | CCl | N | CH | CH | CF$_3$ | C≡C-tBu |
| 2204 | CCl | N | CH | CH | CF$_3$ | C≡C-Et |
| 2205 | CCl | N | CH | CH | CF$_3$ | C≡C-Me |
| 2206 | CCl | N | CH | CH | CF$_3$ | C≡C-Ph |
| 2207 | CCl | N | CH | CH | CF$_3$ | C≡C-2-Pyridyl |
| 2208 | CCl | N | CH | CH | CF$_3$ | C≡C-3-Pyridyl |
| 2209 | CCl | N | CH | CH | CF$_3$ | C≡C-4-Pyridyl |
| 2210 | CCl | N | CH | CH | CF$_3$ | C≡C-2-furanyl |
| 2211 | CCl | N | CH | CH | CF$_3$ | C≡C-3-furanyl |
| 2212 | CCl | N | CH | CH | CF$_3$ | C≡C-2-thienyl |
| 2213 | CCl | N | CH | CH | CF$_3$ | C≡C-3-thienyl |
| 2214 | CCl | N | CH | CH | CF$_3$ | CH=CH-cycPr |
| 2215 | CCl | N | CH | CH | CF$_3$ | CH=CH-iPr |
| 2216 | CCl | N | CH | CH | CF$_3$ | CH=CH-nPr |
| 2217 | CCl | N | CH | CH | CF$_3$ | CH=CH-Bu |
| 2218 | CCl | N | CH | CH | CF$_3$ | CH=CH-iBu |
| 2219 | CCl | N | CH | CH | CF$_3$ | CH=CH-tBu |
| 2220 | CCl | N | CH | CH | CF$_3$ | CH=CH-Et |
| 2221 | CCl | N | CH | CH | CF$_3$ | CH=CH-Me |
| 2222 | CCl | N | CH | CH | CF$_3$ | CH=CH-Ph |
| 2223 | CCl | N | CH | CH | CF$_3$ | CH=CH-2-Pyridyl |
| 2224 | CCl | N | CH | CH | CF$_3$ | CH=CH-3-Pyridyl |
| 2225 | CCl | N | CH | CH | CF$_3$ | CH=CH-4-Pyridyl |
| 2226 | CCl | N | CH | CH | CF$_3$ | CH=CH-2-furanyl |
| 2227 | CCl | N | CH | CH | CF$_3$ | CH=CH-3-furanyl |
| 2228 | CCl | N | CH | CH | CF$_3$ | CH=CH-2-thienyl |
| 2229 | CCl | N | CH | CH | CF$_3$ | CH=CH-3-thienyl |
| 2230 | CCl | N | CH | CH | CF$_3$ | CH$_2$CH$_2$CH$_2$CH$_2$CH$_3$ |
| 2231 | CCl | N | CH | CH | CF$_3$ | CH$_2$CH$_2$CH(CH$_3$)$_2$ |
| 2232 | CCl | N | CH | CH | CF$_3$ | CH$_2$CH$_2$CH$_2$CH$_3$ |
| 2233 | CCl | N | CH | CH | CF$_3$ | CH$_2$CH$_2$CH$_3$ |
| 2234 | CCl | N | CH | CH | CF$_3$ | CH$_2$CH$_2$-cycPr |
| 2235 | CCl | N | CH | CH | CF$_3$ | CH$_2$CH$_2$-tBu |
| 2236 | CCl | N | CH | CH | CF$_3$ | CH$_2$CH$_2$-Ph |
| 2237 | CCl | N | CH | CH | CF$_3$ | CH$_2$CH$_2$-2-Pyridyl |
| 2238 | CCl | N | CH | CH | CF$_3$ | CH$_2$CH$_2$-3-Pyridyl |
| 2239 | CCl | N | CH | CH | CF$_3$ | CH$_2$CH$_2$-4-Pyridyl |
| 2240 | CCl | N | CH | CH | CF$_3$ | CH$_2$CH$_2$-2-furanyl |
| 2241 | CCl | N | CH | CH | CF$_3$ | CH$_2$CH$_2$-3-furanyl |
| 2242 | CCl | N | CH | CH | CF$_3$ | CH$_2$CH$_2$-2-thienyl |
| 2243 | CCl | N | CH | CH | CF$_3$ | CH$_2$CH$_2$-3-thienyl |
| 2244 | CH | N | CH | CH | CF$_3$ | C≡C-iPr |
| 2245 | CH | N | CH | CH | CF$_3$ | C≡C-nPr |
| 2246 | CH | N | CH | CH | CF$_3$ | C≡C-Et |
| 2247 | CH | N | CH | CH | CF$_3$ | C≡C-3-Pyridyl |
| 2248 | CH | N | CH | CH | CF$_3$ | C≡C-2-furanyl |
| 2249 | CH | N | CH | CH | CF$_3$ | C≡C-3-furanyl |
| 2250 | CH | N | CH | CH | CF$_3$ | C≡C-2-thienyl |
| 2251 | CH | N | CH | CH | CF$_3$ | C≡C-3-thienyl |
| 2252 | N | CCl | CH | CH | CF$_3$ | C≡C-cycPr |
| 2253 | N | CCl | CH | CH | CF$_3$ | C≡C-iPr |
| 2254 | N | CCl | CH | CH | CF$_3$ | C≡C-nPr |
| 2255 | N | CCl | CH | CH | CF$_3$ | C≡C-Bu |
| 2256 | N | CCl | CH | CH | CF$_3$ | C≡C-iBu |
| 2257 | N | CCl | CH | CH | CF$_3$ | C≡C-tBu |
| 2258 | N | CCl | CH | CH | CF$_3$ | C≡C-Et |
| 2259 | N | CCl | CH | CH | CF$_3$ | C≡C-Me |

TABLE 3-continued

| | | | | | |
|---|---|---|---|---|---|
| 2260 | N | CCl | CH CH CF$_3$ | C≡C-Ph |
| 2261 | N | CCl | CH CH CF$_3$ | C≡C-2-Pyridyl |
| 2262 | N | CCl | CH CH CF$_3$ | C≡C-3-Pyridyl |
| 2263 | N | CCl | CH CH CF$_3$ | C≡C-4-Pyridyl |
| 2264 | N | CCl | CH CH CF$_3$ | C≡C-2-furanyl |
| 2265 | N | CCl | CH CH CF$_3$ | C≡C-3-furanyl |
| 2266 | N | CCl | CH CH CF$_3$ | C≡C-2-thienyl |
| 2267 | N | CCl | CH CH CF$_3$ | C≡C-3-thienyl |
| 2268 | N | CCl | CH CH CF$_3$ | CH=CH-cycPr |
| 2269 | N | CCl | CH CH CF$_3$ | CH=CH-iPr |
| 2270 | N | CCl | CH CH CF$_3$ | CH=CH-nPr |
| 2271 | N | CCl | CH CH CF$_3$ | CH=CH-Bu |
| 2272 | N | CCl | CH CH CF$_3$ | CH=CH-iBu |
| 2273 | N | CCl | CH CH CF$_3$ | CH=CH-tBu |
| 2274 | N | CCl | CH CH CF$_3$ | CH=CH-Et |
| 2275 | N | CCl | CH CH CF$_3$ | CH=CH-Me |
| 2276 | N | CCl | CH CH CF$_3$ | CH=CH-Ph |
| 2277 | N | CCl | CH CH CF$_3$ | CH=CH-2-Pyridyl |
| 2278 | N | CCl | CH CH CF$_3$ | CH=CH-3-Pyridyl |
| 2279 | N | CCl | CH CH CF$_3$ | CH=CH-4-Pyridyl |
| 2280 | N | CCl | CH CH CF$_3$ | CH=CH-2-furanyl |
| 2281 | N | CCl | CH CH CF$_3$ | CH=CH-3-furanyl |
| 2282 | N | CCl | CH CH CF$_3$ | CH=CH-2-thienyl |
| 2283 | N | CCl | CH CH CF$_3$ | CH=CH-3-thienyl |
| 2284 | N | CCl | CH CH CF$_3$ | CH$_2$CH$_2$CH$_2$CH$_2$CH$_3$ |
| 2285 | N | CCl | CH CH CF$_3$ | CH$_2$CH$_2$CH(CH$_3$)$_2$ |
| 2286 | N | CCl | CH CH CF$_3$ | CH$_2$CH$_2$CH$_2$CH$_3$ |
| 2287 | N | CCl | CH CH CF$_3$ | CH$_2$CH$_2$CH$_3$ |
| 2288 | N | CCl | CH CH CF$_3$ | CH$_2$CH$_2$-cycPr |
| 2289 | N | CCl | CH CH CF$_3$ | CH$_2$CH$_2$-tBu |
| 2290 | N | CCl | CH CH CF$_3$ | CH$_2$CH$_2$-Ph |
| 2291 | N | CCl | CH CH CF$_3$ | CH$_2$CH$_2$-2-Pyridyl |
| 2292 | N | CCl | CH CH CF$_3$ | CH$_2$CH$_2$-3-Pyridyl |
| 2293 | N | CCl | CH CH CF$_3$ | CH$_2$CH$_2$-4-Pyridyl |
| 2294 | N | CCl | CH CH CF$_3$ | CH$_2$CH$_2$-2-furanyl |
| 2295 | N | CCl | CH CH CF$_3$ | CH$_2$CH$_2$-3-furanyl |
| 2296 | N | CCl | CH CH CF$_3$ | CH$_2$CH$_2$-2-thienyl |
| 2297 | N | CCl | CH CH CF$_3$ | CH$_2$CH$_2$-3-thienyl |
| 2298 | N | C(OCH$_3$) | CH CH CF$_3$ | C≡C-cycPr |
| 2299 | N | C(OCH$_3$) | CH CH CF$_3$ | C≡C-iPr |
| 2300 | N | C(OCH$_3$) | CH CH CF$_3$ | C≡C-nPr |
| 2301 | N | C(OCH$_3$) | CH CH CF$_3$ | C≡C-Bu |
| 2302 | N | C(OCH$_3$) | CH CH CF$_3$ | C≡C-iBu |
| 2303 | N | C(OCH$_3$) | CH CH CF$_3$ | C≡C-tBu |
| 2304 | N | C(OCH$_3$) | CH CH CF$_3$ | C≡C-Et |
| 2305 | N | C(OCH$_3$) | CH CH CF$_3$ | C≡C-Me |
| 2306 | N | C(OCH$_3$) | CH CH CF$_3$ | C≡C-Ph |
| 2307 | N | C(OCH$_3$) | CH CH CF$_3$ | C≡C-2-Pyridyl |
| 2308 | N | C(OCH$_3$) | CH CH CF$_3$ | C≡C-3-Pyridyl |
| 2309 | N | C(OCH$_3$) | CH CH CF$_3$ | C≡C-4-Pyridyl |
| 2310 | N | C(OCH$_3$) | CH CH CF$_3$ | C≡C-2-furanyl |
| 2311 | N | C(OCH$_3$) | CH CH CF$_3$ | C≡C-3-furanyl |
| 2312 | N | C(OCH$_3$) | CH CH CF$_3$ | C≡C-2-thienyl |
| 2313 | N | C(OCH$_3$) | CH CH CF$_3$ | C≡C-3-thienyl |
| 2314 | N | C(OCH$_3$) | CH CH CF$_3$ | CH=CH-cycPr |
| 2315 | N | C(OCH$_3$) | CH CH CF$_3$ | CH=CH-iPr |
| 2316 | N | C(OCH$_3$) | CH CH CF$_3$ | CH=CH-nPr |
| 2317 | N | C(OCH$_3$) | CH CH CF$_3$ | CH=CH-Bu |
| 2318 | N | C(OCH$_3$) | CH CH CF$_3$ | CH=CH-iBu |
| 2319 | N | C(OCH$_3$) | CH CH CF$_3$ | CH=CH-tBu |
| 2320 | N | C(OCH$_3$) | CH CH CF$_3$ | CH=CH-Et |
| 2321 | N | C(OCH$_3$) | CH CH CF$_3$ | CH=CH-Me |
| 2322 | N | C(OCH$_3$) | CH CH CF$_3$ | CH=CH-Ph |
| 2323 | N | C(OCH$_3$) | CH CH CF$_3$ | CH=CH-2-Pyridyl |
| 2324 | N | C(OCH$_3$) | CH CH CF$_3$ | CH=CH-3-Pyridyl |
| 2325 | N | C(OCH$_3$) | CH CH CF$_3$ | CH=CH-4-Pyridyl |
| 2326 | N | C(OCH$_3$) | CH CH CF$_3$ | CH=CH-2-furanyl |
| 2327 | N | C(OCH$_3$) | CH CH CF$_3$ | CH=CH-3-furanyl |
| 2328 | N | C(OCH$_3$) | CH CH CF$_3$ | CH=CH-2-thienyl |
| 2329 | N | C(OCH$_3$) | CH CH CF$_3$ | CH=CH-3-thienyl |
| 2330 | N | C(OCH$_3$) | CH CH CF$_3$ | CH$_2$CH$_2$CH$_2$CH$_2$CH$_3$ |
| 2331 | N | C(OCH$_3$) | CH CH CF$_3$ | CH$_2$CH$_2$CH(CH$_3$)$_2$ |
| 2332 | N | C(OCH$_3$) | CH CH CF$_3$ | CH$_2$CH$_2$CH$_2$CH$_3$ |
| 2333 | N | C(OCH$_3$) | CH CH CF$_3$ | CH$_2$CH$_2$CH$_3$ |
| 2334 | N | C(OCH$_3$) | CH CH CF$_3$ | CH$_2$CH$_2$-cycPr |
| 2335 | N | C(OCH$_3$) | CH CH CF$_3$ | CH$_2$CH$_2$-tBu |
| 2336 | N | C(OCH$_3$) | CH CH CF$_3$ | CH$_2$CH$_2$-Ph |
| 2337 | N | C(OCH$_3$) | CH CH CF$_3$ | CH$_2$CH$_2$-2-Pyridyl |
| 2338 | N | C(OCH$_3$) | CH CH CF$_3$ | CH$_2$CH$_2$-3-Pyridyl |
| 2339 | N | C(OCH$_3$) | CH CH CF$_3$ | CH$_2$CH$_2$-4-Pyridyl |
| 2340 | N | C(OCH$_3$) | CH CH CF$_3$ | CH$_2$CH$_2$-2-furanyl |
| 2341 | N | C(OCH$_3$) | CH CH CF$_3$ | CH$_2$CH$_2$-3-furanyl |
| 2342 | N | C(OCH$_3$) | CH CH CF$_3$ | CH$_2$CH$_2$-2-thienyl |
| 2343 | N | C(OCH$_3$) | CH CH CF$_3$ | CH$_2$CH$_2$-3-thienyl |
| 2344 | N | CH | CH CH CF$_3$ | C≡C-cycPr |
| 2345 | N | CH | CH CH CF$_3$ | C≡C-iPr |
| 2346 | N | CH | CH CH CF$_3$ | C≡C-nPr |
| 2347 | N | CH | CH CH CF$_3$ | C≡C-Et |
| 2348 | N | CH | CH CH CF$_3$ | C≡C-3-Pyridyl |
| 2349 | N | CH | CH CH CF$_3$ | C≡C-2-furanyl |
| 2350 | N | CH | CH CH CF$_3$ | C≡C-3-furanyl |
| 2351 | N | CH | CH CH CF$_3$ | C≡C-2-thienyl |
| 2352 | N | CH | CH CH CF$_3$ | C≡C-3-thienyl |

*Unless otherwise noted, stereochemistry is (+/−) and in R$^2$, all double bonds are trans.

Utility

The compounds of this invention possess reverse transcriptase inhibitory activity, in particular, HIV inhibitory efficacy. The compounds of formula (I) possess HIV reverse transcriptase inhibitory activity and are therefore useful as antiviral agents for the treatment of HIV infection and associated diseases. The compounds of formula (I) possess HIV reverse transcriptase inhibitory activity and are effective as inhibitors of HIV growth. The ability of the compounds of the present invention to inhibit viral growth or infectivity is demonstrated in standard assay of viral growth or infectivity, for example, using the assay described below.

The compounds of formula (I) of the present invention are also useful for the inhibition of HIV in an ex vivo sample containing HIV or expected to be exposed to HIV. Thus, the compounds of the present invention may be used to inhibit HIV present in a body fluid sample (for example, a serum or semen sample) which contains or is suspected to contain or be exposed to HIV.

The compounds provided by this invention are also useful as standard or reference compounds for use in tests or assays for determining the ability of an agent to inhibit viral clone replication and/or HIV reverse transcriptase, for example in a pharmaceutical research program. Thus, the compounds of the present invention may be used as a control or reference compound in such assays and as a quality control standard. The compounds of the present invention may be provided in a commercial kit or container for use as such standard or reference compound.

Since the compounds of the present invention exhibit specificity for HIV reverse transcriptase, the compounds of the present invention may also be useful as diagnostic reagents in diagnostic assays for the detection of HIV reverse transcriptase. Thus, inhibition of the reverse transcriptase activity in an assay (such as the assays described herein) by a compound of the present invention would be indicative of the presence of HIV reverse transcriptase and HIV virus.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar and "nm" denotes nanometer. "Sigma" stands for the Sigma-Aldrich Corp. of St. Louis, Mo.

HIV RNA Assay

DNA Plasmids and in vitro RNA Transcripts

Plasmid pDAB 72 containing both gag and pol sequences of BH10 (bp 113–1816) cloned into PTZ 19R was prepared according to Erickson-Viitanen et al. *AIDS Research and Human Retroviruses* 1989, 5, 577. The plasmid was linearized with Bam HI prior to the generation of in vitro RNA transcripts using the Riboprobe Gemini system II kit (Promega) with T7 RNA polymerase. Synthesized RNA was purified by treatment with RNase free DNAse (Promega), phenol-chloroform extraction, and ethanol precipitation. RNA transcripts were dissolved in water, and stored at $-70°$ C. The concentration of RNA was determined from the $A_{260}$.

Probes

Biotinylated capture probes were purified by HPLC after synthesis on an Applied Biosystems (Foster City, Calif.) DNA synthesizer by addition of biotin to the 5' terminal end of the oligonucleotide, using the biotin-phosphoramidite reagent of Cocuzza, *Tet. Lett.* 1989, 30, 6287. The gag biotinylated capture probe (5-biotin-CTAGCTCCCTGCTTGCCCATACTA 3') was complementary to nucleotides 889–912 of HXB2 and the pol biotinylated capture probe (5'-biotin-CCCTATCATTTTTGGTTTCCAT 3') was complementary to nucleotides 2374–2395 of HXB2. Alkaline phosphatase conjugated oligonucleotides used as reporter probes were prepared by Syngene (San Diego, Calif.). The pol reporter probe (5' CTGTCTTACTTTGATAAAACCTC 3') was complementary to nucleotides 2403–2425 of HXB2. The gag reporter probe (5' CCCAGTATTTGTCTACAGCCT-TCT 3') was complementary to nucleotides 950–973 of HXB2. All nucleotide positions are those of the GenBank Genetic Sequence Data Bank as accessed through the Genetics Computer Group Sequence Analysis Software Package Devereau *Nucleic Acids Research* 1984, 12, 387). The reporter probes were prepared as 0.5 $\mu$M stocks in 2×SSC (0.3 M NaCl, 0.03 M sodium citrate), 0.05 M Tris pH 8.8, 1 mg/mL BSA. The biotinylated capture probes were prepared as 100 $\mu$M stocks in water.

Streptavidin Coated Plates

Streptavidin coated plates were obtained from Du Pont Biotechnology Systems (Boston, Ma.).

Cells and Virus Stocks

MT-2 and MT-4 cells were maintained in RPMI 1640 supplemented with 5% fetal calf serum (FCS) for MT-2 cells or 10% FCS for MT-4 cells, 2 mM L-glutamine and 50 $\mu$g/mL gentamycin, all from Gibco. HIV-1 RF was propagated in MT-4 cells in the same medium. Virus stocks were prepared approximately 10 days after acute infection of MT-4 cells and stored as aliquots at $-70°$ C. Infectious titers of HIV-1(RF) stocks were $1-3\times10^7$ PFU (plaque forming units)/mL as measured by plaque assay on MT-2 cells (see below). Each aliquot of virus stock used for infection was thawed only once.

For evaluation of antiviral efficacy, cells to be infected were subcultured one day prior to infection. On the day of infection, cells were resuspended at $5\times10^5$ cells/mL in RPMI 1640, 5% FCS for bulk infections or at $2\times10^6$/mL in Dulbecco's modified Eagles medium with 5% FCS for infection in microtiter plates. Virus was added and culture continued for 3 days at 37° C.

HIV RNA Assay

Cell lysates or purified RNA in 3 M or 5 M GED were mixed with 5 M GED and capture probe to a final guanidinium isothiocyanate concentration of 3 M and a final biotin oligonucleotide concentration of 30 nM. Hybridization was carried out in sealed U bottom 96 well tissue culture plates (Nunc or Costar) for 16–20 hours at 37° C. RNA hybridization reactions were diluted three-fold with deionized water to a final guanidinium isothiocyanate concentration of 1 M and aliquots (150 $\mu$L) were transferred to streptavidin coated microtiter plates wells. Binding of capture probe and capture probe-RNA hybrid to the immobilized streptavidin was allowed to proceed for 2 hours at room temperature, after which the plates were washed 6 times with DuPont ELISA plate wash buffer (phosphate buffered saline(PBS), 0.05% Tween 20.) A second hybridization of reporter probe to the immobilized complex of capture probe and hybridized target RNA was carried out in the washed streptavidin coated well by addition of 120 $\mu$l of a hybridization cocktail containing 4×SSC, 0.66% Triton X 100, 6.66% deionized formamide, 1 mg/mL BSA and 5 nM reporter probe. After hybridization for one hour at 37° C., the plate was again washed 6 times. Immobilized alkaline phosphatase activity was detected by addition of 100 $\mu$L of 0.2 mM 4-methylumbelliferyl phosphate (MUBP, JBL Scientific) in buffer $\delta$ (2.5 M diethanolamine pH 8.9 (JBL Scientific), 10 mM $MgCl_2$, 5 mM zinc acetate dihydrate and 5 mM N-hydroxyethyl-ethylene-diamine-triacetic acid). The plates were incubated at 37° C. Fluorescence at 450 nM was measured using a microplate fluorometer (Dynateck) exciting at 365 nM.

Microplate Based Compound Evaluation in HIV-1 Infected MT-2 Cells

Compounds to be evaluated were dissolved in DMSO and diluted in culture medium to twice the highest concentration to be tested and a maximum DMSO concentration of 2%. Further three-fold serial dilutions of the compound in culture medium were performed directly in U bottom microtiter plates (Nunc). After compound dilution, MT-2 cells (50 $\mu$L) were added to a final concentration of $5\times10^5$ per mL ($1\times10^5$ per well). Cells were incubated with compounds for 30 minutes at 37° C. in a $CO_2$ incubator. For evaluation of antiviral potency, an appropriate dilution of HIV-1 (RF) virus stock (50 $\mu$L) was added to culture wells containing cells and dilutions of the test compounds. The final volume in each well was 200 $\mu$L. Eight wells per plate were left uninfected with 50 $\mu$L of medium added in place of virus, while eight wells were infected in the absence of any antiviral compound. For evaluation of compound toxicity, parallel plates were cultured without virus infection.

After 3 days of culture at 37° C. in a humidified chamber inside a $CO_2$ incubator, all but 25 $\mu$L of medium/well was removed from the HIV infected plates. Thirty seven $\mu$L of 5 M GED containing biotinylated capture probe was added to the settled cells and remaining medium in each well to a final concentration of 3 M GED and 30 nM capture probe. Hybridization of the capture probe to HIV RNA in the cell lysate was carried out in the same microplate well used for virus culture by sealing the plate with a plate sealer (Costar), and incubating for 16–20 hrs in a 37° C. incubator. Distilled water was then added to each well to dilute the hybridization reaction three-fold and 150 $\mu$L of this diluted mixture was transferred to a streptavidin coated microtiter plate. HIV RNA was quantitated as described above. A standard curve, prepared by adding known amounts of PDAB 72 in vitro RNA transcript to wells containing lysed uninfected cells, was run on each microtiter plate in order to determine the amount of viral RNA made during the infection.

In order to standardize the virus inoculum used in the evaluation of compounds for antiviral activity, dilutions of virus were selected which resulted in an $IC_{90}$ value (concentration of compound required to reduce the HIV RNA level by 90%) for dideoxycytidine (ddC) of 0.2 $\mu$g/mL. $IC_{90}$ values of other antiviral compounds, both more and less potent than ddC, were reproducible using several stocks of HIV-1 (RF) when this procedure was followed. This concentration of virus corresponded to ~3×10⁵ PFU (measured by plaque assay on MT-2 cells) per assay well and typically produced approximately 75% of the maximum viral RNA level achievable at any virus inoculum. For the HIV RNA assay, $IC_{90}$ values were determined from the percent reduction of net signal (signal from infected cell samples minus signal from uninfected cell samples) in the RNA assay relative to the net signal from infected, untreated cells on the same culture plate (average of eight wells). Valid performance of individual infection and RNA assay tests was judged according to three criteria. It was required that the virus infection should result in an RNA assay signal equal to or greater than the signal generated from 2 ng of pDAB 72 in vitro RNA transcript. The $IC_{90}$ for ddC, determined in each assay run, should be between 0.1 and 0.3 μg/mL. Finally, the plateau level of viral RNA produced by an effective reverse transcriptase inhibitor should be less than 10% of the level achieved in an uninhibited infection. A compound was considered active if its $IC_{90}$ was found to be less than 20 μM.

For antiviral potency tests, all manipulations in microtiter plates, following the initial addition of 2×concentrated compound solution to a single row of wells, were performed using a Perkin Elmer/Cetus ProPette.

HIV-1 RT Assay Materials and Methods

This assay measures HIV-1 RT RNA dependent DNA polymerase activity by the incorporation of 3H dTMP onto the template primer Poly (rA) oligo (dT)12-18. The template primer containing the incorporated radioactivity was separated from unincorporated label by one of two methods:

Method 1. The template primer was precipitated with TCA, collected on glass fiber filters and counted for radioactivity with a scintillation counter.

Method 2. The currently used method is more rapid and convenient. The template primer is captured on an diethyl amino ethyl (DEAE) ion exchange membrane which is then counted for radioactivity after washing off the free nucleotide.

Materials and Reagents

The template primer Poly (rA) oligo (dT)12-18 and dTTP were purchased from Pharmacia Biotech. The template primer and nucleotide were dissolved in diethyl pyrocarbonate water to a concentration of 1 mg/mL and 5.8 mM respectively. The substrates were aliquoted (template primer at 20 μl/aliquot, dTTP at 9 μl/aliquot) and frozen at −20 C.

The 3H dTTP (2.5 mCi/mL in 10 mM Tricine at pH 7.6; specific activity of 90–120 Ci/mmol) and the recombinant HIV-1 Reverse Transcriptase (HxB2 background; 100 U/10 μl in 100 mM potassium phosphate at pH 7.1, 1 mM dithiothreitol and 50% glycerol) were purchased from DuPont NEN. 1 Unit of enzyme is defined by DuPont NEN as the amount required to incorporate 1 nmol of labelled dTTP into acid-insoluble material in 10 minutes at 37 C. The 3H dTTP was aliquoted at 23.2 μl/microfuge tube (58 μCi) and frozen at −20 C. The HIV-1 Reverse Transcriptase (RT) was diluted 10 fold with RT buffer (80 mM KCl, 50 mM Tris HCl, 12 mM MgCl2, 1 mM DTT, 50 μM EGTA, 5 mg/mL BSA, 0.01% Triton-X 100, pH 8.2) and aliquoted at 10 μl/microfuge tube (10 Units/10 μl). One aliquot (enough for 8 assays) was diluted further to 10 Units/100 μl and aliquoted into 8 tubes (1.25 Units/12.5 μl). All aliquots were frozen at −70 C.

The Millipore Multiscreen DE 96 well filter plates, multiscreen plate adaptors, and microplate press-on adhesive sealing film were purchased from Millipore. The filter plate containing 0.65 pm pore size diethyl amino ethyl cellulose (DEAE) paper disks was pretreated with 0.3 M ammonium formate and 10 mM sodium pyrophosphate (2 times 200 μl /well) at pH 8.0 prior to use. A Skatron 96 well cell harvester and glass fiber filter mats were purchased from Skatron Instruments. Microscint 20 scintillation cocktail was purchased from Packard. Beckman Ready Flow III scintillation cocktail was purchased from Beckman.

HIV-1 RT Assay

The enzyme and substrate mixture were freshly prepared from the above stock solutions. 1.25 Units of enzyme was diluted with RT buffer (containing 5 mg/mL BSA) to a concentration of 0.05 Units/10 μl or 0.7 nM. Final enzyme and BSA concentrations in the assay were 0.01 Units or 0.14 nM and 1 mg/mL respectively. The inhibitor and substrate mixture were diluted with RT buffer containing no BSA. All inhibitors were dissolved in dimethyl sulfoxide (DMSO) at a stock concentration of 3 mM and stored at −20 C. after use. A Biomek robot was used to dilute the inhibitors in a 96 well plate. Inhibitors were initially diluted 96 fold from stock and then serially diluted two times (10 fold/dilution) from 31.25 μM to 3125 nM and 312.5 nM. Depending on the potency of the inhibitor, one of the three dilutions was further diluted. Typically the highest concentration (31.25 aM) was serially diluted three times at 5 fold/dilution to 6.25, 1.25, and 0.25 μM. Final inhibitor concentrations in the assay were 12.5, 2.5, 0.5, and 0.1 μM. For potent inhibitors of HIV-1 RT, the final inhibitor concentrations used were 0.1 or 0.01 that stated above. The substrate mixture contained 6.25 μg/mL of Poly (rA) oligo (dT)12–18 and 12.5 μM of dTTP (58 μCi 3H dTTP). The final substrate concentrations were 2.5 μg/mL and 5 μM respectively.

Using the Beckman Instruments Biomek robot, 10 μl of HIV-1 RT was combined with 20 μl of inhibitor in a 96 well U bottom plate. The enzyme and inhibitor were preincubated at ambient temperature for 6 minutes. 20 μl of the substrate mixture was added to each well to initiate the reaction (total volume was 50 μl). The reactions were incubated at 37 C. and terminated after 45 minutes.

For method 1, 200 μl of an ice-cold solution of 13% trichloroacetic acid (TCA) and 10 mM sodium pyrophosphate was added to each of the 96 wells. The 96 well plate was then placed in an ice-water bath for 30 minutes. Using A Skatron 96 well cell harvester, the acid precipitable material was collected on a glass fiber filter mat that had been presoaked in 13% TCA and 10 mM sodium pyrophosphate. The filter disks were washed 3 times (2.0 mL/wash) with 1 N HCl and 10 mM sodium pyrophosphate. The filter disks were punched out into scintillation vials, 2.0 mL of Beckman Ready Flow III scintillant was added, and the vials were counted for radioactivity for 1 minute.

For method 2, the assay was terminated with the addition of 175 μl/well of 50 mM EDTA at pH 8.0. Then 180 μl of the mixture was transferred to a pretreated Millipore DE 96 well filter plate. Vacuum was applied to the filter plate to aspirate away the liquid and immobilize the template primer on the DEAE filter disks. Each well was washed 3 times with 200 μl of 0.3 M ammonium formate and 10 mM sodium pyrophosphate at pH 8.0. 50 μl of microscint 20 scintillation cocktail was added to each well and the plate was counted for radioactivity on a Packard Topcount at 1 minute/well.

The $IC_{50}$ values are calculated with the equation:

$$IC_{50}=[Inh]/(1/\text{fractional activity}-1)$$

where the fractional activity=RT activity (dpms) in the presence of inhibitor/RT activity (dpms) in the absence of inhibitor. For a given inhibitor, the $IC_{50}$ values were calculated for the inhibitor concentrations that range between 0.1–0.8 fractional activity. The $IC_{50}$ values in this range (generally 2 values) were averaged. A compound was considered active if its $IC_{50}$ was found to be less than 12 µM.

Protein Binding and Mutant Resistance

In order to characterize NNRTI analogs for their clinical efficacy potential the effect of plasma proteins on antiviral potency and measurements of antiviral potency against wild type and mutant variants of HIV which carry amino acid changes in the known binding site for NNRTIs were examined. The rationale for this testing strategy is two fold:

1. Many drugs are extensively bound to plasma proteins. Although the binding affinity for most drugs for the major components of human plasma, namely, human serum albumin (HSA) or alpha-1-acid glycoprotein (AAG), is low, these major components are present in high concentration in the blood. Only free or unbound drug is available to cross the infected cell membrane for interaction with the target site (i.e., HIV-1 reverse transcriptase, HIV-1 RT). Therefore, the effect of added HSA+AAG on the antiviral potency in tissue culture more closely reflects the potency of a given compound in the clinical setting. The concentration of compound required for 90% inhibition of virus replication as measured in a sensitive viral RNA-based detection method is designated the $IC_{90}$. The fold increase in apparent $IC_{90}$ for test compounds in the presence or added levels of HSA and AAG that reflect in vivo concentrations (45 mg/mL HSA, 1 mg/mL AAG) was then calculated. The lower the fold increase, the more compound will be available to interact with the target site.

2. The combination of the high rate of virus replication in the infected individual and the poor fidelity of the viral RT results in the production of a quasi-species or mixtures of HIV species in the infected individual. These species will include a majority wild type species, but also mutant variants of HIV and the proportion of a given mutant will reflect its relative fitness and replication rate. Because mutant variants including mutants with changes in the amino acid sequence of the viral RT likely pre-exist in the infected individual's quasi-species, the overall potency observed in the clinical setting will reflect the ability of a drug to inhibit not only wild type HIV-1, but mutant variants as well. We thus have constructed, in a known genetic background, mutant variants of HIV-1 which carry amino acid substitutions at positions thought to be involved in NNRTI binding, and measured the ability of test compounds to inhibit replication of these mutant viruses. The concentration of compound required for 90% inhibition of virus replication as measured in a sensitive viral RNA-based detection method is designated the $IC_{90}$. It is desirable to have a compound which has high activity against a variety of mutants.

Dosage and Formulation

The antiviral compounds of this invention can be administered as treatment for viral infections by any means that produces contact of the active agent with the agent's site of action, i.e., the viral reverse transcriptase, in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can-be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences,* supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Combination of Components (a) and (b)

Each therapeutic agent component of this invention can independently be in any dosage form, such as those described above, and can also be administered in various ways, as described above. In the following description component (b) is to be understood to represent one or more agents as described previously. Thus, if components (a) and (b) are to be treated the same or independently, each agent of component (b) may also be treated the same or independently.

Components (a) and (b) of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the revserse order. If component (b) contains more that one agent, e.g., one RT inhibitor and one protease inhibitor, these agents may be administered together or in any order. When not administered at the same time, preferably the administration of component (a) and (b) occurs less than about one hour apart. Preferably, the route of administration of component (a) and (b) is oral. The terms oral agent, oral inhibitor, oral compound, or the like, as used herein, denote compounds which may be orally administered. Although it is preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and eight of the recipient, the nature and extent of the symptoms, the kind of concurrent treatment, the frequency of treatment, and the effect desired, as described above.

The proper dosage of components (a) and (b) of the present invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70–80% relative to the usual dosage of the component when it is administered alone as a single agent for the treatment of HIV infection, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of HIV infection, which comprise a therapeutically effective amount of a pharmaceutical composition comprising a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers of materials may comprise separate containers, or one or more multi-part containers, as desired. Component (a) and component (b), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter Patent of United States is:

1. A method of treating HIV infection which comprises administering, in combination, to a host in need thereof a therapeutically effective amount of:

(a) a compound of formula (I):

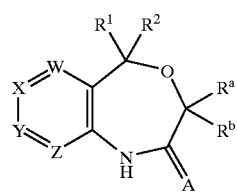

I or a stereoisomer or pharmaceutically acceptable salt form thereof, wherein:

A is O or S;
W is N or $CR^3$;
X is N or $CR^4$;
Y is N or $CR^5$;
Z is N or $CR^6$;
provided that if two of W, X, Y, and Z are N, then the remaining are other than N;
$R^a$ is selected from H, $CF_3CF_2H$, $C_{1-4}$ alkyl, $C_{3-5}$ cycloalkyl, $C_{2-4}$ alkenyl, $C_{2-4}$ alkynyl, and phenyl substituted with 0–2 $R^{10}$;
$R^b$ is selected from H, $CF_3$, $CF_2H$, $C_{1-4}$ alkyl, $C_{3-5}$ cycloalky, $C_{2-4}$ alkenyl, $C_{2-4}$ alkynyl, and phenyl substituted with 0–2 $R^{10}$;
alternatively, $R^a$ and $R^b$ together form —$(CH_2)_n$—;
$R^1$ is selected from $CF_3$, $CF_2H$, $C_{1-4}$ alkyl, $C_{3-5}$ cycloalkyl, $C_{2-4}$ alkenyl, and $C_{2-4}$ alkynyl;
$R^2$ is selected from —C≡C—$R^8$, —CH=$CR^7R^8$, —$(CH_2)_p CHR^7R^8$, —$CHR^7 C$≡$C$—$R^8$, —$CHR^7 CH$=$CHR^8$, and CH=$CHCHR^7R^8$;
provided that when either of $R^a$ or $R^b$ is phenyl, then $R^1$ is other than $C_{1-4}$ alkyl and $C_{3-5}$ cycloalkyl and $R^2$ is other than —$(CH_2)_p CHR^7R^8$;
$R^3$ is selected from H, F, Cl, Br, I, $C_{1-3}$ alkoxy, and $C_{1-3}$ alkyl;
$R^4$ is selected from H, F, Cl, Br, I, $C_{1-3}$ alkyl substituted with 0–3 $R^{11}$, $C_{2-3}$ alkenyl, $C_{2-3}$ alkynyl, $C_{1-3}$ alkoxy, $OCF_3$, —CN, $NO_2$, CHO, $C(O)CH_3$, $C(O)CF_3$, $C(O)NH_2$, $C(O)NHCH_3$, $NR^7R^{7a}$, $NR^7C(O)OR^{7b}$, $C(O)$ $OR^7$, $S(O)_p R^7$, $SO_2NHR^7$, $NR^7SO_2R^{7b}$, phenyl substituted with 0–2 $R^{10}$, and 5–6 membered aromatic heterocycle system containing from 1–4 heteroatoms selected from the group consisting of N, O, and S and substituted with 0–2 $R^{10}$;
alternatively, $R^3$ and $R^4$ together form —$OCH_2O$—;
$R^5$ is selected from H, F, Cl, Br, and I;
alternatively, $R^4$ and $R^5$ together form a —$OCH_2O$— or a fused benzo ring;
$R^6$ is selected from H, OH, $C_{1-3}$ alkoxy, —CN, F, Cl, Br, I, $NO_2$, $CF_3$, CHO, $C_{1-3}$ alkyl, and $C(O)NH_2$;
$R^7$, at each occurrence, is selected from H and $C_{1-3}$ alkyl;
$R^{7a}$, at each occurrence, is selected from H and $C_{1-3}$ alkyl;
$R^{7b}$, at each occurrence, is $C_{1-3}$ alkyl;
$R^8$, at each occurrence, is selected from H, $C_{1-6}$ alkyl substituted with 0–3 $R^{11}$, CH(—$OCH_2CH_2O$—), $C_{2-6}$ alkenyl, $C_{3-7}$ cycloalkyl substituted with 0–2 $R^9$, phenyl substituted with 0–2 $R^{10}$, and 5–6 membered aromatic heterocycle system containing from 1–4 heteroatoms selected from the group consisting of N, O, and S and substituted with 0–2 $R^{10}$;
$R^9$, at each occurrence, is selected from D ($^2$H), OH, $C_{1-3}$ alkoxy, $C_{1-3}$ alkyl, and F;
$R^{10}$, at each occurrence, is selected from OH, $C_{1-3}$ alkyl, $C_{1-3}$ alkoxy, F, Cl, Br, I, CN, $NR^7R^{7a}$, and $C(O)CH_3$;
$R^{11}$, and each occurrence, is selected from $OR^7$, CN, F, Cl, Br, I, $NO_2$, $NR^7R^{7a}$, CHO, $C(O)CH_3$, $C(O)NH_2$;
n, at each occurrence, is selected from 1, 2, 3, 4, and 5; and,
p, at each occurrence, is selected from 0, 1, and 2; and (b) at least one compound selected from the group consisting of HIV reverse transcriptase inhibitors and HIV protease inhibitors.

2. A method according to claim 1, wherein, the reverse transcriptase inhibitor is a nucleoside reverse transcriptase inhibitor.

3. A method according to claim 1, wherein, the reverse transcriptase inhibitor is selected from AZT (azidothymidine), 3TC (β-L-3'-thia-2',3'-dideoxycytidine), efavirenz, rescriptor, ddI (dideoxyinosine), ddC (dideoxycytidine), and d4T (2',3,'-didehydro-3'-deoxythimidine), and the protease inhibitor is selected from saquinavir, ritonavir, indinavir, VX-478 (amprenavir, 4-amino-N-[2(R)-hydroxy-4-phenyl-3(S)-[tetrahydrofuran-3(S)-yloxycarbonylamino]butyl]-N-isobutylbenzenesulfonamide), nelfinavir, KNI-272 (3-(2-Hydroxy-3-{2-[2-(isoquinolin-5-yloxy)-acetylamino]3-methylsulfanyl-propionylamino}-4-phenyl-butyryl)-thiazolidine--4-carboxylic acid tert-butylamide), CGP-61755 (lasinavir), and U-103017 (4-cyano-N-[3-[cyclopropyl(5,6,7,8,9,10-hexahydro-4-hydroxy-2-oxo-2H-cycloocta[b]pyran-3-yl)methyl]phenyl]-benzenesulfonamide).

4. A method according to claim 3, wherein the reverse transcriptase inhibitor is selected from AZT (azidothymidine), efavirenz; rescriptor, and 3TC (β-L-3'-thia-2',3'dideoxycytidine) and the protease inhibitor is selected from saquinavir, ritonavir, indinavir, and nelfinavir.

5. A method according to claim 4, wherein, the reverse transcriptase inhibitor is AZT (azidothymidine).

6. A method according to claim 4, wherein, the protease inhibitor is indinavir.

7. The method of claim 1, wherein $R^a$ is H;

$R^b$ is selected from H, $CF_3$, $CF_2H$, cyclopropyl, $CH=CH_2$, and $C_{1-4}$ alkyl;

$R^1$ is selected from $CF_3$, $CF_2H$, $C_{1-3}$ alkyl, and $C_{3-5}$ cycloalkyl; and, $R^8$ is selected from H, $C_{1-6}$ alkyl substituted with 0–3 $R^{11}$, $CH(-OCH_2CH_2O-)$, $C_{2-6}$ alkenyl, $C_{3-5}$ cycloalkyl substituted with 0–1 $R^9$, phenyl substituted with 0–1 $R^{10}$, and 5–6 membered aromatic heterocycle system containing from 1–4 heteroatoms selected from the group consisting of N, O, and S substituted with 0–1 $R^{10}$.

8. The method of claim 7, wherein

A is O;

$R^1$ is selected from $CF_3$, $CF_2H$, $C_2H_5$, isopropyl, and cyclopropyl;

$R^3$ is selected from H, F, Cl, Br, I, $OCH_3$, and $CH_3$;

$R^4$ is selected from H, F, Cl, Br, I, $C_{1-3}$ alkyl substituted with 0–3 $R^{11}$, $C_{2-3}$ alkenyl, $C_{2-3}$ alkynyl, $C_{1-3}$ alkoxy, $OCF_3$, —CN, $NO_2$, CHO, $C(O)CH_3$, $C(O)CF_3$, $C(O)NH_2$, $C(O)NHCH_3$, $NR^7R^{7a}$, $NR^7C(O)OR^{7b}$; $C(O)OR^7$, $S(O)_pR^7$, $SO_2NHR^7$, $NR^7SO_2R^{7b}$, phenyl, and 5–6 membered aromatic heterocycle system containg from 1–4 heteroatoms selected from the group consisting of N, O, and S;

alternatively, $R^3$ and $R^4$ together form $-OCH_2O-$;

$R^5$ is selected from H and F;

$R^6$ is selected from H, OH, $OCH_3$, —CN, F, $CF_3$, $CH_3$, and $C(O)NH_2$;

$R^7$ is selected from H and $CH_3$;

$R^{7a}$ is selected from H and $CH_3$;

$R^{7b}$ is $CH_3$;

$R^8$ is selected from H, $C_{1-4}$ alkyl substituted with 0–3 $R^{11}$, $CH(-OCH_2CH_2O-)$, $C_{2-4}$ alkenyl, $C_{3-5}$ cycloalkyl substituted with 0–1 $R^9$, phenyl substituted with 0–1 $R^{10}$, and 5–6 membered aromatic heterocycle system containing from 1–4 heteroatoms selected from the group consisting of N, O, and S substituted with 0–1 $R^{10}$;

$R^9$ is selected from D, OH, $OCH_3$, $CH_3$, and F;

$R^{10}$ is selected from OH, $CH_3$, $OCH_3$, F, Cl, Br, I, CN, $NR^7R^{7a}$, and $C(O)CH_3$; and, p is selected from 1 and 2.

9. The method of claim 8, wherein $R^b$ is selected from H, $CF_3$, $CF_2H$, cyclopropyl, $CH=CH_2$, $CH_3$, and $CH_2CH_3$;

$R^1$ is selected from $CF_3$, $CF_2H$, and cyclopropyl;

$R^2$ is selected from $-C\equiv C-R^8$ and trans-$CH=CR^7R^8$;

$R^3$ is selected from H, F, Cl, Br, and I;

$R^4$ is selected from H, F, Cl, Br, I, $C_{1-3}$ alkyl substituted with 0–3 $R^{11}$, $CH=CH_2$, $C\equiv CH$, $OCH_3$, $OCF_3$, —CN, $NO_2$, CHO, $C(O)CH_3$, $C(O)CF_3$, $C(O)NH_2$, $C(O)NHCH_3$, $NR^7R^{7a}$, $C(O)OR^7$, $NR^7SO_2R^{7b}$, and 5–6 membered aromatic heterocycle system containing from 1–4 heteroatoms selected from the group consisting of N, O, and S;

alternatively, $R^3$ and $R^4$ together form $-OCH_2O-$; and, $R^{11}$ is selected from OH, $OCH_3$, CN, F, Cl, $NR^7R^{7a}$, $C(O)CH_3$, and $C(O)NH_2$.

10. The method of claim 9, wherein the compound of Formula (I) is selected from 5-(1-Butynyl)-7-chloro-1,5-dihydro-5-(trifluoromethyl)-4,1-benzoxazepin-2(3H)-one;

rel-(3S,5S)-5-(1-Butynyl)-7-chloro-1,5-dihydro-3-phenyl-5-(trifluoromethyl)-4,1-benzoxazepin-2(3H)-one;

7-Chloro-1,5-dihydro-5-(isopropylethynyl)-5-(trifluoromethyl)-4,1-benzoxazepin-2(3H)-one;

(+)-(5S)-7-Chloro-1,5-dihydro-5-(isopropylethynyl)-5-(trifluoromethyl)-4,1-benzoxazepin-2(3H)-one;

trans-7-Chloro-5-(2-cyclopropylethenyl)-1,5-dihydro-5-(trifluoromethyl)-4,1-benzoxazepin-2(3H)-one;

rel-(3S,5S)-trans-7-Chloro-5-(2-cyclopropylethenyl)-1,5-dihydro-3-methyl-5-(trifluoromethyl)-4,1-benzoxazepin-2(3H)-one;

1,5-Dihydro-7-fluoro-5-isopropylethynyl-5-(trifluoromethyl)-4,1-benzoxazepin-2(3H)-one;

1,5-Dihydro-7-fluoro-5-(3-methylbutyl)-5-(trifluoromethyl)-4,1-benzoxazepin-2(3H)-one;

rel-(3S,5S)-trans-7-Chloro-1,5-dihydro-5-(2-furan-2-ylethenyl)-3-methyl-5-(trifluoromethyl)-4,1-benzoxazepin-2(3H)-one;

trans-7-Chloro-1,5-dihydro-5-(2-furan-2-yl)ethenyl-5-(trifluoromethyl)-4,1-benzoxazepin-2(3H)-one;

rel-(3S,5S)-7-Chloro-1,5-dihydro-5-(2-furanyl)ethynyl-3-methyl-5-(trifluoromethyl)-4,1-benzoxazepin-2(3H)-one;

5-Butyl-7-chloro-1,5-dihydro-5-(trifluoromethyl)-4,1-benzoxazepin-2(3H)-one;

5-Isopropylethynyl-5-trifluoromethyl-6,7-difluoro-1,5-dihydro-4,1-benzoxazepin-2(3H)-one;

rel-(3S,5S)-7-Chloro-5-cyclopropylethynyl-1,5-dihydro-3-propyl-5-(trifluoromethyl)-4,1-benzoxazepin-2(3H)-one;

rel-(3R,5S)-7-Chloro-5-cyclopropylethynyl-1,5-dihydro-3-propyl-5-(trifluoromethyl)-4,1-benzoxazepin-2(3H)-one;

rel-(3S,5S)-7-Chloro-5-cyclopropylethynyl-1,5-dihydro-3-isopropyl-5-(trifluoromethyl)-4,1-benzoxazepin-2(3H)-one;

7-Chloro-5-phenylethynyl-1,5-dihydro-5-(trifluoromethyl)-4,1-benzoxazepin-2(3H)-one;

rel-(3S,5S)-7-Chloro-5-isopropylethynyl-1,5-dihydro-3-methyl-5-(trifluoromethyl)-4,1-benzoxazepin-2(3H)-one;

7-Chloro-5-cyclopropylethynyl-1,5-dihydro-5-(trifluoromethyl)-4,1-benzoxazepin-2(3H)-one;

7-Chloro-5-isopropylethynyl-1,5-dihydro-5-(trifluoromethyl)-4,1-benzoxazepin-2(3H)-one;

trans-7-Chloro-5-(2-isopropylethenyl)-1,5-dihydro-5-(trifloromethyl)-4,1-benzoxazepin-2(3H)-one;

7-Methoxy-5-(3-methylbutyl)-1,5-dihydro-5-(trifluoromethyl)-4,1-benzoxazepin-2(3H)-one;

rel-(3S,5S)-7-Chloro-5-cyclopropylethynyl-1,5-dihydro-3-ethyl-5-(trifluoromethyl)-4,1-benzoxazepin-2(3H)-one;

rel-(3R,5S)-7-Chloro-5-cyclopropylethynyl-1,5-dihydro-3-ethyl-5-(trifluoromethyl)-4,1-benzoxazepin-2(3H)-one;

7-Chloro-5-(3-pyridylethynyl)-1,5-dihydro-5-(triflucromethyl)-4,1-benzoxazepin-2(3H)-one;

trans-7-Chloro-5-(3-pyrid-3-ylethenyl)-1,5-dihydro-5-(trifluoromethyl)-4,1-benzoxazepin-2(3H)-one;

trans-7-Fluoro-5-(2-isopropylethenyl)-1,5-dihydro-5-(trifluoromethyl)-4,1-benzoxazepin-2(3H)-one;

trans-6,7-Difluoro-5-(2-isopropylethenyl)-1,5-dihydro-5-(trifluoromethyl)-4,1-benzoxazepin-2 (3H)-one;

rel-(3S,5S)-7-Chloro-5-cyclopropylethynyl-1,5-dihydro-3-methyl-5-(trifluoromethyl)-4,1-benzoxazepin-2(3H)-one;

rel-(3S,5S)-trans-7-Chloro-5-(2-cyclopropylethenyl)-1,5-dihydro-3-methyl-5-(trifluoromethyl)-4,1-benzoxazepin-2(3H)-one;

rel-(3S,5S)-trans-7-Chloro-5-(2-cyclopropylethenyl)-1,5-dihydro-3-propyl-5-(trifluoromethyl)-4,1-benzoxazepin-2(3H)-one;

rel-(3S,5S)-7-Chloro-5-(3-furanylethynyl)-1,5-dihydro-3-methyl-5-(trifluoromethyl)-4,1-benzoxazepin-2(3H)-one;

rel-(3S,5S)-7-Chloro-5-(3-furanylethynyl)-1,5-dihydro-3-ethyl-5-(trifluoroinethyl)-4,1-benzoxazepin-2(3H)-one;

rel-(3S,5S)-7-Difluoro-5-cyclopropylethynyl-1,5-dihydro-3-methyl-5-(trifluoromethyl)-4,1-benzoxazepin-2(3H)-one;

rel-(3S,5S)-6,7-Difluoro-5-cyclopropylethynyl-1,5-dihydro-3-ethyl-5-(trifluoromethyl)-4,1-benzoxazepin-2(3H)-one;

rel-(3S,5S)-trans-6,7-Difluoro-5-(2-cyclopropylethenyl)-1,5-dihydro-3-methy-5-(trifluoromethyl)-4,1-benzoxazepin-2(3H)-one;

(+)-(3S,5S)-7-Chloro-5-cyclopropylethynyl-1,5-dihydro-3-methyl-5-(trifluoromethyl)-4,1-benzoxazepin-2(3H)-one;

(3S)-7-Chloro-5-cyclopropylethynyl-1,5-dihydro-5-(trifluoromethyl)-4,1-benzoxazepin-2(3H)-one;

rel-(3S,5S)-trans-7-Chloro-5-(2-cyclopropylethenyl)-1,5-dihydro-3-ethyl-5-(trifluoromethyl)-4,1-benzoxazepin-2(3H)-one;

(+)-(3S,5S)-trans-7-Chloro-5-(2-cyclopropylethenyl)-1,5-dihydro-3-methyl-5-(trifluoromethyl)-4,1-benzoxazepin-2(3H)-one;

(+)-(3S,5S)-trans-7-Chloro-5-(2-cyclopropylethenyl)-1,5-dihydro-3-ethyl-5-(trifluoromethyl)-4,1-benzoxazepin-2(3H)-one;

rel-(3S,5S)-7-Chloro-5-(2-cyclopropylethynyl)-1,5-dihydro-3-ethenyl-5-(trifluoromethyl)-4,1-benzoxazepin-2(3H)-one;

rel-(3S,5S)-trans-7-Chloro-5-(2-cyclopropylethenyl)-1,5-dihydro-3-ethenyl-5-(trifluoromethyl)-4,1-benzoxazepin-2(3H)-one;

rel-(3S,5S)-7-Chloro-5-(2-cyclopropylethynyl)-1,5-dihydro-3-cyclopropyl-5-(trifluoromethyl)-4,1-benzoxazepin-2(3H)-one;

rel-(3S,5S)-trans-7-Chloro-5-(2-cyclopropylethenyl)-1,5-dihydro-3-cyclopropyl-5-(trifluoromethyl)-4,1-benzoxazepin-2(3H)-one;

rel-(3S,5S)-6,7-Difluoro-5-(2-cyclopropylethynyl)-1,5-dihydro-3-ethenyl-5-(trifluoromethyl)-4,1-benzoxazepin-2(3H)-one;

rel-(3S,5S)-6,7-Difluoro-5-(2-cyclopropylethynyl)-1,5-dihydro-3-cyclopropyl-5-(trifluoromethyl)-4,1-benzoxazepin-2(3H)-one;

rel-(3S,5S)-7-Fluoro-5-(2-cyclopropylethynyl)-1,5-dihydro-3-ethenyl-5-(trifluoromethyl)-4,1-benzoxazepin-2(3H)-one;

rel-(3S,5S)-7-Fluoro-5-(2-cyclopropylethynyl)-1,5-dihydro-3-methyl-5-(trifluoromethyl)-4,1-benzoxazepin-2(3H)-one;

rel-(3S,5S)-7-Fluoro-5-(2-cyclopropylethynyl)-1,5-dihydro-3-ethyl-5-(trifluoromethyl)-4,1-benzoxazepin-2(3H)-one;

rel-(3S,5S)-trans-7-Fluoro-5-(2-cyclopropylethenyl)-1,5-dihydro-3-methyl-5-(trifluoromethyl)-4,1-benzoxazepin-2(3H)-one;

rel-(3S,5S)-trans-7-Fluoro-5-(2-cyclopropylethenyl)-1,5-dihydro-3-ethyl-5-(trifluoromethyl)-4,1-benzoxazepin-2(3H)-one;

rel-(3S,5S)-6,7-Methylenedioxy-5-(2-cycloprcpylethynyl)-1,5-dihydro-3-methyl-5-(trifluoromethyl)-4,1-benzoxazepin-2(3H)-one;

rel-(3S,5S)-6,7-Methylenedioxy-5-(2-cycloprcpylethynyl)-1,5-dihydro-3-ethyl-5-(trifluaromethyl)-4,1-benzoxazepin-2(3H)-one;

rel-(3S,5S)-trans-6,7-Methylenedioxy-5-(2-cyclopropylethenyl)-1,5-dihydro-3-methyl-5-(trifluoromethyl)-4,1-benzoxazepin-2(3H)-one; and, rel-(3S,5S)-trans-6,7-Methylenedioxy-5-(2-cyclopropylethenyl)-1,5-dihydro-3-ethyl-5-(trifluoromethyl)-4,1-benzoxazepin-2(3H)-one;

or a pharmaceutically acceptable salt form thereof.

11. The method of claim 1, wherein the compound is of formula II:

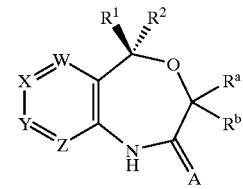

II or a stereoisomer or pharmaceutically acceptable salt form thereof.

12. The method of claim 1, wherein the compound is of formula IIa:

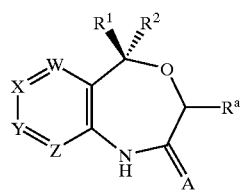

IIa or a stereoisomer or pharmaceutically acceptable salt form thereof, wherein $R^1$ is $CF_3$.

13. A method according to claim 9, wherein, the reverse transcriptase inhibitor is a nucleoside reerse transcriptase inhibitor.

14. A method according to claim 9, wherein, the reverse transcriptase inhibitor is selected from AZT (azidothymidine), 3TC (β-L-3'-thia-2',3'-dideoxycytidine), efavirenz, rescriptor, ddI (dideoxyinosine), ddC (dideoxycytidine), and d4T (2',3'-didehydro-3'-deoxythimidine), and the protease inhibitor is selected from saquinavir, ritonavir, indinavir, VX-478 (amprenavir, 4-amino-N-[2(R)-hydroxy-4-phenyl-3(S)-[tetrahydrofuran-3(S)-yloxycarbonylamino]butyl]-N-isobutylbenzenesulfonamide), nelfinavir, KNI-272 (3-(2-Hydroxy-3-{2-[2-(isoquinolin-5-yloxy)-acetylamino]-3-methylsulfanyl-propionylamino}-4-phenyl-butyryl)-thiazolidine-4-carboxylic acid tert-butylamide), CGP-61755 (lasinavir), and U-103017 (4-cyano-N-[3-[cyclopropyl(5,6,7,8,9,10-hexahydro-4-hydroxy-2-oxo-2H-cycloocta[b]pyran-3-yl)methyl]phenyl]-benzenesulfonamide).

15. A method according to claim 14, wherein, the reverse transcriptase inhibitor is selected from AZT (azidothymidine), efavirenz, rescriptor, and 3TC (β-L-3'-thia-2',3'-dideoxycytidine) and the protease inhibitor is selected from saquinavir, ritonavir, indinavir, and nelfinavir.

16. A method according to claim 15, wherein, the reverse transcriptase inhibitor is AZT (azidothymidine).

17. A method according to claim 15, wherein, the protease inhibitor is indinavir.

* * * * *